US006821505B2

(12) United States Patent
Ward

(10) Patent No.: US 6,821,505 B2
(45) Date of Patent: Nov. 23, 2004

(54) IMMUNOGLOBIN-LIKE DOMAINS WITH INCREASED HALF LIVES

(75) Inventor: Elizabeth Sally Ward, Dallas, TX (US)

(73) Assignee: Board of Regents, The University of Texas System, Austin, TX (US)

(*) Notice: Subject to any disclaimer, the term of this patent is extended or adjusted under 35 U.S.C. 154(b) by 152 days.

(21) Appl. No.: 09/933,497

(22) Filed: Aug. 20, 2001

(65) Prior Publication Data

US 2002/0098193 A1 Jul. 25, 2002

Related U.S. Application Data

(62) Division of application No. 08/811,463, filed on Mar. 3, 1997, now Pat. No. 6,277,375.

(51) Int. Cl.[7] ...................... A61K 39/395; C07K 16/00
(52) U.S. Cl. ...................... 424/9.1; 424/9.2; 424/133.1; 435/7.21; 530/387.3
(58) Field of Search ........................ 424/133.1, 9.1–9.2; 530/387.3; 435/7.21

(56) References Cited

U.S. PATENT DOCUMENTS 5,747,035 A * 5/1998 Presta et al. ............. 424/144.1

FOREIGN PATENT DOCUMENTS

| EP | 0 327 378 | 8/1989 |
|----|-----------|--------|
| WO | WO 93/22332 | 11/1993 |
| WO | WO 94/04689 | 3/1994 |

OTHER PUBLICATIONS

Ames, Prody, Kustu, "Simple, rapid and quantitative release of periplasmic proteins by chloroform," *J. Bacteriol.*, 160:1181–1183, 1984.
Brambell, Hemmings, Morris, "A theoretical model of gammaglobulin catabolism", *Nature*, 203:1352–1355, 1964.
Burmeister, Huber, Bjorkman, "Crystal structure of the complex of rat neonatal Fc receptor with Fc", *Nature*, 372:379–383, 1994.
Deisenhofer, "Crystallographic refinement and atomic models of human Fc Fragment and its complex from fragment B of protein A from *Staphylococcus aureaus* at 2.9 and 2.8 Å resolution", *Biochemistry*, 20:2361–2370, 1981.
Duncan, Winter, "The binding site for C1q on IgG", *Nature*, 332:738–740, 1988.
Duncan, Woof, Partridge, Burton, Winter, "Localization of the binding site for the human high affinity Fc receptor on IgG", *Nature*, 332:563–564, 1988.
Edelman, Cunningham, Gall, Gottlieb, Rutishauser, Waxdal, "The covalent structure of an entire γG molecule", *Proc. Natl. Acad. Sci., USA*, 63:78–85, 1969.
Ghetie, Hubbard, Kim, Tsen, Lee, Ward, "Abnormally short serum half–lives of IgG in β2–microglobulin deficient mice", *Eur. J. Immunol.*, 26:690–696, 1996.

Hoogenboom, Griffiths, Johnson, Chiswell, Hudson, Winter, "Multisubunit proteins on the surface of filamentous phage: methodologies for displaying antibody (Fab) heavy and light chains", *Nucl. Acids Res.*, 19:4133–4137, 1991.
Horton, Hunt, Ho, Pullen, Pease, "Engineering hybrid genes without the use of restriction enzymes: gene splicing by overlap extension", *Gene*, 77:61–68, 1989.
Israel, Patel, Taylor, Marshak–Rothstein, Simister, "Requirement for a β2–microglobulin associated Fc receptor for acquisition of maternal IgG by fetal and neonatal mice", *J. Immunol.*, 154:6246–6251, 1995.
Israel, Wilsker, Hayes, Schoenfeld, Simister, "Increased clearance of IgG in mice that lack β2–microglobulin: possible protective role for FcRn", *Immunol.*, 89:573–578, 1996.
Junghans, Anderson, "The protection receptor for IgG catabolism is the β2–microglobulin–containing neonatal intestinal transport receptor", *Proc. Natl. Acad. Sci. USA*, 93:5512–5516, 1996.
Kabat, Wu, Perry, Gottesman, Foeller, "Sequences of proteins of immunological interest", U.S. Department of Health and Human Services, 1991.
Kim et al., "Catabolism of the Murine IgG1 Molecule: Evidence that Both CH2–CH3 Domain Interfaces are Required for Persistence of IgG1 in the Circulation of Mice," Scand. J. Immunol., 40:457–465, 1994.
Kim et al., "Evidence That the Hinge Region Plays a Role in Maintaining Serum Levels of the Murine IgG1 Molecule," Mol. Immunol., 32(7):467–475, 1995.
Kim, Tsen, Ghetie, Ward, "Identifying amino acid residues that influence plasma clearance of mouse IgG1 fragments by site directed mutagenesis", *Eur. J. Immunol.*, 24:542–548, 1994.
Kim, Tsen, Ghetie, Ward, "Localization of the site of the murine IgG1 molecule that is involved in binding to the murine intestinal Fc receptor", *Eur. J. Immunol.*, 24:2429–2434, 1994.
Kristoffersen, Matre, "Co–localisation of the neonatal Fcγ receptor and IgG in human placental term syncytiotrophoblast", *Eur J. Immunol.*, 26:1668–1671, 1996.

(List continued on next page.)

Primary Examiner—David Saunders
(74) Attorney, Agent, or Firm—Fulbright & Jaworski

(57) ABSTRACT

Disclosed are recombinant vectors encoding immunoglobulin-like domains and portions thereof, such as antibody Fc-hinge fragments, subfragments and mutant domains with extended biological half lives. Methods of producing large quantities of such domains, heterodimers, and fusion proteins following expression by host cells are also reported. Described are antibody Fc and Fc-hinge domains, which have the same in vivo stability as intact antibodies; and domains engineered to have increased in vivo half lives. These DNA constructs and protein domains will be useful as templates for in vitro mutagenesis and high resolution structural studies; for immunization and vaccination; and for the production of recombinant antibodies or chimeric proteins with increased stability and longevity for therapeutic and diagnostic uses.

5 Claims, 16 Drawing Sheets

OTHER PUBLICATIONS

Leach, Sedmark, Osborne, Rahill, Lairmore, Anderson, "Isolation from human placenta of the IgG transporter, FcRn, and localization to the syncytiotrophoblast", *J. Immunol.*, 157:3317–3322, 1996.

Marks, Hoogenboom, Bonnett, McCafferty, Griffiths, Winter, "By–passing immunisation: human antibodies from V–gene libraries displayed on phage", *J. Mol. Biol.*, 222:581–597, 1991.

Medesan, Matesoi, Radu, Ghetie, Ward, "Delineation of the amino acid residues involved in transcytosis and catabolism of mouse IgG1", *J. Immunol.*, in press, 1997.

Medesan, Radu, Kim, Ghetie, Ward, "Localization of the site of the IgG molecule that regulates maternofetal transmission in mice", *Eur. J. Immunol.*, 26:2533–2536, 1996.

Popov, Hubbard, Kim, Ober, Ghetie, Ward, "The stoichiometry and affinity of interaction of murine Fc fragments with the MHC class I–related receptor, FcRn", *Mol. Immunol.*, 33:521–530, 1996.

Raghavan, Bonagura, Morrison, Bjorkman, "Analysis of the pH dependence of the neonatal receptor/immunoglobulin G interaction using antibody and receptor variants", *Biochemistry*, 34:14649–14657, 1995.

Roberts, Guenthert, Rodewald, "Isolation and characterisation of the Fc receptor from the fetal yolk sac of the rat", *J. Cell Biol.*, 111:1867–1876, 1990.

Rodewald, Kraehenbuhl, "Receptor–mediated transport of IgG", *J. Cell Biol.*, 99:154s–164s, 1984.

Sarmay, Lund, Rozsnyay, Gergely, Jefferis, "Mapping and comparison of the interaction sites on the Fc region of IgG responsible for triggering antibody dependent cellular cytotoxicity (ADC) through different types of human Fc receptor", *Mol. Immunol.*, 29:633–639, 1992.

Simister, Story, Chen, Hunt, "An IgG–transporting Fc receptor expressed in the syncytiotrophoblast of human placenta", *Eur. J. Immunol*, 26:1527–1531, 1996.

Story, Mikulska, Simister, "A major histocompatibility complex class I–like Fc receptor cloned from human placenta: possible role in transfer of immunoglobulin G from mother to fetus", *J. Exp. Med.*, 180:2377–2381, 1994.

Wallace, Rees, "Studies on the Immunoglobulin–G Fc fragment receptor from neonatal rat small intestine", *Biochem. J.*, 188:9–16, 1980.

Ward, "Secretion of soluble T cell receptor fragments from recombinant *Escherichia coli* cells," *J. Mol. Biol.*, 224:885–890, 1992.

Ward, "VH shuffling can be used to convert an Fv fragment of anti–hen egg lysozyme specificity to one that recognizes a T cell receptor Vα," *Mol. Immunol.*, 32:147–156, 1994.

Ward, Guessow, Griffiths, Jones, Winter, "Binding activities of a repertoire of single immunoglobulin variable domains secreted from *Escherichia coli,*" *Nature*, 341:544–546, 1989.

Batra, et al., "Insertion of Constant Region Domains of Human $IgG_I$ into CD4–PE40 Increases its Plasma Half–Life," *Molecular Immunology*, 30(4):379–386, 1993.

Wawrzynczak, et al., "Blood Clearance in the Rat of a Recombinant Mouse Monoclonal Antibody Lacking the N–Linked Oligosaccharide Side Chains of the $C_H2$ Domains," *Molecular Immunology*, 29(2):213–220, 1992.

International Search Report dated Aug. 7, 1997 (PCT/US97/03321).

* cited by examiner

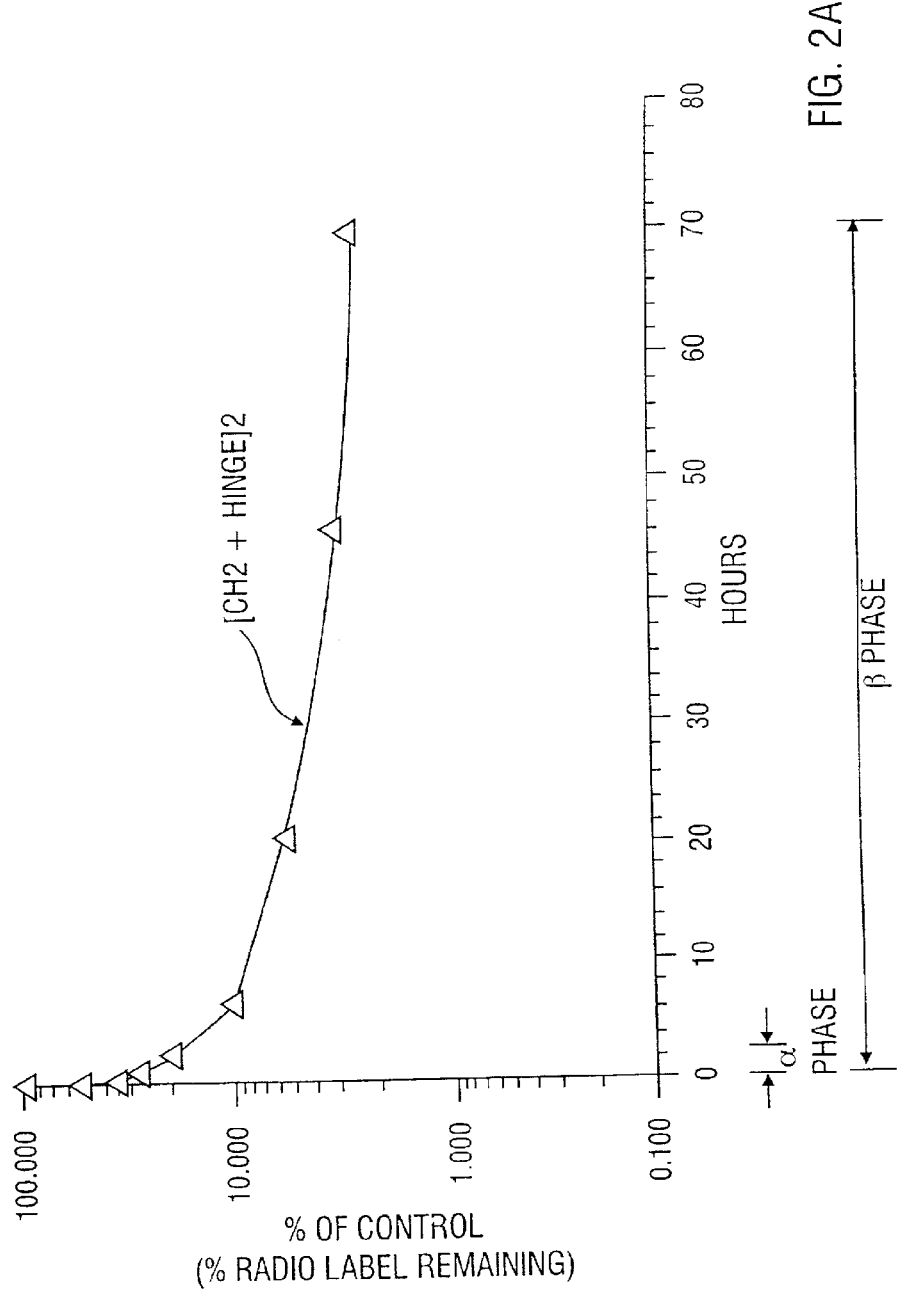

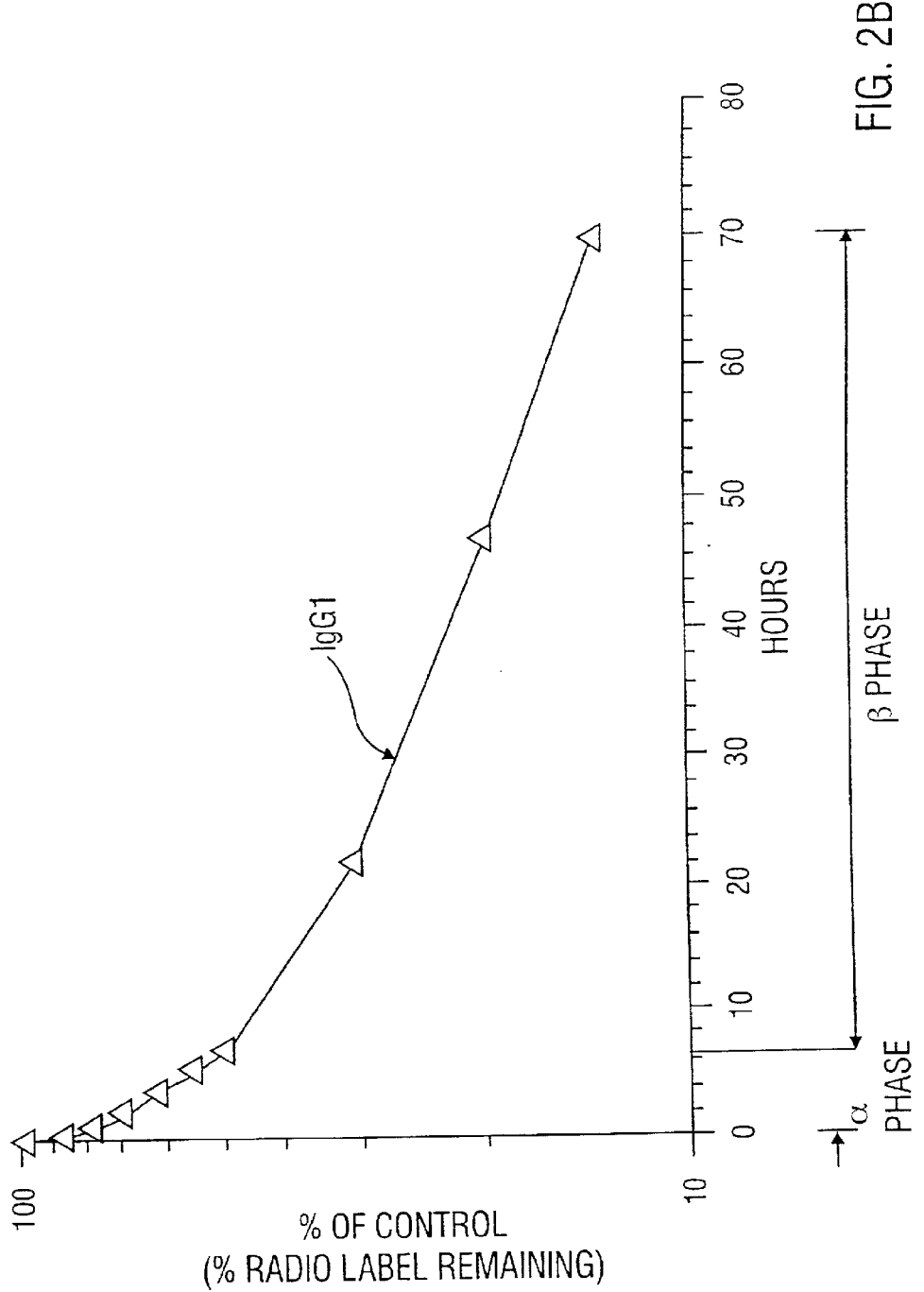

SEQUENCE LISTING

<160> NUMBER OF SEQ ID NOS: 39

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence:  Synthetic
      Primers

<400> SEQUENCE: 1
atcaccatgg ccggcagacc gaaggctcca cag                                  33

<210> SEQ ID NO 2
<211> LENGTH: 34
<212> TYPE: DNA
<213> ORGANISM: Artificial Sequence
<220> FEATURE:
<223> OTHER INFORMATION: Description of Artificial Sequence:  Synthetic
      Primers

<400> SEQUENCE: 2
tacaggtgac cttaccagga gagtgggaga ggct                                 34

<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence:  Synthetic
      Primers

<400> SEQUENCE: 3
atcaccatgg ccgtgcccag ggattgtggt tg                                   32

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 4
atcaggtgac cttggttttg gagatggttt t                              31

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 5
atcaccatgg ccgaagtatc atctgtcttc atc                            33

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 6
tctggctcct ccgtgct                                              17

<210> SEQ ID NO 7
<211> LENGTH: 35
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 7
atcatctaga ttttttttgtt ggggccaaat ttatg                         35

<210> SEQ ID NO 8
<211> LENGTH: 39
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 8
atcaccatgg ccggtaggat gcgcagcggt ctgccagcc                      39

<210> SEQ ID NO 9
<211> LENGTH: 34
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 9
atcagtcgac cttggaagtg ggtggaaagg catt                           34

<210> SEQ ID NO 10

```
<211> LENGTH: 38
<212> TYPE: DNA
<213> ORGANISM: Artificial Sequence
<220> FEATURE:
<221> NAME/KEY: modified_base
<222> LOCATION: (21)..(34)
<223> OTHER INFORMATION: N = A, G, C or T
<221> NAME/KEY: modified_base
<222> LOCATION: (20)
<223> OTHER INFORMATION: S = G or C
<223> OTHER INFORMATION: Description of Artificial Sequence: Synthetic
      Primers

<400> SEQUENCE: 10
caacacacgt gaccttagcs nncagsnnaa tsnngagc                              38

<210> SEQ ID NO 11
<211> LENGTH: 13
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 11
gtcacgtgtg ttg                                                        13

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 12
gctcctcccg gggttgcgt                                                  19

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      Primers
<221> NAME/KEY: modified_base
<222> LOCATION: (22)..(23)
<223> OTHER INFORMATION: N = A, G, C or T

<400> SEQUENCE: 13
caggaagctg acccctgtgg gnn                                             23

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      Primers
<221> NAME/KEY: modified_base
<222> LOCATION: (22)..(23)
<223> OTHER INFORMATION: N = A, G, C or T

<400> SEQUENCE: 14
ttccgtctca ggccactccc cnn                                             23

<210> SEQ ID NO 15
<211> LENGTH: 24
<212> TYPE: DNA
```

```
<213> ORGANISM: Artificial Sequence
<220> FEATURE:
<223> OTHER INFORMATION: Description of Artificial Sequence: Synthetic
      Primers

<400> SEQUENCE: 15
tcaggaagtg gctggaaagg catt                                              24

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 16
atggggatgc cactgccctg g                                                 21

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 17
ggtggttggc caggcccct                                                    19

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 18
cagtatgggc gttgtgca                                                     18

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 19
ctcagtagcg tggttgtg                                                     18

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 20
cccatcatgg cccaggactg g                                                 21

<210> SEQ ID NO 21
<211> LENGTH: 21
<212> TYPE: DNA
<213> ORGANISM: Artificial Sequence
```

-continued

```
<220> FEATURE:
<223> OTHER INFORMATION: Description of Artificial Sequence: Synthetic
      Primers

<400> SEQUENCE: 21
ccagtcctgg gccatgatgg g                                              21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 22
ggcctgcacg cgcaccatac t                                              21

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 23
agtatggtgc gcgtgcaggc cctc                                           24

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 24
agtatggtgt tggtgcag                                                  18

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic
      Primers

<400> SEQUENCE: 25
ctgcaccaac accatact                                                  18

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptides

<400> SEQUENCE: 26

Ile Met His Gln Asp
 1               5

<210> SEQ ID NO 27
<211> LENGTH: 4
<212> TYPE: PRT
<213> ORGANISM: Artificial Sequence
```

```
<220> FEATURE:
<223> OTHER INFORMATION: Description of Artificial Sequence:  Synthetic
      Peptides

<400> SEQUENCE: 27

His Asn His His
  1

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 28

Ile Gln His Gln Asp
  1               5

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 29

Lys Asn Tyr Tyr
  1

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 30

Val Leu His Gln Asp
  1               5

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 31

His Asn His Tyr
  1

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 32

Val Val His Gln Asp
  1               5
```

```
<210> SEQ ID NO 33
<211> LENGTH: 4
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 33

His Asn Arg Phe
  1

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 34

Leu Ala Ile Ser Leu Ala Pro
  1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 35

Leu Val Ile Ser Leu His Pro
  1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptides

<400> SEQUENCE: 36

Leu Leu Ile Ser Leu Phe Pro
  1               5

<210> SEQ ID NO 37
<211> LENGTH: 4
<212> TYPE: PRT
<213> ORGANISM: Mus musculus

<400> SEQUENCE: 37

Val Pro Arg Asp
  1

<210> SEQ ID NO 38
<211> LENGTH: 11
<212> TYPE: PRT
<213> ORGANISM: Mus musculus

<400> SEQUENCE: 38

Cys Gly Cys Lys Pro Cys Ile Cys Thr Val Pro
  1               5                   10
```

```
<210> SEQ ID NO 39
<211> LENGTH: 212
<212> TYPE: PRT
<213> ORGANISM: Mus musculus

<400> SEQUENCE: 39

Glu Val Ser Ser Val Phe Ile Phe Pro Pro Lys Pro Lys Asp Val Leu
 1               5                  10                  15

Thr Ile Thr Leu Thr Pro Lys Val Thr Cys Val Val Val Asp Ile Ser
            20                  25                  30

Lys Asp Asp Pro Glu Val Gln Phe Ser Trp Phe Val Asp Asp Val Glu
        35                  40                  45

Val His Thr Ala Gln Thr Gln Pro Arg Glu Glu Gln Phe Asn Ser Thr
    50                  55                  60

Phe Arg Ser Val Ser Glu Leu Pro Ile Met His Gln Asp Trp Leu Asn
65                  70                  75                  80

Gly Lys Glu Phe Lys Cys Arg Val Asn Ser Ala Ala Phe Pro Ala Pro
                85                  90                  95

Ile Glu Lys Thr Ile Ser Lys Thr Lys Gly Arg Pro Lys Ala Pro Gln
            100                 105                 110

Val Tyr Thr Ile Pro Pro Lys Glu Gln Met Ala Lys Asp Lys Val
        115                 120                 125

Ser Leu Thr Cys Met Ile Thr Asp Phe Phe Pro Glu Asp Ile Thr Val
    130                 135                 140

Glu Trp Gln Trp Asn Gly Gln Pro Ala Glu Asn Tyr Lys Asn Thr Gln
145                 150                 155                 160

Pro Ile Met Asn Thr Asn Gly Ser Tyr Phe Val Tyr Ser Lys Leu Asn
                165                 170                 175

Val Gln Lys Ser Asn Trp Glu Ala Gly Asn Thr Phe Thr Cys Ser Val
            180                 185                 190

Leu His Glu Gly Leu His Asn His His Thr Glu Lys Ser Leu Ser His
        195                 200                 205

Ser Pro Gly Lys
    210
```

IMMUNOGLOBIN-LIKE DOMAINS WITH INCREASED HALF LIVES

This application is a division of U.S. application Ser. No. 08/811,463, filed Mar. 3, 1997 and now U.S. Pat. No. 6,277,375.

The U.S. Government owns certain rights in the present invention pursuant to NIH grants R29 AI31592-01, AI32413, AI39167 and AI33111.

BACKGROUND OF THE INVENTION

1. Field of the Invention

The present invention relates generally to the field of the transport of serum proteins and antibodies mediated by the Fc receptor, FcRn, and further to the effect on serum half life of agents that interact with the Fc receptor in a pH dependent way.

2. Description of Related Art

IgGs constitute the most prevalent immunoglobin class in the serum of man and other mammals and are maintained at remarkably constant levels. Recent studies indicate that the major histocompatibility complex (MHC)-class I related receptor, FcRn, is involved in the homeostasis of serum IgGs (Ghetie et al., 1996; Junghans and Anderson, 1996; Israel et al., 1996). This receptor most likely acts as a salvage receptor, and this would be consistent with its known ability to transcytose IgGs in intact form across the neonatal gut (Wallace and Rees, 1980; Rodewald and Kraehenbuhl, 1984) and yolk sac (Roberts et al., 1990; Israel et al., 1995) or placenta (Kristoffersen and Matre, 1996; Simister et al., 1996; Leach et al., 1996). The interaction site of FcRn on mouse IgG1(mIgG1) has been mapped using site-directed mutagenesis of recombinant Fc-hinge fragments, followed by analysis of these fragments both in vivo and in vitro(Kim et al., 1994b; Medesan et al., 1996; 1997). From these studies, I253 (EU numbering (Edelman et al., 1969)), H310, H435 and to a lesser extent, H436 play a central role in this interaction. These amino acids are located at the CH2–CH3 domain interface (Deisenhofer, 1981), and the mapping of the functional site to these residues is consistent with the X-ray crystallographic structure of rat FcRn complexed with rat Fc (Burmeister et al., 1994b).

The FcRn interaction site encompasses three spatially close loops comprised of sequences that are distal in the primary amino acid sequence. The central role of Fc histidines in building this site accounts for the marked pH dependence (binding at pH 6.0, release at pH 7.4) of the Fc-FcRn interaction (Rodewald and Kraehenbuhl, 1984; Raghavan et al., 1995; Popov et al., 1996), as the pKa of one of the imidazole protons lies in this pH range. I253, H310, H435 and to a lesser degree, H436, are highly conserved in IgGs of both human and rodent IgGs (Kabat et al., 1991). This, taken together with the isolation of a human homolog of FcRn (Story et al., 1994), indicate that the molecular mechanisms involved in IgG homeostasis are common to both mouse and man and this has implications for the modulation of the pharmacokinetics of IgGs for use in therapy.

To date, in studies to identify the FcRn interaction site on Fc, mutations of Fc-hinge fragments have been made that reduce the serum half lives of the corresponding Fc-hinge fragments (Medesan et al., 1997; Kim et al., 1994a). The correlation between serum half life and binding affinity for FcRn is excellent for these mutated Fc-hinge fragments (Kim et al., 1994b; Popov et al., 1996), suggesting that if the affinity of the FcRn-Fc interaction could be increased, whilst still retaining pH dependence, this would result in an Fc fragment with prolonged serum persistence. Production of such a fragment would be a significant advance in the engineering of a new generation of therapeutic IgGs with improved pharmacokinetics such as increased persistence in the circulation. But to date, no such fragments have been produced.

Immunoglobulin Fc domains are also of great interest for purposes of studying the mechanisms of antibody stabilization, catabolism and antibody interactions with further molecules of the immune system. These include, depending on the class of antibody, interactions with complement, and binding to specific receptors on other cells, including macrophages, neutrophils and mast cells. More detailed knowledge of the biology of Fe regions is important in understanding various molecular processes of the immune system, such as phagocytosis, antibody-dependent cell-mediated cytotoxicity and allergic reactions.

The production of a longer-lived Fc fragment that has increased binding to FcRn would be attractive, since such a fragment could be used to tag therapeutic reagents. Chimeric proteins produced in this manner would have the advantage of high in vivo stability which would allow fewer doses of the agent to be used in therapy and possibly even allow lower doses of the agent to be used through its increased persistence in the bloodstream. Unfortunately,methodology for generating proteins, such as antibody fragments, with increased serum persistence has not yet been developed.

SUMMARY OF THE INVENTION

The present invention seeks to overcome deficiencies in the art by providing functional proteins, antibodies or other agents that have an increased serum half-life through the interaction with Fc receptor (FcRn). These functional agents include any molecule that binds to FcRn in a pH dependent way such that binding affinity is strong at about pH 6 to about pH 6.5 relative to binding at pH 7.4. Physiologically, this allows the agent to be salvaged by FcRn at lower pH and released into the essentially neutral pH environment of the serum. The present disclosure includes protein and peptide compositions having altered serum half-lives relative to IgG, methods of making such proteins or peptides, either starting with a known sequence or by screening random sequences, and methods of screening unknown candidate agents for pH dependent FcRn binding. In addition, disclosed herein are methods of making an agent with altered serum half-life by conjugating or otherwise binding of that agent to a moiety identified as having an increased serum half-life through its interaction with FcRn. Such agents would include, but are not limited to antibodies, fragments of antibodies, hormones, receptor ligands, immunotoxins, therapeutic drugs of any kind, T-cell receptor binding antigens and any other agent that may be bound to the increased serum half life moieties of the present invention.

Also disclosed are methods of increasing the FcRn binding affinity of an FcRn binding protein or peptide so that the protein or peptide will have an increased serum half-life. These methods include identifying amino acids that directly interact with FcRn. These amino acids may be identified by their being highly conserved over a range of species, or by any other method. Other methods would include, for example, mutation or blocking of the amino acid and screening for reduced binding to FcRn, or by a study of three dimensional structure of the interaction, or by other methods known in the art. When those residues are identified that directly interact, then secondary amino acids are identified whose side chains are in the spatial vicinity of the direct interaction. In the case of antibodies, these secondary amino acids often occur in loops so that they are exposed to the solvent. In this way, mutation of these amino acids is not expected to disrupt the native protein structure. These identified secondary amino acids are then randomly mutated and the mutated proteins or peptides are then screened for increased binding affinity for FcRn at about pH 6 relative to the non-mutated protein or peptide. This method is applicable to any protein or peptide that binds FcRn in a pH dependent way and all such proteins or peptides would be encompassed by the present claimed invention. It is also understood that random mutation, in and of itself, does not constitute the invention, and that the secondary amino acids may be specifically mutated or modified or derivatized in any way known in the art and then screened for the effect on FcRn binding.

In certain broad aspects, the invention encompasses the design and production of recombinant antibody or antibody Fc-hinge domains engineered to have increased in vivo, or serum half lives. The Fc-hinge domain mutants with increased serum half lives of the present invention are generally defined as mutants in which one or more of the natural residues at the CH2–CH3 domain interface of the Fc-hinge fragment have been exchanged for alternate amino acids. Such Fc-hinge domain mutants may also be functionally defined as mutants which exhibit impaired SpA (Staphylococcal protein A) binding. In preferred embodiments, the increased half-life Fc-hinge mutants will have changes in certain amino acids between about residue 252 and about residue 436, which have been discovered to form, or be in close proximity to, the 'catabolic control site'.

In a further embodiment, the invention encompasses the isolation of peptides or agents that bind to FcRn with an affinity that may not necessarily be greater than that of the IgG:FcRn interaction yet the peptides or agents still have a measurably longer half life than a similar peptides or agents that do not bind to FcRn in a pH dependent manner as described herein. It is envisioned that such peptides or agents are useful as a stabilization "tag" for a therapeutic agent or protein.

More particularly, the present invention concerns mutant Ig domains and antibodies containing domains in which one or more of the following amino acids have been exchanged for other residues: threonine (thr) at position 252, threonine at position 254, threonine at position 256 SEQ ID NO:37 (position 256 corresponds to residue 21 in SEQ ID NO: 39) (wherein the amino acids are numbered according to Kabat et al., (1991)). To increase the half life of an Fc-hinge domain, or intact antibody, any of the above residues may be substituted for any other amino acid residue and then variants that have higher affinity for FcRn may be selected using bacteriophage display, for example, or by any other method known to those of skill in the art. Substitution can advantageously be achieved by any of the molecular biological techniques known to those of skill in the art, as exemplified herein below, or even by chemical modification.

Certain increased half-life antibodies or domains will be those which include one or more of the following substitutions on the Kabat numbering system, or their equivalents on different numbering systems: threonine (thr) 252 to leucine (leu) 252, threonine 254 to serine (ser) 254, threonine 256 to phenylalanine (phe) 256. An example as disclosed herein is the triple mutant termed LSF which contains the three mutations: threonine 252 to leucine 252, threonine 254 to serine 254, threonine 256 to phenylalanine 256.

The production of Fc-hinge domains with longer in vivo half lives is an advantageous development in that it further delineates the site for the control of IgG1 catabolism to a specific region of the Fc-hinge fragment, and in practical terms, it has several important applications. It allows the design and construction of antibody molecules, domains, or fragments, such as bivalent Fab fragments, with longer half lives. These would be generally useful in that the slower biological clearance times would result in fewer administrations of any antibody or vaccine such that fewer "booster" vaccinations may be required. Furthermore, these molecules with longer half lives can be used to tag other therapeutic molecules, such as vaccine molecules. The catabolic site delineated in this invention is distinct from the ADCC and complement fixing sites. This is important as antibodies may be produced which are completely functional and which have longer half lives. Other important uses include, for example, antibody-based systemic drug delivery, the creation of immunotoxins with longer lives or even antibody-based immunotherapy for chronic illnesses or conditions such as hay fever or other allergic reactions, or treatment of T-cell mediated autoimmune disorders by anti-T-cell receptor antibodies or T-cell antigens.

The Fc-hinge domain mutants may also be employed in embodiments other than those involving clinical administration, for example, in the isolation of receptors involved in IgG catabolism. To this end, one may use screening assays or differential screening assays in which the mutants would exhibit binding or increased binding to a potential catabolic receptor.

The discoveries disclosed herein concerning antibody catabolism are also envisioned to be useful to increase the in vivo half life of virtually any recombinant protein, and particularly a recombinant antibody, which one desires to administer to a human or animal. An antibody or recombinant protein that was found to be cleared from the body more quickly than ideally desired could be engineered at the residues identified herein, or in the vicinity of amino acids that are discovered to directly interact with FcRn, such that its in vivo half life was increased.

In certain other embodiments, the present invention contemplates the creation of recombinant molecules, particularly antibody constructs, including vaccines and immunotoxins, with increased in vivo half lives. Longevity of recombinant molecules is often needed, and several protocols would benefit from the design of a molecule which would be more slowly removed from circulation after exerting its designed action. This may include, for example, antibodies administered for the purpose of scavenging pathogens, toxins or substances causing biological imbalances and thereby preventing them from harming the body; and antibodies designed to provide long-term, systemic delivery of immunotherapeutic drugs and vaccines.

To generate a domain, antibody or antibody construct with a longer half-life, one would modify the natural residues at the CH2–CH3 domain interface of the Fc-hinge which either form the "catabolic control site" or are in close proximity to it. Several such catabolism controlling mutations are described herein which may be straightforwardly engineered into an antibody molecule or antibody conjugate. These include, substituting another residue for threonine 252, threonine 254, threonine 256, methionine 309, glutamine 311 and/or asparagine 315 SEQ ID NO:37 (position 256 corresponds to reduce 80 in SEQ 10 No:39) (Kabat et al., 1991). The present invention also provides an advantageous method for determining other residues important for catabolism control.

The proteins or peptides of the present invention may be expressed from recombinant plasmids or expression vectors adapted for expression of immunoglobulin-like domains, such as antibody domains, or other proteins or peptides in recombinant host cells. Recombinant plasmids thus may comprise a DNA segment coding for one or more immunoglobulin-like domains. Accordingly, any one or more of a wide variety of immunoglobulin-like domains or other protein or peptide may be incorporated into a recombinant vector and expressed in a host cell in accordance herewith. These include, but are not limited to, variable or constant domains from IgG, IgM, IgA, IgD, IgE, T cell receptors, MHC class I or MHC class II, and also, CD2, CD4, CD8, CD3 polypeptides, Thy-1 and domains from the PDGF receptor, N-CAM or Ng-CAM.

In certain embodiments, the present invention concerns the expression and production of antibody constant domains. The production of antibody Fc-hinge, Fc, CH2-hinge or CH3 domains is preferred, with Fc-hinge or Fc domains being particularly preferred due to their longer in vivo half lives. In other instances, the production of Fc-hinge domains (or antibodies incorporating such domains) with mutations at thr 252, thr 254 or thr 256 is preferred as these have specifically longer half lives. Such mutants are exemplified by thr 252 to leu 252, thr 254 to ser 254 and thr 256 to phe 256.

Various segments or subfragments of any of the above domains, as well as other variable or constant domains, may also be employed in accordance herewith. These domains include, for example, the immunoglobulin domains CH 1. Variations of immunoglobulin domains other than those specifically described above also fall within the scope of the invention. Such variations may arise from naturally-occurring or genetically engineered mutations, such as point mutations, deletions and other alterations affecting one or more amino acids or the addition of amino acids at the N or C termini.

Furthermore, while the invention has been illustrated with murine FcRn and immunoglobulin fragments, similar strategies are applicable to immunoglobulin-like domains or other proteins or peptides from a variety of other species, including mammals such as rat, and more particularly, human immunoglobulin-like molecules. In light of the structural similarity of the immunoglobulin-like domains, and the conservation of the immunoglobulin superfamily throughout evolution, it is contemplated that the techniques of the present invention will be directly applicable to the expression and recombinant production of an immunoglobulin-like domain from any given species.

Other DNA segments may also be included linked to the immunoglobulin-like domains described. For example, one or more recombinant antibody variable domains of varying specificities may be linked to one or more antibody constant domains, immunoglobulin constant domains, or even other proteins, such as bacteriophage coat protein genes, hormones or antigens, including T-cell receptor antigens. The antibody constant domains of the present invention may also be combined with another immunoglobulin domain, or indeed, with any other protein. The immunoglobulin constant domains may be variously expressed as a single domain, such as a CH3 domain; or in combination with one, two, three or more domains, such as, for example, as a CH2-hinge domain, an Fc domain, or an entire Fc-hinge domain. In particular embodiments, discussed in more detail below, Fc or Fc-hinge domains may be linked to any protein to produce a recombinant fusion with enhanced biological stability, or certain mutants may be employed to create antibodies or fusion proteins with increased half lives.

Once expressed, any of the products herein could be radiolabeled or fluorescently labeled, or attached to solid supports, including sepharose or magnetic beads or synthetic bilayers such as liposomes. The products could also be linked to carrier proteins such as bovine serum albumin. The Fc constant domains, or constant domains in combination with other proteins, could also be linked synthetically to co-receptors such as the extracellular domains of CD4 or CD8.

Recombinant, or cloning, vectors are included in one aspect of the present invention. Such vectors and DNA constructs will be useful not only for directing protein expression, but also as for use as templates for in vitro mutagenesis. Vectors will generally include a leader sequence, preferably pelB (Better et al., 1988), although other leader sequences may be used, for example, alkaline phosphatase (phoA) or ompA. In a preferred embodiment, the pelB leader segment is modified with a unique restriction site, such as NcoI, allowing insertion of antibody variable domain genes. Introduction of such restriction sites is a convenient means of cloning in a DNA segment in the same reading frame as the leader sequence.

Modification of the leader sequence DNA may be achieved by altering one or more nucleotides employing site-directed mutagenesis. In general, the technique of site specific mutagenesis is well known in the art as exemplified by publications (Carter et al., 1985; Sambrook et al., 1989). As will be appreciated, the technique typically employs a phagemid vector which exists in both a single stranded and double stranded form. Alternatively, mutants may be generated by using the PCR™. Typical vectors useful in site-directed mutagenesis include vectors such as the M13 phage (Messing et al., 1981) or pUC 119. These vectors are readily commercially available and their use is generally well known to those skilled in the art. Alternatively, methods of site-directed mutagenesis employing double stranded plasmids or phagemids and the like are also well known in the art and may also be used in the practice of the present invention.

Site directed mutagenesis in accordance herewith is performed by first obtaining a single stranded vector which includes within its sequence the DNA sequence encoding a leader sequence, pelB being used herewith. An oligonucleotide primer bearing the desired mutated sequence is prepared, generally synthetically, for example by the method of Narang et al., (1980). The primer is annealed with the single stranded vector and subjected to DNA polymerizing enzymes such as the E. coli polymerase I Klenow fragment. In order to complete the synthesis of the mutation bearing strand, a heteroduplex is formed wherein one strand encodes the original non-mutated sequence and the second strand bears the desired mutation. The heteroduplex may be transformed into a bacterial cell, with E. coli. being preferred. Clones are screened using colony hybridization and radio-labeled mutagenic oligonucleotides to identify colonies which contain the mutated plasmid DNA (Carter et al., 1985). PCR™ directed mutagenesis, using double-stranded DNA templates, is particularly suitable for generating increased half life mutants. PCR™ mutagenesis typically involves the use of a primer encoding one or more alternate or random amino acid in one or more amplification reactions.

Constructs may also include a "tag" useful for isolation and purification of the expressed polypeptide product. Tags are relatively short DNA segments fused in-frame with a sequence encoding a desired polypeptide, such as polyhistidine, which have the function of facilitating detection, isolation and purification. For example, affinity peptides may be encoded by the segments, allowing isolation by selective binding to specific antibodies or affinity resins. Any of a number of tags may be used, including the c-myc tag, (his)$_6$ tag, decapeptide tag (Huse et al., 1989), Flag™ (Immunex) tags and so forth. A number of the tags are also useful for the detection of expressed protein using Western blotting (Ward et al., 1989; Towbin et al., 1979).

(His)$_6$ tags, for example, are preferable for purifying secreted polypeptide products on affinity metal chromatography columns based on metals such as Ni$^{2+}$. The (his)$_6$ peptide chelates Ni$^{2+}$ ions with high affinity. Polypeptide products containing these residues at the N or C termini bind to the affinity columns, allowing polypeptide impurities and other contaminants to be washed away as part of the purification process. Polypeptide products can then be eluted from the column with high efficiency using, for example, 250 mM imidazole.

Peptide tags, or linkers, may also be incorporated into the immunoglobin product. For single chain Fv or T cell receptor (TCR) fragments, preferred linker peptides include a 15-mer, for example, (gly$_4$ser)$_3$, or other linkers, such as those described in Filpula and Whitlow (1991).

As mentioned above, recombinant vectors of the present invention may also include DNA segments encoding various other proteins. In particular, it is envisioned that recombinant vectors encoding antibody Fc-hinge or Fc domains may also include DNA segments encoding other proteins, or fragments thereof, particularly where one wishes to produce the protein in a form that has a longer serum half life. It is envisioned that the serum stability of proteins or peptides intended for administration to animals or humans may be increased in this manner. Examples of such proteins or peptides include, for example, interleukin-2, interleukin-4, γ-interferon, insulin, T cell epitopes and the like, and even TCR V$_\alpha$ V$_\beta$. A variety of synthetic drugs could, likewise, be stabilized in this manner.

DNA segments encoding such proteins may be operatively incorporated into a recombinant vector, in frame with the Fc-based domain, whether upstream or downstream, in a position so as to render the vector capable of expressing a protein:Fc domain fusion protein (or a protein: Fc-hinge domain fusion protein). Techniques for the manipulation of DNA segments in this manner, for example, by genetic engineering using restriction endonucleases, will be known to those of skill in the art in light of both the present disclosure and references such as Sambrook et al. (1989).

The invention has been illustrated with prokaryotic host cells, but this is not meant to be a limitation. The prokaryotic specific promoter and leader sequences described herein may be easily replaced with eukaryotic counterparts. It is recognized that transformation of host cells with DNA segments encoding any of a number of immunoglobulin-like domains will provide a convenient means of producing fully functional proteins, such as for example, functional IgGs. Both cDNA and genomic sequences are suitable for eukaryotic expression, as the host cell will, of course, process the genomic transcripts to yield functional mRNA for translation into protein. Increased half life mutant domains and antibodies may be produced in glycosylated form in eukaryotic systems which fix complement, and mediate ADCC.

It is similarly believed that almost any eukaryotic expression system may be utilized for the expression of proteins and peptides of the present invention, e.g., baculovirus-based, COS cell-based, myeloma cell-based systems could be employed. Plasmid vectors would incorporate an origin of replication and an efficient eukaryotic promoter, as exemplified by the eukaryotic vectors of the pCMV series, such as pCMV5.

For expression in this manner, one would position the coding sequences adjacent to and under the control of the promoter. It is understood in the art that to bring a coding sequence under the control of such a promoter, one positions the 5' end of the translation initiation site of the translation reading frame of the protein between about 1 and about 50 nucleotides "downstream" of (i.e., 3' of) the chosen promoter.

Where eukaryotic expression is contemplated, one will also typically desire to incorporate into the transcriptional unit, an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

As used herein the term "engineered" or "recombinant" cell is intended to refer to a cell into which a recombinant gene, such as a gene encoding an immunoglobulin-like domain, has been introduced. Therefore, engineered cells are distinguishable from naturally occurring cells which do not contain a recombinant gene that is introduced by transfection or transformation techniques. Engineered cells are thus cells having a gene or genes introduced through the hand of man.

Suitable host cells useful in the practice of the invention include gram-negative organisms and might include *Serratia marcescens*, *Salmonella typhimurium* and similar species. A particularly preferred host cell is *Escherichia coli* and the several variants of *E. coli* that are readily available and well known to those of skill in the art.

A particular aspect of the invention is a method for the production of immunoglobulin-like domains, such as, native or mutant antibody constant domains, or subfragments or fusion proteins thereof. To produce such domains or modified domains, a gram-negative microorganism host cell is first transformed with any of the disclosed recombinant vectors, and then cultured in an appropriate bacterial culture medium under conditions to allow expression of the immunoglobulin-like domain(s), which may be subsequently isolated.

Culturing typically comprises growing and induction. Growing is conveniently performed in such media as Luria broth plus 1% glucose, 4×TY (double strength 2×TY) plus 1% glucose, minimal media plus casamino acids and 5% w/v glycerol with temperatures in the range of 20° C. to about 37° C., preferably between 25–30° C. In preferred embodiments, the media will contain a selection agent, such as ampicillin at a concentration of 0.1 mg/ml to select bacterial cells which contain the expression plasmid. Naturally, one will choose a particular selection agent in conjunction with the plasmid construct originally employed, as is known to those of skill in the art.

Induction of expression is typically performed at a point after growth has been initiated, usually after 12–16 hours at 30° C. This length of time results in the cells being in the early stationary phase at the induction stage. If the growth media contains glucose, the cells are pelleted and washed prior to addition of an inducer, such as isopropylthiogalactopyranoside (IPTG) at a concentration of 0.1–1 mM, since glucose inhibits induction of expression. Again, a variety of other inducers may be employed, according to the vector construct originally used, as is known in the art. Cells may be grown for shorter periods prior to induction, for example for 6–10 hours, or to the mid-exponential stage of growth. Cells are induced for 5–28 hours. Five to six hours of induction is a preferred induction time if the protein is to be isolated from the periplasm, since longer induction times result in the protein leaking into the culture supernatant. However, it may be desirable to isolate product from the external medium, in which case one would prefer using longer induction times. Temperatures in the range of 20° C. to 37° C. may be used as growth and induction temperatures, with 25° C. being a preferred induction temperature.

Isolating polypeptide products produced by the microbial host cell and located in the periplasmic space typically involves disrupting the microorganism, generally by such means as osmotic shock, sonication or lysis, but preferably by osmotic shock. Once cells are disrupted, cells or cell debris may be conveniently removed by centrifugation or filtration, for example. The proteins may be further purified, for example, by affinity metallic resin chromatography when appropriate peptide tags are attached to the polypeptide products.

Alternatively, if the induction period is longer than 8 hours (at 25° C., for example), so that the protein leaks into the culture supernatant, cells may be removed from the culture by centrifugation and the culture supernatant filtered and concentrated (for example, 10–20 fold). Concentrated supernatant is then dialyzed against phosphate buffered saline and separation achieved by column chromatography, such as affinity or adsorption chromatography. An example is separation through $Ni^{2+}$-NTA-agarose to separate appropriately tagged proteins such as those carrying a $(his)_6$ tag. When these tags are used in the construction of an expression vector, histidine tags are particularly preferred as they facilitate isolation and purification on metallic resins such as $Ni^{+2}$-NTA agarose.

As used herein, the term "biologically stable protein" is intended to refer to a protein which has been modified resulting in increased serum half life with respect to the original protein. This term encompasses both known recombinant proteins and also proteins for which the recombinant form has not yet been reported. As such, increased biological stability may be measured with respect to the known or original recombinant protein, or with respect to the native protein. Biological stability may be measured by a variety of in vitro or in vivo means, for example, by using a radiolabeled protein and measuring levels of serum radioactivity as a function of time, or by assaying the levels of intact antibody (of known specificity) present in the serum using ELISA as a function of time, with a particularly preferred measure of increased biological stability being evidenced by increased serum half life and decreased clearance rates.

To produce a biologically stable recombinant protein in which the protein in question is linked to an antibody Fc-hinge domain or an antibody Fc domain, in accordance herewith, one may first prepare a recombinant vector capable of expressing a protein: Fc-hinge or protein:Fc domain fusion protein in a gram-negative host, as described hereinabove. One would then insert the recombinant vector into a gram-negative bacterium and culture the bacterium under conditions effective to allow the expression of the fusion protein. Following this, one may then proceed to isolate the fusion protein so produced, for example, using the methods of the present invention.

The above method is proposed for use in the generation of a series of therapeutic compounds with improved biological stability. Such compounds include, for example, interleukin-2, insulin, interleukin-4 and interferon gamma, or even T cell receptor $V_\alpha$ $V_\beta$. The recombinant Fc domains of this invention are also contemplated to be of use in stabilizing a wide range of drugs, which would likely alleviate the need for their repeated administration. However, the present methods are not limited solely to the production of proteins for human administration, and may be employed to produce large quantities of any protein with increased stability, such as may be used, for example, in immunization protocols, in animal treatment by veterinarians, or in rodent in vivo therapy models.

A mutant Fc-hinge domain has been generated in the present invention and is herein shown to have a dramatically increased in vivo half life in comparison to native domains. The present invention therefore further encompasses methods by which to produce antibodies or proteins with extended biological half lives. These methods include, firstly, coupling a protein or an antibody variable domain to an increased half life mutant domain of the present invention, as described above. To produce such antibodies or proteins one would prepare a recombinant vector capable of expressing the desired fusion or mutated protein, insert the vector into a gram-negative bacterium, culture it to allow expression and isolate the antibody or protein so produced. These techniques are applicable to any antibody or protein which one desires to have a longer biological half life, including antibodies and immunotoxins.

Another method of the invention, particularly suited to producing antibodies with increased serum half lives, is to simply modify a given antibody at one or more of the residues disclosed herein either at, or in proximity to, the catabolic control site. This may be achieved chemically, or by random or site-directed mutagenesis and recombinant production using any known production method. A preferred method is to replace the indicated residues with all of the remaining 19 residues and then select (using phage display if more than one residue is mutated simultaneously) mutants that have higher affinity for FcRn. The selected mutants should also bind to FcRn in a pH dependent manner as described herein, the pH can be controlled during the selection steps. This selection method also is applicable to random peptide libraries or or any other randomly mutated protein. Antibodies engineered in this manner may be single antibodies, domains, Fab fragments, or antibody conjugates such as immunotoxins and antibodies used for therapeutic regimens.

Also contemplated within the scope of the invention are recombinant immunoglobulin-like domain products, such as variable or constant antibody domains; antibodies, antibody constructs, antibody domains or immunotoxins with extended half lives; or domains from MHC molecules or cell signalling molecules such as CD2, CD4, CD8, CD3, N-CAM or Ng-CAM, or PDGF receptor domains, or fragments thereof. In preferred embodiments, these will include antibody constant domain products, such as Fc-hinge, Fc, CH2-hinge and CH3 domains; and antibody Fc-hinge domains engineered to have longer in vivo half lives, such as, for example, the LSF mutant. It will be appreciated that modification and changes may be made in the composition of these domains, for example by altering the underlying DNA, and still obtain a molecule having like or otherwise desirable characteristics. As such, biological functional equivalents of these immunoglobulin-like domains and mutants such as peptides and other randomly mutated proteins that bind to FcRn are also included within the scope of the present invention.

In general, certain amino acids may be substituted for other amino acids in a protein structure without appreciable loss of interactive binding capacity with structures such as, for example, antigen-binding regions of antibodies or receptor sites. Since it is the interactive capacity and nature of a protein that defines that protein's biological functional activity, certain amino acid sequence substitutions can be made in a protein sequence (or, of course, its underlying DNA coding sequence) and nevertheless obtain a protein with like or even countervailing properties (e.g., antagonistic v. agonistic). It is thus contemplated that various changes may be made in the coding sequences of immunoglobulin-like domains without appreciable loss of the biological utility or activity of the encoded protein. It may even be possible to change particular residues in such domains to enhance their biological utility or to increase their interactive capability, for example, by increasing the binding affinity of Fc for RcRn.

As illustrated herein, transformed host cells will provide particularly good yields of immunoglobulin-like domains. The yields obtained are in the order of about 2 mg/L for CH3; 1–1.5 mg/L for CH2-hinge; 1.5–2 mg/L for Fc; and 0.5–1 mg/L for Fc-hinge. It is contemplated that such values may be readily scaled up to produce relatively large quantities of these domains in a matter of days, employing, for example, a (his)$_6$ tag for affinity purification with Ni$^{+2}$-NTA-agarose. Thus the expression system will provide a ready supply of immunoglobulin-like domain proteins which may be obtained in a relatively cost-effective manner.

Purification of immunoglobulin-like domains, such as native antibody constant domains, or Fc-hinge domains with increased half lives, may be achieved in many ways, including chromatography, density gradient centrifugation and electrophoretic methods.

The present invention facilitates the large scale production of immunoglobulin-like domains, including those derived from human sources, which may be employed in a wide variety of embodiments. These include their use in in vitro mutagenesis studies and in high resolution structural analyses, such as NMR and X-ray crystallography. Fc-hinge and Fc domain analyses have allowed the region involved in antibody catabolism to be delineated, showing that residues isoleucine (ile) 253, histidine (his) 310, his 435 and his 436 are important. Recombinant fragments, domains, or even subfragments thereof, may be used for mapping the Fc residues which are functionally important in binding to FcRn. Residues of recombinant Fc fragments may be altered, prior to expression as soluble proteins as disclosed herein, or on the surface of bacteriophage (McCafferty et al., 1990), and mutants binding with higher affinity to FcRn may be screened, or selected for, using solid surfaces coated with FcRn or FcRn in solution. The preferred method is to use FcRn in solution and then to capture FcRn:bacteriophage complexes on beads.

The large scale production of immunoglobulin Fc-hinge or Fc domains linked to other proteins or drugs also has potential for immunotherapy. In certain embodiments, chimaeric proteins or drugs may be produced which have the advantage of prolonged half lives and, since aglycosylated Fc has very low binding affinity for Fc receptors, they would not bind to the large number of immune cells that bear these receptors. This is a significant advantage since it reduces non-specific binding. Such aglycosylated Fc fragments will also not fix complement and, importantly, this would likely reduce the occurrence of local inflammatory reactions.

The present invention may also be described as a method of regulating IgG levels in serum comprising increasing FcRn binding to said IgG. This regulation may be accomplished by increasing or decreasing endogenous FcRn levels through alteration of the expression of FcRn, or by the use of recombinant cells expressing FcRn. In addition, the regulation may be accomplished by providing an FcRn with an altered binding affinity for IgG and thereby regulating IgG levels.

In a further embodiment the present invention may be extended to include other proteins, peptides or ligands, including non-protein ligands, that bind to FcRn with high affinity and in a pH dependent manner similar to that of the exemplary antibodies disclosed herein such that their serum half life is extended.

The present invention is exemplified by the production of large quantities of both variable region and constant region immunoglobulin-like domains, and genetically engineered mutant domains. Also included are examples of the production of immunoglobulin-like domains derived originally from an antibody molecule. In particular, the production of antibody Fc-hinge, Fc, CH2-hinge and CH3 domains; and Fc-hinge mutant domains with increased serum half lives, is disclosed. However, in light of such wide-ranging examples, which cover the spectrum of the immunoglobulin-like superfamily and modifications thereof, it will be understood that the present invention is not limited to these examples alone. Rather, it encompasses all the immunoglobulin-like structures described herein above.

In light of the previous discussion, the present invention may be described in certain broad aspects as a composition comprising a mutant IgG molecule having an increased serum half-life relative to IgG, and wherein said mutant IgG molecule has at least one amino acid substitution in the Fc-hinge region. The IgG may be any IgG molecule and is in certain embodiments, preferably a human IgG.

The invention may be also described in certain embodiments as a composition comprising a mutant IgG Fc-hinge fragment having an increased serum half-life relative to the serum half-life of IgG, and wherein said fragment has an increased binding affinity for FcRn. The compositions of the invention may thus comprise a molecule or fragment that has an amino acid substitution at one or more, or even three of the amino acids selected from number 252, 254, 256, 309, 311 or 315 in the CH2 domain or 433 or 434 in the CH3 domain, and in certain embodiments may have the following amino acid substitutions: leucine for threonine at position 252, serine for threonine at position 254 and phenylalanine for threonine at position 256. In the case of an antibody or particularly an IgG, increased binding affinity for FcRn may be defined as having a dissociation constant for binding to FcRn at pH 6, of less than about 7 nM as measured by surface plasmon resonance analysis. It is understood that any of the compositions of the present invention may also be defined in certain embodiments as pharmaceutically acceptable compositions.

In certain broad aspects, the invention may be described as a method of increasing the serum half-life of an agent comprising conjugating said agent to a mutant IgG or IgG Fc hinge fragment having an increased serum half life as described above. Preferred agents include, but are not limited to a therapeutic drug, an antigen binding polypeptide, an antigen or a receptor binding ligand, or even a T-cell receptor binding ligand, or a T-cell receptor domain.

The invention also encompasses a method of making an antibody with an increased serum half life comprising identifying a first amino acid in an IgG hinge region that is suspected of being directly involved in FcRn binding, identifying one or more second amino acids wherein each of said second amino acids is in the spatial region of said first amino acid, and wherein the side chain of said second amino acid is exposed to solvent in the native antibody, making an antibody with a random amino acid substitution of one or more of said second amino acids to make a mutant antibody, and identifying a mutant antibody having an increased serum half life. This method may further comprise the step of isolating the antibody. In the practice of the method, the first amino acid may be amino acid number 253, 310, 435 or 436 of the Fc fragment, and the second or secondary amino acid may be amino acid number 252, 254, 256, 309, 311 or 315 in the CH2 domain or 433 or 434 in the CH3 domain.

In certain broad aspects, the invention may be described as a composition comprising an Fc fragment comprising the fragment from about amino acid 250 to about amino acid 440 of an IgG antibody, further defined as having a higher binding affinity for FcRn than said IgG antibody, having one or more amino acid substitutions in a region near one or more FcRn binding amino acid residues and having a higher binding affinity for FcRn at pH 6 than at pH 7.4.

Another aspect of the present invention is a method of decreasing endogeneous serum IgG in a subject comprising administering to said subject an effective amount of the composition comprising proteins or peptides having increased serum half lives, and in particular administering an IgG with an increased serum half-life.

Certain embodiments of the invention also include methods of screening an agent for an increased serum half-life relative to the serum half-life of IgG, comprising the steps of obtaining a candidate agent, measuring the binding affinity of said agent to FcRn at pH 7.4 and at about pH 6, selecting a candidate agent with a higher binding affinity for FcRn at about pH 6 than at pH 7.4 and comparing the binding affinity of said selected agent to FcRn to the binding affinity of IgG to FcRn under identical conditions, wherein an increased binding affinity for FcRn relative to the binding affinity of IgG is indicative of an agent with an increased serum half-life. Certain preferred candidate agents may be a peptide or polypeptide, or even an antibody or a fragment of an antibody. In alternate embodiments the peptide may be selected from a random peptide library, or may be a randomly mutated protein, or even a synthetic peptide.

In certain embodiments, the invention may also be a method of increasing the serum half-life of a therapeutic agent comprising conjugating said therapeutic agent to an agent having an increased serum half-life relative to the serum half-life of IgG identified by the methods disclosed and claimed herein.

BRIEF DESCRIPTION OF THE DRAWINGS

FIG. 2A. Clearance curves for recombinant [CH2-hinge]$_2$. The curves are biphasic with a rapid α phase (representing equilibration of the injected protein between the intra- and extra vascular space; the α phase of the proteins are in part determined by the size) and a longer β phase (representing the catabolism of the protein in the intra-vascular space). The half life of the β phases of the fragments are given in Table I and these represent the biological half-lives of the proteins.

FIG. 2B. Clearance curves for glycosylated IgG1 molecule.

Sepharose relative to binding in absence of inhibitor (average of three separate studies).

Figure 13A:
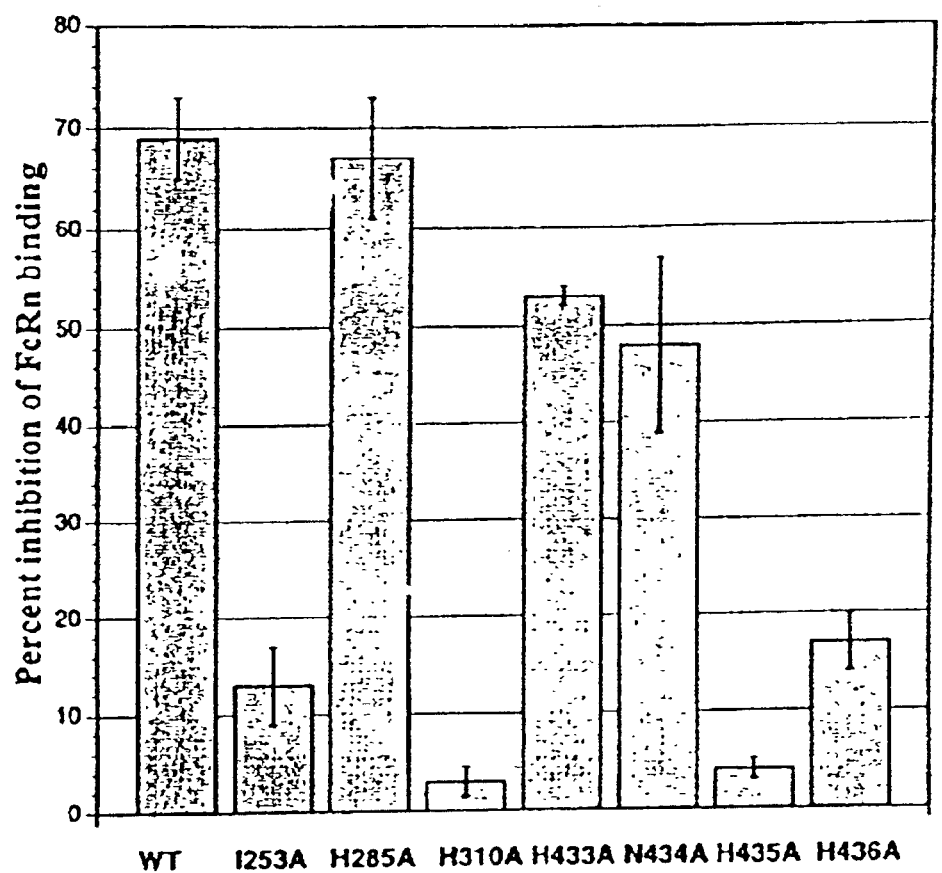
FIG. 13A. Binding of recombinant Fc-hinge fragments to FcRn. Percent inhibition of FcRn binding to mIgG1-
Figure 13B:
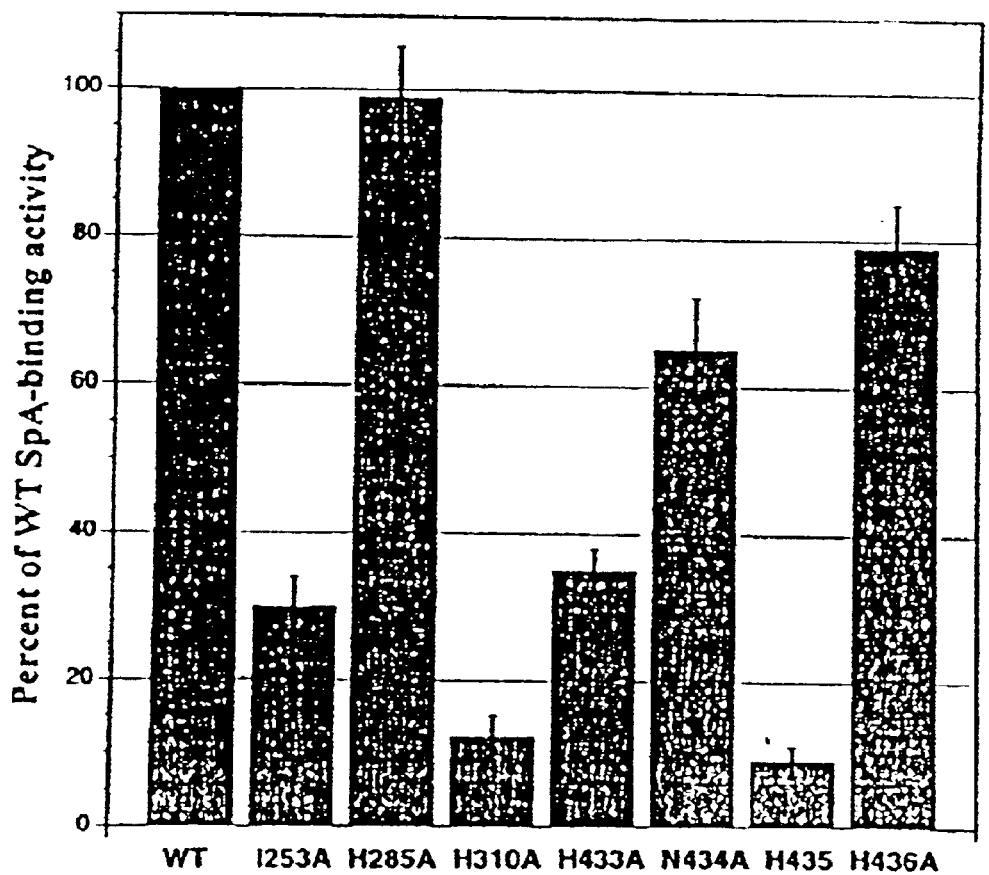

FIG. 13B. Binding of recombinant Fc-hinge fragments to SpA. Percentage of Fc-hinge fragment binding, to SpA-Sepharose relative to the binding of WT Fc-hinge (average of three separate studies).

DETAILED DESCRIPTION OF THE PREFERRED EMBODIMENTS

The present invention concerns the cloning and expression of immunoglobulin-like domains and engineered and mutant domains in host cells such that the immunoglobin-like product has increased serum persistence.

Disclosed herein are recombinant vectors encoding immunoglobulin-like domains and portions thereof, such as antibody Fc fragments and subfragments and Fc-hinge domains with extended in vivo half lives. Methods of producing large quantities of, for example, immunoglobulin Fc and Fc-hinge domains, which have the same in vivo stability as intact antibodies, are described, as are methods for producing antibodies and other molecules with increased half lives. These DNA constructs and protein domains are envisioned to be of various uses, such as in the production of immunotherapeutics or other stable recombinant proteins, or in the production of constructs.

As the invention is exemplified by the production of a variety of immunoglobulin-like domains, including antibody Fc-hinge, Fc, CH2-hinge and CH3 domains; and engineered Fc-hinge domains with extended in vivo half lives, such as, for example, the mutant termed LSF; it will be understood that other immunoglobulin-like domains may be expressed employing the methods of the present invention.

It is recognized that a considerable number of the key molecules of the immune system include homologous domains, the structure of which have been conserved throughout evolution. Such molecules are members of the immunoglobulin superfamily, which includes, not only antibodies and T cell receptors, but also MHC class I and II glycoproteins, the CD2, CD4 and CD8 cell-cell adhesion proteins, and various Fc receptors, all of which contain one or more immunoglobulin-like domains.

Each of these domains is typically about 100 amino acids in length and is thought to be folded into the characteristic sandwich-like structure made of two antiparallel β sheets, usually stabilized by a conserved disulfide bond. Many of these molecules are dimers or higher oligomers in which immunoglobulin homology units of one chain interact with those in another.

Each immunoglobulin homology unit is usually encoded by a separate exon, and its seems likely that the entire supergene family evolved from a gene coding a single immunoglobulin homology unit similar to that encoding Thy-1 or $\beta_2$-microglobulin, which may have been involved in mediating early cell-cell interactions. Since a Thy-1-like molecule has been isolated from the brain of squids, it is probable that such a primordial gene arose before vertebrates diverged from their invertebrate ancestors some 400 million years ago. New family members presumably arose by exon and gene duplications, and similar duplication events probably gave rise to the multiple gene segments that encode antibodies and T cell receptors.

Apart from antibodies and the T cell receptor, among the best characterized proteins which contain immunoglobulin-like domains are the MHC molecules and the CD4 and CD8 glycoproteins. There are two main classes of MHC (major histocompatibility complex) molecules, class I and II, each consisting of a set of cell-surface glycoproteins. Both classes of MHC glycoproteins are heterodimers with homologous overall structures, the amino-terminal domains of which are thought to be specialized for binding antigen for presentation to T cells. But FcRn, an MHC class I homolog, has a distinct function i.e. the regulation of serum IgG levels.

Each class I MHC gene encodes a single transmembrane polypeptide chain, termed α chain, most of which is folded into three extracellular, globular domains. Each α chain is noncovalently associated with a nonglycosylated small protein, termed $\beta_2$-microglobulin. $\beta_2$-microglobulin and the $\alpha_3$ domain, which are closest to the membrane, are both homologous to an immunoglobulin domain, and thus both proteins are members of the immunoglobulin superfamily. The two amino-terminal domains of the α chain, which are farthest from the membrane, contain the polymorphic (variable) residues that are recognized by T cells. T cells also recognize virally derived peptides bound to Class I molecules, and this is particularly important in cellular immunity.

In common with class I MHC molecules, class II MHC molecules are heterodimers with two conserved immunoglobulin like domains close to the membrane and two polymorphic (variable) amino-terminal domains farthest from the membrane. In these molecules, however, both chains span the membrane. There is strong evidence that the polymorphic regions of both classes of MHC molecules interact with foreign antigen and that it is the complex of MHC molecule and foreign antigen that is recognized by the T cell receptor.

CD4 and CD8 are expressed on the surface of helper and cytotoxic T cells, respectively. Both glycoproteins are thought to bind to invariant parts of MHC molecules, CD4 to class II and CD8 to class I MHC glycoproteins.

Other molecules have subsequently been shown to include immunoglobulin-like domains. These include, for example, the PDGF receptor, the extracellular domain of which is thought to be folded into five immunoglobulin-like domains. An increasing number of cell-surface glycoproteins that mediate cell-cell adhesion in vertebrates have also been identified as belonging to the immunoglobulin superfamily. These include N-CAM, a large, single-pass transmembrane glycoprotein which is expressed on the surface of nerve cells and glial cells and mediates $Ca^{2+}$-independent cell adhesion. The extracellular portion of the N-CAM polypeptide is also folded into five immunoglobulin-like domains. The L1 glycoprotein, also known as the neuron-glia cell-adhesion molecule, or Ng-CAM, is also a member of the immunoglobulin superfamily.

A: Isolation of FcRn Ligands that Have Increased Serum Persistaence

By randomly mutating regions that are in close proximity to the interaction site of FcRn on the Fc fragment, followed by selection for higher affinity binders from the library of mutants, variant Fc fragments with increased serum half lives can be isolated. These higher affinity mutants should still maintain their pH dependence of binding, as data indicate that this is an important facet of the way in which FcRn works, i.e., binding to IgGs in an acidic compartment and then being released at about pH 7.4 into the serum. Thus, this method could be used to select any ligand (protein, peptide, or even non-protein ligand) that binds to FcRn in a pH dependent way, especially when FcRn is used in soluble form to isolate the ligand. In fact, it is clear that using the disclosed invention one could isolate a ligand from either a library of synthetic chemical compounds, a peptide library or library of proteins with randomized surface loops, obtain the soluble protein or peptide in as little as one week by using standard isolation procedures well known to those of skill in the art, and then use these peptides (loops) or proteins to prepare synthetic ligands using the ACD database to identify homologs. Furthermore such FcRn ligands might be more useful than IgGs or fragments as they may well be smaller, and in the case of synthetic ligands, would be expected to be non-immunogenic. In this respect, the isolation of a ligand that has a lower affinity than IgG for FcRn, as well as those that have the same or higher affinities, is contemplated as being useful. For example, a ligand that has a several fold lower affinity than mIgG1 can still have a significantly longer half life than a similar ligand that has no detectable affinity for FcRn.

The uses of a molecule that could be used to increase the serum half life of drugs, proteins, peptides, etc. would be enormous. In principle such a molecule could be used to increase the serum persistence of any therapeutic reagent. Therefore the claimed invention is broadly applicable to an almost unlimited number of therapeutic uses for the treatment of diseases or disorders as it can be used to both reduce costs and discomfort to the patient by reducing the number of therapeutic doses are needed.

B: Antibody Constant Domains

The features of an immunoglobulin molecule that determine high stability in vivo were incompletely understood prior to the present invention. Previous studies indicate that the CH2 domain may play an important role in the control of catabolism of antibodies, and a recent study has also suggested that sequences in the CH3 domain may be involved (Ellerson et al., 1976; Mueller et al., 1990; Pollock et al., 1990; Kim et al., 1994a: Medesan et al., 1997). The presence of carbohydrate residues on the CH2 domain appears to have a minor if significant effect on the stability, and the extent of the effect is dependent on the isotype (Tao and Morrison, 1989).

As part of the present work, recombinant CH2-hinge, CH3, Fc and Fc-hinge fragments derived from the murine IgG1 constant region have been expressed from host cells. The fragments have been purified, radiolabeled and used in clearance studies in mice. The clearance rates have been compared with those of an Fv fragment and a complete glycosylated IgG1 molecule. The recombinant Fc-hinge fragments have stability properties that are very similar to those of the complete immunoglobulin molecule. In contrast, the monomeric CH2-hinge and CH3 fragments are both cleared rapidly and in a similar way to the Fv fragment. This indicates that sequences in both the CH2 and CH3 region are important for in vivo stability, and in addition, that glycosylation only plays a minor role in the control of the catabolism of this isotype.

The CH3 domain, Fc fragment and Fc-hinge fragment were all found to be homodimeric proteins. For the Fc and CH3 domain, the dimers are non-covalently linked, and are presumably stabilized by non-covalent interactions. For the Fc-hinge dimer, the fragments are covalently linked by —S—S— bridges between the hinge region cysteines.

A particularly important aspect of this study is the finding that the immunoglobulin Fc-hinge and Fc fragments, purified following expression in host cells, have the same in vivo stability as a native antibody molecule. This was determined by measuring the clearance rates of $^{125}$I-radiolabeled immunoglobulin fragments in vivo as a function of time. Results from these studies demonstrated that the recombinant aglycosylated Fc-hinge or Fc fragments have similar stability in vivo as the complete glycosylated IgG1 molecule.

The recombinant aglycosylated Fc-hinge fragment was found to have a β phase similar to that of a complete glycosylated IgG1 immunoglobulin molecule. In fact the removal of Fc-hinge resulted in a slight decrease in half life (Kim et al., 1995). These results indicate that for the murine IgG1 isotype the presence of carbohydrate residues does not appear to be necessary for in vivo stability, although it may still play a minor role. Previous data obtained using protein chemistry suggested that the CH2 domain is responsible for in vivo stability (Ellerson et al., 1976) although a recent study indicated that residues in the CH3 domain may also be involved in the catabolism control of the murine IgG2a and IgG2b isotypes (Pollock et al., 1990).

The present discoveries relating to stability are particularly important as the in vivo stability of aglycosylated Fc fragments has not been previously assessed (Nose et al., 1990). Aglycosylated Fc fragments, in comparison with the glycosylated version (prepared by proteolysis of immunoglobulin produced by mammalian cells), are known to have reduced binding to complement C1q and greatly reduced binding to Fc receptors on monocytes (Nose et al., 1990; Leatherbarrow et al., 1985; Nose and Wigzell, 1983; Tao and Morrison, 1989). However, these advantageous properties would be of little significance if the aglycosylated molecules were found to be unstable. The inventors have been able to express aglycosylated Fc fragments which proved to be stable in vivo.

The production of the IgG1 Fc-hinge or Fc fragment in *E. coli* has allowed the important residues of this region involved in controlling antibody stability and catabolism in vivo to be elucidated. These results are described in Example 8. Furthermore, following the present invention, human Fc domains may now be produced in *E. coli*, allowing further detailed studies of the human protein. Additionally, the bacterial secretion of Fc or Fc-hinge domains, or Fc or Fc-hinge domain:fusion proteins, whether of murine or human origin, is envisioned to provide a convenient, economically attractive and rapid route for the production of novel proteins that have long serum persistence.

Following structural analyses, smaller regions of the Fc structure may be employed in protein chimeras, or fusion proteins, to produce biologically stable therapeutic agents. This is particularly useful for the production of therapeutic agents which cannot be obtained from other expression systems, such as mammalian cells, due to proteolysis. As such, the Fc-hinge or Fc domains of the present invention, or portions thereof, are proposed to be useful modules for both the tagging and stabilization of recombinant molecules, including chimeric proteins of therapeutic use.

C: Catabolic Site of the IgG Molecule.

Of the Ig class (IgA, IgE, IgM, IgD and IgG), the IgG molecule has the longest in vivo half life (Zuckier et al., 1990). The region of the IgG molecule that controls catabolism (the 'catabolic site') has been known for several decades to reside in the Fc fragment. This work, carried out initially by Spiegelberg and Weigle (1966) and later confirmed by many others (reviewed in Zuckier et al., 1990), indicated that the Fc fragment produced by proteolysis has the same in vivo half life as the complete IgG molecule. Works by Dorrington and colleagues (Dorrington and Painter, 1974; Ellerson et al., 1976; Yasmeen et al., 1976) showed that a CH2 domain fragment produced by trypsin digestion had the same half life as that of the complete IgG molecule. Although both earlier and more recent data suggest that the CH2 domain is involved in the control of IgG catabolism, some of these data are not inconsistent with the additional involvement of the CH3 domain (Arend and Webster, 1977; Dima et al., 1983; Mueller et al., 1990; Kim et al., 1994a; Batra et al., 1993). Indeed, recent work has indicated that both the CH2 domain and the CH3 domain, contain sequences that control the serum persistence of IgG molecules (Kim et al., 1994a; Pollock et al., 1990, Kim et al., 1994c; Medesan et al., 1997). In particular, site-directed mutagenesis has been used to identify amino acid residues in the CH2–CH3 domain interface that are critical for the maintenance of serum IgG1 levels in mice (Kim et al., 1994a; Medesan et al., 1997), and this study therefore resulted in the precise localization of the catabolic site. These residues are highly conserved in both human and murine IgG isotypes (Kim et al., 1994a; Table I), suggesting that the catabolic sites of human and murine IgGs are the same. The effects of two double mutants (HQ-310, His310 to Ala and Gln311 to Asn; HN-433, His433 to Ala and Asn434 to Gln), rather than single mutations at these positions, and a single mutation (Ile253 to Ala253) on catabolism and intestinal transfer have been characterized (Kim et al., 1994a; Kim et al., 1994b). In a more recent study (Medesan et al., 1997) the effects of mutation of His310 to Ala310, His435 to Ala435, His436 to Ala436, His433 to Ala433, Asn434 to Ala434 or Gln434 have been analyzed.

TABLE I

Sequences of murine and human IgGs in the region of the catabolic site

|  | 252–254 | 308–312 | 433–436** |
|---|---|---|---|
| mIgG1* | T<u>I</u>T | IM<u>H</u>QD | <u>H</u>N<u>H</u><u>H</u> |
| mIgG2a | MIS | IQHQD | HNHH |
| mIgG2b | MIS | IQHQD | KNYY |
| mIgG3 | MIS | IQHQD | HNHH |
| hIgG1+ | MIS | VLHQD | HNHY |
| hIgG2 | MIS | VVHQD | HNHY |
| hIgG3 | MIS | VLHQD | HNRF |
| hIgG4 | MIS | VLHQD | HNHY |

*mIgG1 = murine IgG1, +hIgG + human IgG1
**His 433 and Asn 434 as a double mutant had an effect, but as single mutations, his 433 to ala 433 and asn 436 to ala 436, no effect was observed (Medesan et al., 1997). Residues that were mutated and found to affect clearance rate (Kim et al., 1994a) are underlined.

Mutation of His435 to Ala435 has a drastic effect on both catabolism and transcytosis, whereas mutation of His436 to Ala436 has a lesser effect (Medesan et al., 1997). Mutation of only His310 to Ala310 has the same effect as mutating both His310 to Ala310 and Gln311 to Asn311, suggesting that Gln311 is not involved in the Fc:FcRn interaction. Individual mutation of His433 to Ala and Asn434 to Ala/Gln has no effect on binding to FcRn catabolism or transcytosis whereas in earlier studies (Kim et al., 1994a; 1994c) it was noted that double mutation of His433,Asn434 did have a moderate effect. This variation is due to the perturbation of adjacent critical residues such as His435 by the double mutation (whereas single mutations are less perturbing) rather than direct involvement of 433 and 434 in the Fc:FcRn interaction.

Other residues in addition to Thr252, Thr254, Thr256, Met3.09 and Asn315 that might be useful targets for mutagenesis are Gln311, His433 and Asn434. Furthermore, data disclosed herein indicate that it is not valid to say that Gln311, His433 or Asn434 constitute the catabolic site, although double mutation of His433 and Asn434 does have an effect on catabolism.

Removal of the carbohydrate residues from the CH2 domain has a minor or no effect on the in vivo half life of IgGs, and the extent of this effect is dependent on the isotype (Nose and Wigzell, 1983; Tao and Mofrison, 1989; Wawrzynczak et al., 1989). The region of the Fc that is involved in the catabolism of IgG (Kim et al., 1994a) appears to be distinct from the sites involved in binding FcγRI, RII and RIII receptors (the 'classical' FcRs), as these recognize sequences primarily located in the lower hinge region (Duncan et al., 1988; Lund et al., 1992; Sarmay et al., 1992; Jefferis et al., 1990; Canfield and Morrison, 1991; Wawrzynczak et al., 1992). In addition, the catabolic site is distinct from the complement factor C1 q binding site (Glu318, Lys320 and Lys322) (Wawrzynczak et al., 1992; Duncan and Winter, 1988), thus mutation of the catabolic site should neither affect complement fixation nor binding to FcγRI, RII and RIII.

IgG2b and other Murine Isotypes

Murine IgG2b has been shown to have a more rapid clearance rate than IgG1, IgG2a and IgG3 (Pollock et al., 1990). Analysis if sequence differences for the residues at the CH2–CH3 domain interface that have been shown to be important in building the catabolic site indicate that in IgG2b, His433, His435, His436 of IgG1, IgG2a and IgG3 are replaced by Lys433, Tyr435 and Tyr436 in IgG2b (Table I). These sequences differences may account for the differences in clearance rates and neonatal transfer (McNabb et al., 1976; Guyer et al., 1976) that have been observed. In this respect, Scharff and colleagues (Pollock et al., 1990) have shown that sequence differences in the CH3 domain of IgG2a and IgG2b are responsible for the faster clearance rate of IgG2b relative to IgG2a, but have not identified the residues involved. In addition, murine IgG2b is not transferred across neonatal intestine as efficiently as murine IgG1 (Guyer et al., 1976). The sequence differences in the CH3 region of the murine isotypes (Table I) provide an ideal system to analyze the role of position 433, 435 and 436 in controlling catabolism and transcytosis. The conversion of his 433 to ala 433, tyrosine (tyr) 435 to his 435 and tyr 436 to his 436 in an IgG2b molecule results in a mutated IgG2b that has the same in vivo half life as murine IgG1. Furthermore, the faster clearance rate of human IgG3 relative to IgG1, IgG2 and IgG4 further indicates that residue 435 (Table I) is involved in regulating serum IgG levels.

Possible Mechanism of IgG Catabolism

The maintenance of serum IgG concentrations at a fairly constant level is of importance for effective immunity. Moreover, abnormally high (hypergammaglobulinemia) or low (hypogammaglobulinemia) serum IgG levels result in clinical symptoms. To be effective, the homeostatic mechanism that both senses and regulates serum IgG levels must be able to deal with continuous and variable production of IgG molecules by the B cells of the organism. How such homeostasis is brought about is as yet unclear, and several mechanisms have been proposed to account for the control of IgG levels in the serum (Brambell et al., 1964; Brambell, 1966; Ghetie et al., 1981). Clearly, any model must invoke a feedback system that is both sensitive and responsive to changes in serum IgG levels.

Brambell and colleagues (Brambell et al., 1964; Brambell, 1966) have proposed that a limited number of cellular receptors (designated FcRc in this proposal) bind to and protect the IgG molecules from degradation. The bound and internalized IgG molecule is protected from proteolysis and subsequently released back into the intravascular pool, whilst the IgG molecules that are internalized without bound receptors are degraded. Thus, the cells that are responsible for IgG breakdown are paradoxically also proposed to be involved in protection of IgGs against breakdown (Brambell et al., 1964; Brambell, 1966). The receptors are saturable, and consistent with this model in hypergammaglobulinemic individuals, intravascular IgG is degraded much more rapidly than in hypogammaglobulinemics. This concentration dependence of catabolic rates is called the concentration-catabolism phenomena. The receptor model also fits with recent data which shows that mutation of specific residues at the CH2–CH3 interface of the IgG1 molecule results in rapid intravascular clearance (Kim et al., 1994a), suggesting that the mutations have resulted in loss of recognition by the 'protective' receptors.

The Site of Immunoglobulin Clearance

The site(s) at which IgGs are catabolized and the proteases involved have yet to be characterized. Both liver and gastrointestinal tract have been shown to play a role in the catabolism of IgG (Covell et al., 1986; Hopf et al., 1976; Dobre and Ghetie, 1979) but neither organ, however, has been demonstrated to be the major site of catabolism. Therefore the possibility of diffuse catabolism throughout the body must be considered (Waldmann and Strober, 1969). Such diffuse catabolism could occur in the endothelial system throughout the body since the cells of this system are in close contact with the intravascular pool and IgG constantly traverses the endothelial cells to enter the extravascular space. Recent data support the notion of diffuse catabolism with possible involvement of endothelial cells.

Transfer of IgG Across Membranes (Transcytosis)

Intestinal Transfer in Newborns

The mechanisms involved in transfer of passive immunity from the mother to young (fetus/newborn) may share similarities with that involved in the control of catabolism as proposed by Brambell (1966) and supported by recent data. In rodents, intestinal transfer of IgG can occur for up to two weeks after birth and is the major route by which suckling rodents acquire maternal IgG (reviewed in Morris, 1978; Jones and Waldmann, 1972). Maternal-fetal transfer of IgGs across the yolk sac is a more minor route of transfer in rodents, in contrast to humans where maternal-fetal transfer is the only route.

An Fc receptor (FcRn) has been implicated in transfer of IgG from the colostrum or milk into the bloodstream of newborn rats and mice (Brambell, 1966; Rodewald, 1976). Consistent with its' role in neonates, the receptor FcRn is not expressed in the duodenum of adult rodents. Binding studies (Wallace and Rees, 1980; Rodewald et al., 1983) of isolated rat brush borders show that there are two classes of Fc receptors of differing affinities, and data indicate that the higher affinity FcR is involved in transcytosis (Hobbs et al., 1987; Rodewald and Kraehenbuhl, 1984). FcRn has been isolated from duodenal epithelial brush borders of suckling rates (Rodewald and Kraehenbuhl, 1984; Simister and Rees, 1985) and the corresponding genes cloned (Simister and Mostov, 1989a; Simister and Mostov, 1989b). This Fc receptor comprises a heterodimer of two polypeptides of 51 kDa and 14 kDa. Interestingly, the 14 kDa component is β2-microglobulin and the 51 kDa component is homologuous to the heavy chain of Class I MHC proteins. The protein can be expressed in high yields in recombinant form and has recently been analyzed by x-ray crystallography (Burmeister et al., 1994a; Burmeister et al., 1994b). The gene encoding murine FcRn has been isolated and shown to be highly homologous to that of rats (Ahouse et al., 1993). Interestingly, both rat and murine FcRn also share homology with a recently isolated Fc receptor derived from human placenta that is most likely involved in maternal-fetal transfer (Story et al., 1994). Thus, the available data indicate that IgG transcytosis in rats, mice and humans are carried out by similar receptors and as a consequence share a common mechanism.

The proposed mechanism of trans-intestinal transport is that FcRn on the lumenal side of intestinal epithelial cells binds IgG at pH 6–6.5 (the pH of the intestinal lumen) and the IgG-FcRn complexes are transported across the cell to the basolateral surface where exocytosis occurs into the bloodstream of the newborn rodent. Association of IgG with FcRn as it traffics through the cell is postulated to protect the IgG molecule from lysosomal degradation. The pH of the plasma (7.4) results in release of the bound IgG into the circulation. Analyses of the binding of FcRn to IgG (or Fc) show a pH dependence that is consistent with this model, with strong binding at pH 6–6.5 and very weak (if any) binding at pH 7.4 (Rodewald, 1976; Wallace and Rees, 1980). Using recombinant Fc fragments, it has been shown that murine FcRn interacts with a region of the murine IgG1 molecule that overlaps with that involved in catabolism control and encompasses Ile253, His310, Gln311, His433 and Asn434 (Kim et al., 1994b). More recent data have shown the involvement of His435 and His436, and also that His433 and Asn434 (if mutated individually and not as double mutations), do not play a role in interacting with FcRn (Medesan et al., 1997). In addition, single mutation of His310 to Ala310 has the same effect as double mutation of His310 to Ala310 and Gln311 to Asn311, indicating that Gln311 does not interact with FcRn (Medesan et al., 1997). Similar conclusions have been drawn for rat FcRn from the x-ray crystallographic data and in vitro binding studies of Bjorkman and colleagues (Burmeister et al., 1994a; Burmeister et al., 1994b; Raghavan et al., 1994). Furthermore, for intestinal transfer, data demonstrate that two FcRn sites per Fc are necessary (Kim et al., 1994b), consistent with the report that the stoichiometry of binding of rat FcRn to Fc is 2:1 (Huber et al., 1993). The involvement of His310, His435 and His436 of the IgG1 molecule in interacting with FcRn explains, in part at least, the pH dependence of the FcRn-Fc interaction (Kim et al., 1994b; Raghavan et al., 1993).

Transfer Across Murine Yolk Sac (Maternal-Fetal Transfer)

Murine FcRn is expressed at high levels in both neonatal intestine and yolk sac (Ahouse et al., 1993), and an FcR that is structurally similar to FcRn has also been isolated from rat yolk sac (Roberts et al., 1993). These data, together with in vivo studies disclosed herein strongly suggest that maternal-fetal and intestinal transport are carried out by FcRn, although the cellular location for IgG binding to FcRn appears to differ in the two processes (Roberts et al., 1993). In rats, the yolk sac FcR is located in vesicles in the apical and basolateral cytoplasm, and not on the lumenal surface of the yolk sac endodermal cells (Roberts et al., 1993). The difference in location is believed to be necessary because the pH of the lumen surrounding the yolk sac is slightly basic (Roberts et al., 1993), and the affinity of binding of FcRn to IgG is low at this pH (Hobbs et al., 1987; Rodewald and Kraehenbuhl, 1984); thus, it has been suggested that maternal IgG is taken up by the yolk sac cells in a non-specific endocytotic step and then binds to FcRn in a slightly acidic endosomal compartment. Delivery of IgG into the fetal circulation is then proposed to occur in a similar way to that of intestinal transcytosis (Roberts et al., 1993). Similarly, with respect to the control of IgG catabolism, IgGs may be taken up by the 'catabolic' cells in a non-specific endocytotic step and subsequently bind to FcRn in an endosomal compartment.

Interrelationship Between IgG Transcytosis and Control of Catabolism

Data (Kim et al., 1994a; Kim et al., 1994b) suggest that, as originally proposed by Brambell and colleagues (1966;

Brambell, 1966), the Fc receptors involved in catabolism control, maternal-fetal transfer and intestinal transfer bind to the same site of murine IgG1 and are closely related, if not the same. In support of this hypothesis, expression analysis indicates that, in addition to high level expression of FcRn in murine yolk sac and neonatal intestine, FcRn is ubiquitously expressed at lower levels in murine heart, lung, liver, spleen and endothelial cells lines but not in T nor B lymphocytes.

It is expected that maternal transfer of passive immunity to infants will be improved if the affinity of the Fc:FcRn interaction is increased and serum persistence is lengthened. For enhanced serum persistence and maternal-fetal transfer of a therapeutic IgG, it is preferable to endow that IgG with a higher affinity for binding to the Fc receptors that are involved in the processes. As a result, the higher affinity IgGs should be able to out-compete the high concentrations of endogeneous IgGs (5 mg/ml in mice and 10 mg/ml in humans).

D: Engineered Antibody Domains with Extended In Vivo Half Lives

The mechanisms involved in regulating the in vivo catabolism of IgG molecules are currently not well understood, although the Fc region is believed to contain sequences that are important for serum persistence of IgG (Spiegelberg and Weigle, 1965). As described herein and by Pollock et al. (1990), the CH2 domain and the CH3 domain have been shown to influence biological half life of IgGs.

It has been observed that Staphylococcal protein A (SpA)-IgG complexes are cleared more rapidly from serum than uncomplexed IgG molecules (Dima et al., 1983). Results from X-ray crystallography studies have indicated that residues in the Fc-hinge region are involved in SpA binding (Deisenhofer, 1981). These distinct lines of information prompted the present inventors to mutate residues at the CH2–CH3 domain interface of the (above-described) recombinant Fc-hinge fragment derived from the murine IgG1 molecule and to investigate the catabolism of the resultant mutants.

Using this approach, several amino acid residues of the CH2 domain, Ile-253 and His-310 (and double mutation of His310, Gln-311 to Ala310, Asn311), and of the CH3 domain (the double mutation of His-433-Asn-434, single muations of His433 and Asn434, and the single mutations of His 435 and His 436) were changed by in vitro mutagenesis. The mutant proteins were then purified from recombinant *E. coli* cells and the pharmacokinetic parameters measured in mice. The results from such studies demonstrate that amino acid residues from the CH2 domain, and those from the CH3 domain, are directly involved in the catabolism of mouse IgG1. Thus, the site of the IgG1 molecule that controls catabolism is located at the CH2–CH3 domain interface and is distinct from the lower hinge region that is involved in binding to Fc receptors (Duncan et al., 1988; Lund et al., 1991). The identification of specific amino acid residues that are involved in catabolism control supports the hypothesis that receptor bearing cells may be important in regulating serum IgG levels (Brambell et al., 1964).

The inventors have termed the specific residues of the murine IgG1 molecule that they discovered to be involved in controlling the catabolism of this isotype the 'catabolic control site'. This region is distinct from the sites of interaction with classical Fc receptors (FcγRI, FcγRII, and FcγRIII) but overlaps with the SpA binding site. This is, therefore, consistent with earlier data that showed that SpA-immunoglobulin complexes were cleared more rapidly than uncomplexed immunoglobulins (Dima et al., 1983). This data does not rule out the involvement of additional residues of the Fc fragment in catabolism control, but it does provide a clear means by which the biological half life of an antibody or antibody-based molecule or conjugate may be shortened. It also provides a means by which the longevity of a particular antibody may be increased if desired, by re-inserting residues such as ile253, his310, his435 and his436, should any such residues be found to be different in a particular antibody, e.g. IgG2b. Also random mutagenesis of residues flanking these key amino acids, followed by selection, may yield an Fc fragment with increased half life.

Although the mechanisms involved in the catabolism of IgG molecules have still to be completely elucidated, the data presented herein support the concept that SpA-like 'protective' receptors bind to the CH2–CH3 domain interface on IgGs and protect them from degradation. The engineered Fc-hinge fragments which form these aspects of the present invention are envisioned to be useful reagents in a variety of embodiments. For example, they may be employed in the isolation the putative receptor, which is most likely FcRn, and in further delineating the sites and mechanism of IgG catabolism.

The recombinant Fc-hinge fragments may also be useful for the preparation and delivery of immunotoxins where it is desirable to modulate the persistence of an immunotoxin in an animal. Immunotoxins are agents which have an antibody component linked to another agent, particularly a cytotoxic or otherwise anticellular agent, having the ability to kill or suppress the growth or cell division of cells. The preparation of immunotoxins is generally well known in the art (see, e.g., U.S. Pat. No. 4,340,535, incorporated herein by reference).

E: FcRn

Despite the central role that gamma-globulin (IgG) plays in immunity, little is known about the molecular mechanisms and dynamics by which remarkably constant IgG levels are maintained in the serum. Understanding the processes that maintain IgG homeostasis at the molecular level is of relevance to the treatment of IgG deficiencies and the effective delivery of therapeutic antibodies. Functional studies in neonatal mice indicate that the same amino acids of murine IgG1 (mIgG1) that regulate IgG catabolism, Fc residues Ile253, His310, His433, Asn434, His435 and His 436, where His433 and Asn434 are a double mutation, are also involved in binding to the MHC Class I homologue, FcRn, and this is consistent with the X-ray crystallographic structure of a rat FcRn: Fc complex (Burmeister et al., 1994a, b). Rodent FcRn has been implicated in passive transfer of IgGs from mother to young primarily via neonatal transcytosis (Rodewald and Kraehenbuhl, 1984; Simister and Rees, 1985), and comprises a 45–50 kDa α-chain associated with β2-microglobulin (β2m; Simister and Mostov, 1989b). The effects of mutation of Ile253, His310, His433, Asn434, His435 and His436 on the B physiological half life of recombinant Fc-hinge fragments and on neonatal transcytosis correlate closely. This suggests that FcRn, or a closely related protein, might be the as yet unidentified Fc receptor that was originally suggested by Brambell and colleagues to be involved in regulating serum IgG levels (Brambell et al., 1964). Such Fc receptors were proposed to maintain IgG homeostasis by binding and releasing IgGs back into the circulation and when IgG reaches saturating concentrations for the receptors, excess IgG is destined for degradation (Brambell et al., 1964).

The catabolism of IgG is a diffuse process occurring not only in specific organs such as liver (Fukumoto and Brandon, 1979) and intestine (Covell et al., 1986), but also in tissues containing reticulo-endothelial components such as spleen, skin and muscle (Mariani and Strober, 1990). Paradoxically, these cells may also bear the putative Fc receptors that recycle IgGs (Brambell et al., 1964). The ubiquitous expression of rat FcRn (Simister and Mostov, 1989a) and a human FcRn homologue (Story et al., 1994) outside the cells involved in maternofetal/neonatal transfer of IgGs would be consistent with a role in controlling IgG levels at sites throughout the body.

As described in Example 7, the expression of FcRn in mouse tissues and cell lines has been analyzed using reverse transcriptase (RT)-PCR™. FcRn α-chain mRNA is ubiquitously distributed in adult tissues/cell types, particularly those that are rich in endothelial cells. The pharmacokinetics of Fc-hinge fragments in genetically manipulated mice that lack FcRn expression (Zijlstra et al., 1990; Koller et al., 1990) due to disruption of the β2m gene (β2m-/- mice) have also been analyzed. The data support the involvement of FcRn in regulating IgG catabolism.

In the study described in Example 7, the analysis of the pharmacokinetics of IgG1/Fc fragments in β2m-/- mice provides evidence in support of the concept that the β2 m dependent protein (Zijlstra et al., 1990), FcRn, might be involved in maintaining serum IgG levels. The suggested implication of FcRn in this role is consistent with the ubiquitous expression of FcRn or its homologue in rats (Simister and Mostov, 1989a), man (Story et al., 1994) and mice (FIG. 4A–FIG. 4C) and, in addition, the close overlap between the region of IgG involved in controlling neonatal transcytosis, IgG catabolism and binding to recombinant FcRn (Kim et al., 1994b; Popov et al., 1996; Medesan et al., 1997).

RT-PCR™ analyses demonstrate that FcRn is expressed in liver, spleen and lung, but not in clonal B and T cell lines/hybridomas. Further analyses of expression in both mouse endothelial cell lines and hepatocytes indicated that FcRn is also expressed in these cell types. Quantitative PCR™ indicates that the level of expression in these cells is substantially lower than that in neonatal brush border, and this may account for the lack of detection of mouse FcRn α-chain mRNA in tissues other than neonatal brush border and yolk sac that was previously reported using Northern blotting (Ahouse et al., 1993). Direct binding studies with the endothelial cell line SVEC indicate that WT Fc-hinge binds at significantly higher levels than the HQ-310/HN-433 mutant. Earlier observations demonstrating that the mutant Fc-hinge fragment binds at background levels to isolated neonatal brush border (Kim et al., 1994b) and undetectably to recombinant FcRn (Popov et al., 1996), suggest that the differential binding is mediated by FcRn. The possibility that the differential binding is due to interaction with FcgRI, II and/or III is made unlikely by reports which demonstrate that the interaction site of these receptors on Fc is distal to the CH2–CH3 domain interface (Duncan et al., 1988; Canfield and Morrison, 1991; Lund et al., 1991) and, furthermore, that aglycosylated Fc fragments are impaired in binding to these receptors (Tao and Morrison, 1989; Nose et al., 1990). The binding data therefore suggest that FcRn is functional in SVEC cells, and is contemplated to be functional in the other cell types in which FcRn α-chain mRNA is expressed. Functional FcRn has also been isolated from SVEC cell lysates using murine IgG1 (mIgG1) coupled to Sepharose.

The functional significance of the expression of FcRn in both endothelial cells and hepatocytes suggests that either or both of these cell types might be involved in maintaining IgG homeostasis. In this respect, FcRn has been detected by immunoprecipitation from rat hepatocytes, and a role in mediating the trafficking of IgG into the biliary tract has recently been suggested to be of relevance for immunosurveillance at this site (Blumberg et al., 1995). A distinct function for hepatocytic FcRn, however, might be that this protein sequesters bound IgGs from delivery into the bile and only unbound (excess) IgG is delivered for catabolism in the biliary tract. This is consistent with data indicating that IgG is delivered via liver cells into the bile for breakdown in sheep (Fukumoto and Brandon, 1979). Taken together with the earlier data of others (reviewed in Mariani and Strober, 1990; Zuckier et al., 1989), however, the findings in this study support the involvement of both the liver and the more diffusely located endothelial cells.

The pharmacokinetic data demonstrate that mIgG1 or WT Fc-hinge have abnormally short serum half lives in β2m-/- mice. These serum half lives are not due to some generalized defect in the maintenance of serum Ig levels, as the serum half life of IgA is the same in both β2m+/+ and β2m-/- mice. Many studies have indicated that there is an inverse correlation between serum IgG concentrations and half lives of IgG and this is called the concentration-catabolism phenomenon (Waldmann and Strober, 1969; Zuckier et al., 1989). The rapid elimination of mIgG1/WT Fc-hinge might therefore be due to abnormally high levels of endogenous serum IgGs in β2m-/- mice.

This is clearly not the case, however, as serum IgG levels are abnormally low in β2m-/- mice of both backgrounds, and these low serum IgG concentrations are consistent with the observations of others (Spriggs et al., 1992; Israel et al., 1995). In contrast, the serum IgA and IgM concentrations, which are regulated by a mechanism distinct from that involved in IgG homeostasis (Strober et al., 1968), are in the normal range.

To date, the role that IgG breakdown rates might have in mediating the low serum IgG concentrations in β2m-/- mice has not been investigated. It has previously been suggested that in normal mice, maternal IgG stimulates endogenous immunoglobulin synthesis, and lack of maternal transfer in β2m-/- mice accounts for the low IgG levels (Israel et al., 1995). However, the data in this study show that although β2m-/- mice of both backgrounds have lower IgG1 synthesis rates, an additional cause of the low serum IgG levels is an increase in catabolic rates. The situation for mice of the C57BL/6×129/Ola background is made more complex by the observation that even for β2m+/+ animals of this background, IgG and IgG1 levels are abnormally low. This is due to a synthesis rate that, unexpectedly, is lower than that for β2m-/- mice of this mixed background. Thus, independently of the presence or absence of neonatal transfer of IgGs in mice of the mixed background, the IgG1 synthesis rate is abnormally low and the reasons for this are unknown. As a consequence of the low serum IgG concentrations in β2m+/+ mice of this background, and consistent with the concentration-catabolism phenomenon (Waldmann and Strober, 1969; Zuckier et al., 1989), the half lives of mIgG1 and WT Fc-hinge are significantly longer in this strain than in β2m+/+ C57BL/6 mice.

The observations in β2m-/- mice are consistent with a model whereby β2m dependent Fc receptors, i.e. FcRn, which in normal mice regulate serum IgG levels, are either absent or dysfunctional in β2m-/- mice. However, alternative explanations cannot be excluded, particularly if loss of β2m is more pleiotropic than the currently available data indicate. This is made improbable by the presence of an apparently normal CD4+CD8- subset (Zijlstra et al., 1990; Koller et al., 1990) and the ability of B cells to mount T cell dependent antibody responses (Spriggs et al., 1992; Mozes et al., 1993) in β2m−/− mice. Other possibilities, such as either a deficiency in IgG-producing precursor cells or the absence of factors/cytokines produced by CD8+cells resulting in the low serum IgG levels are excluded by the observations that β2m−/− mice have normal numbers of B220+/sIgM cells (Spriggs et al., 1992) and, in Lyt2 knockout mice, lack of CD8+ cells does not result in reduced IgG levels (Fung-Leung et al., 1991). In addition, the possibility that a β2m dependent protein similar to FcRn, rather than FcRn itself, is involved in IgG homeostasis is made unlikely by Southern blotting data indicating that in mice FcRn has no close homologue (Kandil et al., 1995). However, it is conceivable that an unrelated, as yet unidentified, β2m dependent protein that binds to Fc or IgG at the same site as FcRn plays a role in maintaining serum IgG levels.

The ability of FcRn to bind and mediate the traffic of IgGs across neonatal intestinal and yolk sac cells suggests a mechanism by which FcRn in other tissues might protect IgGs against degradation by binding and recirculating it into the serum. Constant levels of FcRn expression would explain how IgG homeostasis is maintained despite variable IgG production by B cells, as once FcRn is saturated, excess IgG would be destined for degradation following endocytotic uptake (Brambell et al., 1964). Concerning the site of FcRn-IgG complex formation, the pH dependence of this interaction (Rodewald and Kraehenbuhl, 1984; Simister and Rees, 1985; Gastinel et al., 1992) suggests that for the maintenance of serum IgG levels, FcRn would bind to IgG following uptake by fluid phase endocytosis into intracellular, acidic compartments. This is in contrast to the FcRn-Fc interaction that occurs in the slightly acidic medium at the apical cell surface of jejunal epithelial cells during transcytosis across the neonatal intestine (Rodewald, 1973), but data in support of a similar mechanism for the maternofetal transfer of IgGs in both humans (Leach et al., 1990) and rats (Roberts et al., 1990) has been reported.

In summary, the findings suggest a new role for FcRn that is distinct from previously assigned functions (Rodewald and Kraehenbuhl, 1984; Simister and Rees, 1985), and this has relevance to understanding the molecular mechanisms that maintain IgG homeostasis. The sequence similarities between rodent FcRn and a recently identified human FcR (Story et al., 1994) suggest that the present discovery will have implications for the therapy of IgG-related immunodeficiencies in humans and also for mediating maternal-fetal transfer of therapeutic IgGs across the human placenta.

F: Mutagenesis

In the present invention the mutagenesis of amino acid residues can either be random or site-specific. One may choose to make completely random mutations in the protein or alternatively to only randomly mutate certain residues as described in Example 4. One could also change a residue to any other amino acid residue; however, it is likely that certain residues would be preferred. For example, mutating hydrophilic residues that are essential to maintain the tertiary, or three-dimensional, structure of the protein to large hydrophobic residues would probably not be desirable since such mutations may destabilize the antibody and not extend the half life of the molecule. In addition, it would be preferred to mutate exposed residues as they are most likely to interact with FcRn.

Site-specific mutagenesis is a technique useful in the preparation of individual proteins or peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art. As will be appreciated, the technique typically employs a bacteriophage vector that exists in both a single stranded and double stranded form. Typical vectors useful in site-directed mutagenesis include vectors such as the M13 phage or phagmid vectors such as pUC119. These phage vectors are commercially available and their use is generally well known to those skilled in the art. Double stranded plasmids are also routinely employed in site directed mutagenesis, using the PCR™, which eliminates the step of generating single stranded DNA.

In general, site-directed mutagenesis is performed by first obtaining a single-stranded vector, or melting of two strands of a double stranded vector which includes within its sequence a DNA sequence encoding the desired protein. An oligonucleotide primer bearing the desired mutated sequence is synthetically prepared. This primer is then annealed with the single-stranded DNA preparation, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected that include recombinant vectors bearing the mutated sequence arrangement.

Alternatively, PCR™ directed mutagenesis of double-stranded DNA can be used by designing oligonucleotide primers that overlap the site to be mutated. Such mutants may be readily prepared by, for example, directly synthesizing the Fc fragment by application of nucleic acid reproduction technology, such as the PCR™ technology of U.S. Pat. No. 4,603,102 (incorporated herein by reference).

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

G: Vaccines

The present invention contemplates vaccines for use in both active and passive immunization embodiments. Immunogenic compositions, proposed to be suitable for use as a vaccine, may be prepared most readily directly from engineered antibody Fc fragments, domains and/or peptides prepared in a manner disclosed herein. Preferably the antigenic material is extensively dialyzed to remove undesired small molecular weight molecules and/or lyophilized for more ready formulation into a desired vehicle.

The preparation of vaccines which contain peptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables. Either as liquid solutions or suspensions: solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants which enhance the effectiveness of the vaccines.

Vaccines may be conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides: such suppositories may be formed from mixtures containing the active ingredient in the range of 0.5% to 10%, preferably 1–2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain 10–95% of active ingredient, preferably 25–70%.

The proteins may be formulated into the vaccine as neutral or salt forms. Pharmaceutically acceptable salts, include the acid addition salts (formed with the free amino groups of the peptide) and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, including, e.g., the capacity of the individual's immune system to synthesize antibodies, and the degree of protection desired. Precise amounts of active ingredient required to be administered depend on the judgment of the practitioner. However, suitable dosage ranges are of the order of several hundred micrograms active ingredient per vaccination. Suitable regimes for initial administration and booster shots are also variable, but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the size of the host.

Various methods of achieving adjuvant effect for the vaccine includes use of agents such as aluminum hydroxide or phosphate (alum), commonly used as 0.05 to 0.1 percent solution in phosphate buffered saline, admixture with synthetic polymers of sugars (Carbopol) used as 0.25 percent solution, aggregation of the protein in the vaccine by heat treatment with temperatures ranging between 70° to 101° C. for 30 second to 2 minute periods respectively. Aggregation by reactivating with pepsin treated (Fab) antibodies to albumin, mixture with bacterial cells such as $C.\ parvum$ or endotoxins or lipopolysaccharide components of gram-negative bacteria, emulsion in physiologically acceptable oil vehicles such as mannide mono-oleate (Aracel A) or emulsion with 20 percent solution of a perfluorocarbon (Fluosol-DA) used as a block substitute may also be employed In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1–5 years, usually three years, will be desirable to maintain protective levels of the antibodies. The course of the immunization may be followed by assays for antibodies for the supernatant antigens. The assays may be performed by labeling with conventional labels, such as radionuclides, enzymes, fluorescers, and the like. These techniques are well known and may be found in a wide variety of patents, such as U.S. Pat. Nos. 3,791,932; 4,174,384 and 3,949,064, as illustrative of these types of assays.

The following examples are intended to illustrate the practice of the present invention and are not intended to be limiting. As the invention is demonstrated with a variety of immunoglobulin-like domains, including murine antibody Fc-hinge, Fc, CH2-hinge and CH3 domains; and mutant domains with increased stability; it will be understood that other proteins or peptides will be adaptable to similar constructs as those described herein. Likewise, a variety of tags, linker sequences and leader sequences may be employed depending on the particular purification or isolation methods desired to obtain the polypeptide products.

EXAMPLE 1

The following example illustrates the production of an immunoglobulin Fc-hinge or Fc fragment and Fc-hinge or Fc derived subfragments in milligram quantities using $E.\ coli$ as an expression host. These results indicate the suitability of the system for the commercial production of large quantities of recombinant protein.

Plasmids, Expression and Purification

Figure 1:
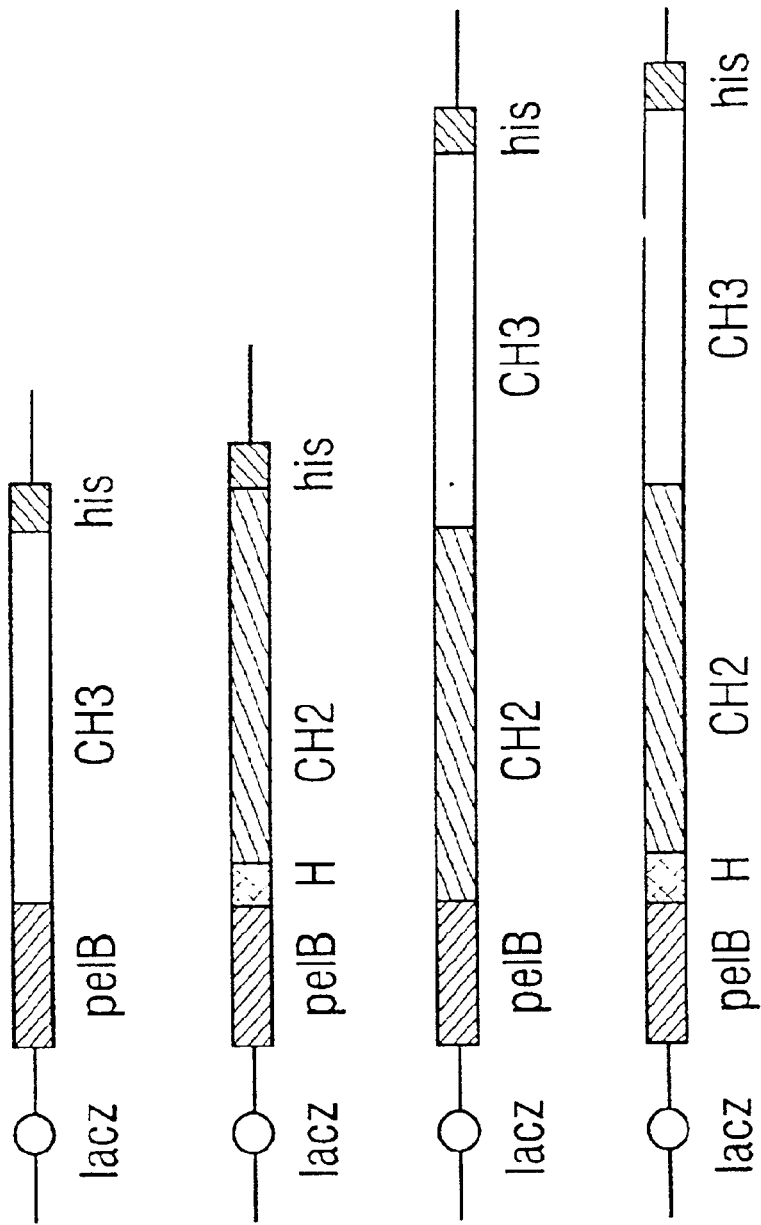
FIG. 1. Schematic representation of portions of the plasmids used for the expression and secretion of immunoglobulin constant region fragments in $E. \ coli$. a) CH3 domain; b) CH2-hinge; c) Fc fragment and d) Fc-hinge fragments. The lacz promoter is represented by open circles, the pelB leader by hatched boxes, the immunoglobulin domains [hinge region (H) and CH2, CH3 domains] by open boxes and the his$_6$ peptide tag (his) by filled-in boxes.

PCR™ was used to isolate and tailor the genes encoding fragments derived from the murine IgG1 immunoglobulin molecule 9E10 (Honjo et al., 1979; Evan et al., 1985) for ligation into the expression plasmids (FIG. 1). To accomplish this, total RNA was extracted from 1×10$^7$ 9E10 hybridoma cells, as described herein above. cDNA was primed using oligonucleotides CH3forBst or CH2forBst (see below; Honjo et al., 1979) for the isolation of either the CH3 domain gene/Fc fragment genes or the CH2 domain gene respectively. The genes were then isolated using PCR™ and the primers shown below. As listed, the five distinct sequences represent SEQ ID NO:1 through SEQ ID NO:5, respectively.

a) CH3 domain,
CH3bakNco=5' ATC A<u>CC ATG GCC</u> GGC AGA CCG AAG GCT CCA CAG 3';
CH3forBst=5' TAC <u>AGG TGA CCT</u> TAC CAG GAG AGT GGG AGA GGC T 3' b) CH2-hinge,
HingebakNco=5' ATC ACC ATG GCC GTG CCC AGG GAT TGT GGT TG 3'
CH2forBst=5' ATC AGG TGA CCT TGG TTT TGG AGA TGG TTT T 3'
c) Fc fragment,
CH2bakNco=5' ATC ACC ATG GCC GAA GTA TCA TCT GTC TTC ATC 3'
CH3forBst; as above
d) Fc-hinge fragment,
HingebakNco and CH3forBst; both as above A typical PCR™ comprised: 3 units Promega Taq polymerase, 10 µl Promega buffer, 10 ml 0.2 mM dNTP cDNA synthesis reaction in a final volume of 100 ml. Cycling conditions were: 94° C. (0.5 min), 55° C. (0.5 min), 72° C. (1 min) for thirty cycle using a Techne temperature cycling block. The oligonucleotides each encode either an NcoI or BstEII restriction site indicated by underlining, and italicized sequences) indicate the regions of the oligonucleotides that anneal to murine IgG1 constant region genes (Honjo et al., 1979); which allows restriction digestion of the PCR™ products followed by gel purification and ligation as NcoI-BstEII fragments into Vape 1βHis (Ward, 1992). The ligated DNA was then transformed into E. coli BMH 71–18, as described above. The sequences of the inserts of all plasmid constructions were analyzed using the dideoxynucleotide method and either Sequenase (USB) for single stranded DNA templates and Femtomole kits (Promega) for double stranded DNA templates.

These antibody fragments can be expressed and secreted from recombinant E. coli cells, and the carboxy-terminal His$_6$ peptide tags allow purification using Ni$^{2+}$-NTA-agarose. E. coli BMH 71-18 transformants harboring the plasmids shown in FIG. 1 were grown up and induced for expression as described herein above. The recombinant proteins were isolated from the periplasm by osmotic shock followed by affinity purification using Ni$^{2+}$-NTA-agarose. The recombinant fragments were purified in yields of 2, 1–1.5, 1.5–2 and 0.5–1 milligrams per liter of culture for the CH3 domain, CH2-hinge fragment, Fc fragment and Fc-hinge fragment respectively. The purity of the recombinant proteins was assessed using SDS gel electrophoresis (Laemmli) and staining with Coomassie blue R-250.

CH2-hinge fragments were expressed as a mixture of dimers and monomers. dimers were separated from monomers using a Sepharose-G75 column (Pharmacia, Piscataway, N.J.). Monomeric CH2-hinge fragments were prepared from dimers by reduction (using dithiothreitol) followed by treatment (blockade) of reduced sulfhydryl groups with iodoacetamide as described (Kim et al., 1994c).

In Vitro Analyses

Results from HPLC analyses indicated that the CH3 domain, Fc fragment and FEc-hinge fragment are all expressed and purified as homodimeric proteins. For the Fc and CH3 domain, the dimers are non-covalently linked, as demonstrated by analyses on non-reducing PAGE (FIG. 2B). The dimerization of the Fc fragments and CH3 domains is presumably stabilized by non-covalent interactions between the CH3 fragments, which are closely apposed in the immunoglobulin structure (Marquart et al., 1980). For the Fc-hinge dimer, the fragments are also covalently linked by —S—S— bridges between the hinge region cysteines.

In contrast, analysis of the CH2-hinge fragment using HPLC indicates that approximately 10% of the protein is expressed and purified as a dimer, and the remainder as monomers. Structural analyses of immunoglobulins indicate that the CH2 domains in the Fc region of an antibody molecule form few interactions, and presumably the relative weakness of these interactions (compared with those between CH3 domain, for example) result in a low proportion of expressed dimers. The dimers are covalently linked by —S—S— bridges; expression and purification of CH2 domain without the hinge region resulted in a significant proportion of this protein forming dimers that are non-covalently linked, and in addition, there are no free sulphydryls as would be expected for an immunoglobulin domain that is correctly folded with intramolecular —S—S— bridges. This suggests that in the CH2-hinge fragments, the —S—S— bridges are formed between cysteine residues located in the hinge region.

EXAMPLE 2

The following example illustrates that the native sequence immunoglobulin Fe-hinge and Fc fragments, purified following expression in E. Coli, have similar in vivo stability to the native IgG1 antibody molecule.

To determine the clearance rates of the immunoglobulin fragments in vivo, the recombinant proteins were radiolabeled with $^{125}$I and the levels of serum radiolabel monitored as a function of time. The clearance rates were then compared with those of intact murine IgG1 (expressed and purified from a hybridoma) and the bacterially expressed D1.3 Fv fragment (Ward et al., 1989) derived from the murine D1.3 antibody. The clearance curves were all found to be biphasic (FIG. 2A and FIG. 2B). The half lives of the α and β phases are shown in Table II. For the D 1.3 Fv, monomeric CH2-hinge and CH3 fragments the α phases were too rapid to be accurately determined (FIG. 2A and FIG. 2B).

From the clearance rate data, several conclusions can be drawn. Firstly, the recombinant aglycosylated Fc-hinge fragment has the same stability in vivo as the complete glycosylated IgG1 molecule. The shorter half life of the a phase, which represents the equilibration phase between the vascular and extravascular tissue, is shorter for the recombinant Fc-hinge fragment due to its smaller size. Secondly, both the CH3 domain and monomeric CH2-hinge fragment are cleared at rates similar to that of the D1.3 Fv fragment (FIG. 2A and FIG. 2B).

TABLE II

Half Lives of the β Phases of the Immunoglobulin Fragments

| Immunoglobulin (fragment) | β-phase (half life in hours) |
| --- | --- |
| CH2 + Hinge | 29.1 ± 1.2 |
| [CH2 + Hinge]$_2$ | 61.6 ± 10.7 |
| CH3 | 21.3 ± 2.3 |
| Fv | 24.1 ± 3.5 |
| Fc-hinge | 82.9 ± 10.0 |
| Complete immunoglobulin (IgG1) | 89.2 ± 10.6 |

Recombinant immunoglobulin fragments were purified and radiolabeled using either the Bolton Hunter reagent (Amersham, 2000 Ci/mmol) or Iodogen (Amersham) to a specific activity of $10^5$–$10^7$ cpm/mg of protein. The complete IgG1 antibody used as a control was purified from mammalian cells using standard methodology. The glycosylated Fc-hinge fragment was derived from this IgG1 antibody by papain digestion followed by purification using protein A sepharose (Pierce). For the measurement of the half lives, 2–4 BALB/c mice (23–28 gnis, female) were injected with 0.1 ml of radiolabeled protein (approximately 1–50 µg protein containing $10^6$–$10^7$ cpm) in the tail or retro-orbitally, and bled retro-orbitally at time points from 2 mins-72 hours post injection. The amount of radioactivity present in the blood samples was determined using a Scintillation counter.

A high proportion (approximately 90%) of the CH2-hinge fragment was expressed and purified in monomeric rather than dimeric form, and therefore the possibility remained that the determinants of stability are located on the CH2-hinge dimer. To determine whether CH2-hinge dimers were stable in vivo, dimers of the CH2-hinge fragments were separated from monomers by size exclusion and radiolabeled for use in pharmacokinetic studies as described by Kim et al. (1994c); monomers of CH2-hinge dimers were generated from the dimers by reduction and alkylations and these monomers were also radiolabeled and used in pharmacokinetic studies. The half life of the β phase of this dimer is significantly longer than that of the predominantly monomeric CH2-hinge domain.

These data demonstrate that recombinant aglycosylated Fc-hinge fragment has a β phase that is similar to that of a complete glycosylated IgG1 immunoglobulin molecule. Therefore, the carbohydrate residues do not appear to play a major role in stability. In addition (Kim et al., 1995) the presence of the hinge results in a slight increase in the half life. In contrast, both monomeric CH2-hinge and CH3 fragments are catabolized as rapidly as antibody Fv fragments, indicating that the presence of sequences in both the CH2 and CH3 domains are necessary for the in vivo stability of the recombinant Fc-hinge or Fc fragment. However, a CH2-hinge dimer has a longer half life than a CH2-hinge monomer, but consistent with the need for a CH3 domain the CH2-hinge dimer half life is less than that of Fc-hinge. The production of the IgG1 Fc-hinge or Fc fragment in E. coli is envisioned to allow the delineation of the key residues involved in controlling the catabolism of the immunoglobulin molecule in vivo. In light of the present work, the production and analysis of human Fc regions in E. coli is now possible. It is envisioned that this work will also lead to the development of novel tagging and stabilization methods for use with various recombinant molecules employed in animal or human therapeutics.

EXAMPLE 3

The following example illustrates the abnormally short half lives of IgGs in β2-microglobulin deficient mice, and demonstrates the expression of FcRn α-chain in adult liver, lung, spleen and endothelial cells, with implications for a role for FcRn in the maintenance of serum IgG levels.
Cell Lines The mouse B cell line BCL1/3B3 (Brooks et al., 1983) and T cell hybridoma 2B4 (Chien et al., 1984) were used in this study. The two endothelial cell lines, mouse pulmonary capillary endothelial cells (B10, D2.PCE) and SV40 transformed endothelial cells (Kim et al., 1994c) (SVEC) were derived from lungs of B10. DBA/2 mice and C3H/HeJ mice, respectively. The B10, D2.PCE cell line was obtained from Prof. A. Curtis. The murine hepatoma line, Hepa 1–6, was obtained from the ATCC (1830-CRL).
Mice Strains β2m−/− (Koller et al., 1990; C57BL/6×129/Ola and C57BL/6 background; for the mixed background, 129/Ola mice have been backcrossed at least 2–3 times onto a C57BL/6 background and the colony maintained by littermate crosses) and β2m+/+ [(C57BL/6×129/Ola)F2] mice were from Jackson Laboratories. β2m+/+ (C57BL/6) mice were from the Southwestern Medical Center Animal Resources Center.

RT-PCR™ Analyses

Lung, liver, hepatocytes, spleen and yolk sac were isolated from adult BALB/c mice and neonatal brush border from 12 day old BALB/c mice. For the isolation of hepatocytes, a method described previously for the isolation of rat hepatocytes was used (Quistorff et al., 1993). This resulted in a population of cells that was greater than 95% hepatocytes. RNA was extracted from tissues/cell lines and cDNA synthesis primed with primer B; complementary to bases 1075–1095 of the coding strand of the FcRn α-chain (Ahouse et al., 1993) with 13 bases appended to 'add-on' a restriction site using previously described methods (Kim et al., 1994a). Aliquots of the cDNA syntheses were used in the PCR™ with either primers A (SEQ ID NO:6) and B or primers B and C. Primer A (SEQ ID NO:6) and C match bases 640–656 and 964–996 of the coding strand of the FcRn α-chain gene (Ahouse et al., 1993), respectively. Primer C has 12 bases appended to 'add-on' a restriction site. The expected sizes of the RT-PCR™ products are 469 bp (primers A (SEQ ID NO:6) and B) and 157 bp (primers B and C).

As controls for the RT-PCRs™, β-actin primers (bases 352–368 of the mouse β-actin coding sequence and complementary to bases 781–787 of the β-actin coding sequence) were used in cDNA syntheses and PCRs™. Southern blotting (Sambrook et al., 1989) was carried out using a $^{32}$P-labeled SacI-BstEII fragment derived from the cloned FcRn α-chain (bases 688–1028) as probe.
Isolation and Nucleotide Sequencing of the Complete FcRn α-chain Gene from Endothelial Cells The gene encoding the entire FcRn α-chain was isolated as two overlapping clones, as follows. Total RNA was isolated from endothelial cell lines and the gene segment encoding the extracellular domains (including leader peptide) was isolated by RT-PCR™ using primers that matched bases 1–24 and were complementary to bases 841–870 of the coding sequence of FcRn (Ahouse et al., 1993). This gene, derived from D10, D2.PCE cells, has been used to construct a plasmid for the expression of soluble FcRn in insect cells (Popov et al., 1996). The segment encoding bases 640–1095 (including the transmembrane region and cytoplasmic tail) was isolated using RT-PCR™ and primers A (SEQ ID NO:6) and B. PCR™ products were cloned into pGEM-T (Promega) and then recloned as SphI-SalI fragments in both orientations into pUC118/pUC119. ssDNA was isolated from resulting clones and sequenced using the dideoxynucleotide method (Sanger et al., 1977) and Sequenase® (USB Biochemicals). For each fragment, several independent PCR™ isolates were analyzed.
Quantitative PCR™

Essentially the methodology of Scheuermann and Bauer was used (Scheuermann and Bauer, 1993). A gene segment encoding the carboxyterminal region of FcRn plus the 3' untranslated region (Ahouse et al., 1993) was isolated using the PCR™ and the primers 5' TCT GGC TCC TCC GTG CT 3' (SEQ ID NO:6) (bases 640–656 of FcRn coding sequence) and 5' ATC ATC TAG ATT TTT TTG TTG GGG CCA AAT TTA TG 3', (SEQ ID NO:7) (XbaI site shown underlined, and sequence that is complementary to poly A tail and upstream region italicized). The PCR™ product was then restricted with XbaI (encoded in primer) and NcoI (internal sites in FcRn coding sequence and FcRn untranslated 3' tail) to generate an NcoI fragment (bases 992–1199) and an NcoI-XbaI fragment (bases 1200–1285). These two fragments were used with a pUC119 derivative containing sequences encoding bases 640–1095 to assemble a gene encoding bases 640–1095 of FcRn coding sequence plus 3' untranslated region i.e., bases 640–1285. This construct was restricted at a unique BstEII site (bases 1021–1027 of FcRn) and a 100 bp 'filler' fragment inserted prior to recloning into pSP64 (Promega). Poly A+ RNA was synthesized using the Riboprobe system II (Promega) and poly A+ RNA purified using oligo dT cellulose. This RNA (FcRn poly A) was used as an internal standard in the quantitative PCRs™.

Total RNA was extracted from cell lines as described previously (Kim et al., 1994a) or using RNeasy total RNA kits from Qiagen (Chatsworth, Calif.). cDNA synthesis reactions were carried out using 0.8–2.2 µg RNA (kept constant for each cell line) plus $10^5$–$10^8$ FcRn poly A molecules (varied within this range) and the poly A primer described above.

Aliquots of the cDNA syntheses were used in duplicate PCRs™ containing the following primers:
5' ATC ACC ATG GCC GGT AGG ATG CGC AGC GGT CTG CCA GCC 3', SEQ ID NO:8 (italicized bases match bases 967–990 of FcRn coding sequence) and 32-P labeled 5' ATC AGT CGA CCT TGG AAG TGG GTG GAA AGG CAT T 3', SEQ ID NO:9 (italicized bases are complementary to bases 1075–1095 of FcRn).

One tenth of each PCR™ was analyzed on 4% agarose gels. Bands corresponding to the PCR™ products were excised and cpm levels were determined by gamma counting (products derived from FcRn poly A could be distinguished from those derived from authentic FcRn transcripts due to the 100 bp size difference).

Incorporated cpm for standard and test samples were plotted against the amount of standard added and the point of intersection taken to correspond to equality of amounts of FcRn transcripts and FcRn poly A standard. As it was impossible to count single brush border cells, quantitation was expressed as number of transcripts per µg total RNA.

Radiolabeling of Immunoglobulins mIgG1, recombinant Fc-hinge fragments and IgA were iodinated using the Iodo-Gen reagent (Amersham) as described (Kim et al., 1994a).

Binding Studies of Recombinant Fc-hinge Fragments

Confluent layers of SVEC cells were incubated with 0.26 or 0.4 mg/ml of $^{125}$I-labeled WT Fc-hinge or HQ-310/HN-433 mutant overnight (16–18 hours) at 37° C., washed with medium (complete RPMI, Gibco, Grand Island, N.Y., plus 10% fetal calf serum) and detached by incubation with 5 mM $Na_2$EDTA in 50 mM phosphate buffer, pH 7.5 for 5 minutes. Cells were transferred and radioactivity per $10^7$ cells determined.

Cells were then pelleted and resuspended in 2 ml 2.5 mg/ml CHAPS, 0.1 M Tris-HCl pH 8.0 containing 0.3 mg/ml PMSF, 25 mg/ml pepstatin and 0.1 mg/ml aprotinin and incubated for 30 minutes at room temperature. The suspension was centrifuged at 12000 g for 30 minutes and amount of radioactivity in pellets and supernatants determined. Supernatant values were used to calculate the amount extracted per $10^7$ cells.

Pharmacokinetic Studies

Pharmacokinetics of iodinated mIgG1, recombinant Fc-hinge fragments and IgA were determined as described previously (Kim et al., 1994a).

Determination of Serum Ig Concentrations

The concentration of serum Igs were determined using radial immunodiffusion and Bindarid kits (The Binding site Ltd., Birmingham, UK). Precipitin ring diameters were measured electronically.

Determination of the Synthesis Rate of Murine IgG1

Synthesis rates (SRs) of IgG1 were calculated from the b-phase half lives (days) and serum concentrations (c, in mg/ml) using the equation (Mariani and Strober, 1990):

SR (mg/day/mouse)=(2.77 c)/($T_{1/2}$)
and the constant of 2.77 is derived from: (100×ln2×V)/(IV)
where V=volume of blood (taken as 2 ml for all mice) and IV=% intravascular
IgG1(taken as 50% for all mice).

FcRn α-chain mRNA Expression

Data disclosed herein suggested that FcRn might be involved in regulating serum IgG levels. As the site of IgG catabolism has not yet been unequivocally determined (Mariani and Strober, 1990), the expression of FcRn α-chain in a variety of mouse tissues and cell lines was analyzed using RT-PCRs™ and primers derived from the FcRn α-chain gene (Ahouse et al., 1993). Southern hybridization was carried out to ensure that the RT-PCRs™ were specific. In addition to yolk sac and neonatal brush border, FcRn α-chain is expressed in lung, liver and spleen, but not at detectable levels in clonal lymphocyte populations represented by the B cell line BCL1/3B3 (Brooks et al., 1983) and T cell hybridoma 2B4 (Chien et al., 1984). Confirmation of the identity of the PCR™ products was obtained by nucleotide sequencing.

The ubiquitous expression of the FcRn α-chain suggested that it might be produced in the endothelial cells within these tissues. Thus, RT-PCR™ analyses were carried out using two mouse endothelial cell lines, B10, D2.PCE and SVEC (O'Connell and Edidin, 1990), using primers specific for the FcRn α-chain (Ahouse et al., 1993). For both lines, expression of FcRn α-chain mRNA was observed. Consistent with the work of others (Ahouse et al., 1993; Kandil et al., 1995), isolation and sequencing of the gene for the complete coding sequence of FcRn α-chain from SVEC cells demonstrated it had the same sequence as that derived from C3H/HeJ mice (Kandil et al., 1995). This sequence differs from the mouse (FVB/N strain) FcRn gene originally described (A house et al., 1993) at codons 26, 52, 212, 230, 244 and 299. The changes are silent with the exception of a G to A change at codon 52 (valine to methionine). The sequence of the FcRn α-chain gene from B10, D2.PCE cells differs from that of the FVB/N strain (Ahouse et al., 1993) at codons 52, 212, 230 and 244, and shares the same sequence as that of SVEC cells at these positions. The B10, D2.PCE gene therefore represents a polymorphic variant of FcRn α-chain that has not been described previously.

The liver has been suggested to be involved in IgG catabolism (Fukmoto and Brandon, 1979; Mariani and Strober, 1990), and therefore the expression of FcRn in this organ was analyzed further. Hepatocytes were isolated from adult mice and analyzed by RT-PCR™, and this yielded a PCR™ product of the expected size. As the isolated hepatocytes were not completely homogenous (less than 5% contamination with other cells such as Kupffer cells), RNA was extracted from the mouse hepatoma line, Hepa 1–6, and used in RT-PCR™ analysis. This resulted in the isolation of a product of the expected size. The level of expression of FcRn in endothelial (SVEC, B10, D2.PCE) and Hepa 1–6 cell lines was studied using quantitative PCR™, and the FcRn α-chain expression level is approximately 1000-fold lower in SVEC, B10, D2.PCE cells and Hepa 1–6 cells than in neonatal brush border.

Binding Studies

Figure 3A:
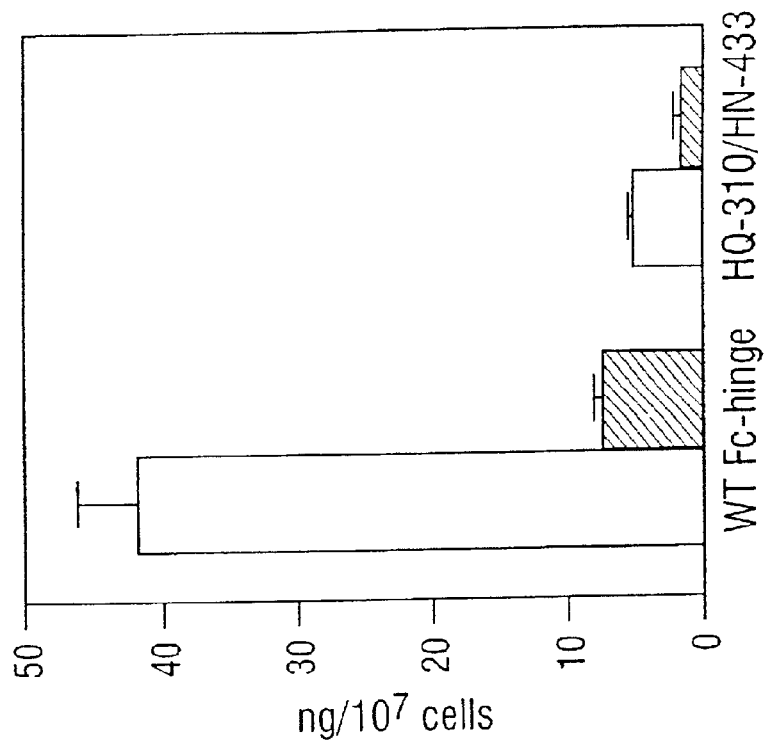
FIG. 3A. Binding of $^{125}$I-labeled WT Fc-hinge and HQ-310/HN-433 mutant to SVEC cells. Open bars represent amount bound to cells following washes, and filled-in bars represent amount extracted from cell pellet following extraction with 2.5 mg/ml CHAPS.
Figure 3B:
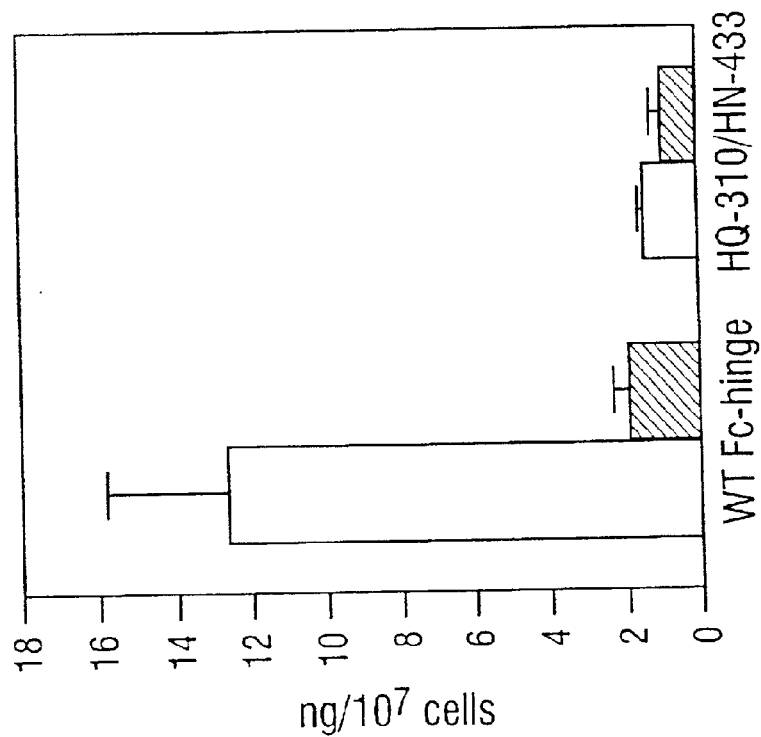
FIG. 3B. Data from repeat of study shown in FIG. 3A.

Studies were carried out to analyze the binding of wild type (WT) and the HQ-310/HN-433 mutant Fc-hinge fragments to endothelial cells. The HQ-310/HN-433 mutant was used as it binds at background levels to isolated neonatal brush border (Kim et al., 1994a) and at undetectable levels to recombinant soluble FcRn (Popov et al., 1996) due to mutation of His310, Gln311, His433, Asn434 to Ala310, Asn311, Ala433, Gln434. Binding studies with the endothelial cell line SVEC indicates that in two independent studies the WT Fc-hinge binds at much higher levels than the HQ-310/HN-433 mutant (FIG. 3A and FIG. 3B). Furthermore, a higher proportion of the bound HQ-310/HN-433 is extracted with CHAPS than for the WT Fc-hinge fragment, although this was more marked for the first study (FIG. 3A and FIG. 3B).

Pharmacokinetic Analyses in β2m−/− mice

Figure 4B:
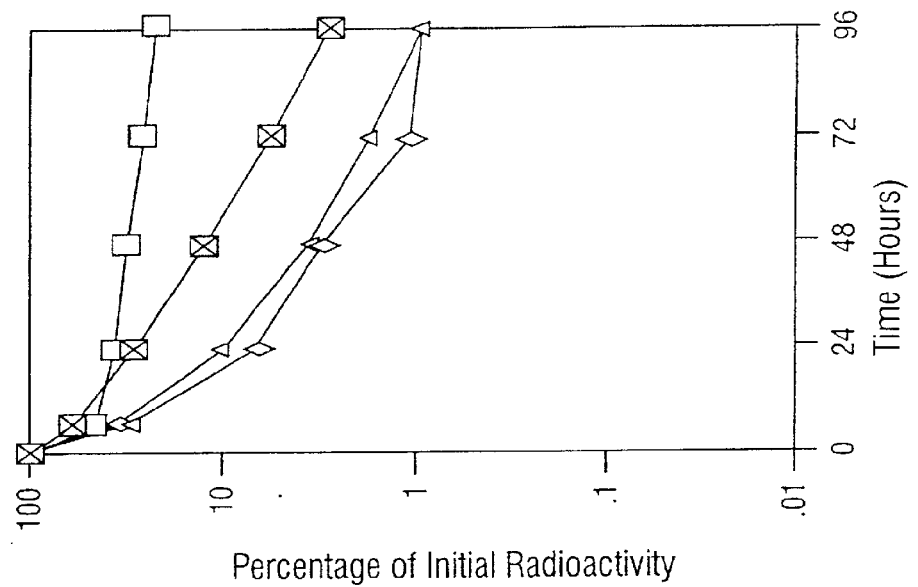
FIG. 4B. Catabolism of $^{125}$I-labeled mIgG1, Fc-hinge fragments and IgA. Open triangle and open box represent IgA; open diamond and X-ed box represents mIgG1 in β2m+/+ (open triangle and open box) and β2m−/− (open diamond and X-ed square) mice. For each protein, representative curves for one mouse from within each group are shown. These data are for mice of the C57BL/6 background.
Figure 4A:
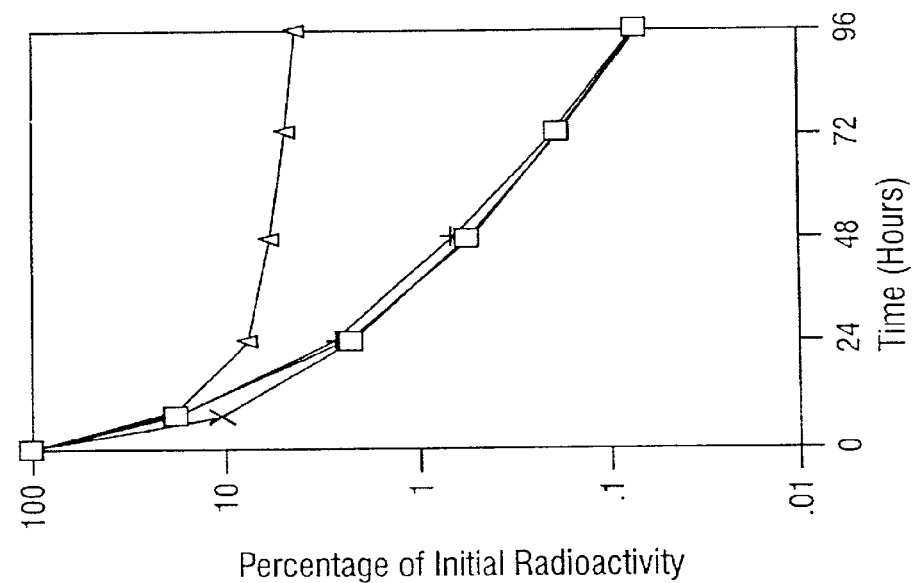
FIG. 4A. Catabolism of $^{125}$I-labeled mIgG1, Fc-hinge fragments and IgA. Closed triangle and + represent WT Fc-hinge; closed box and X represent HQ-310/HN-433 mutant in β2m+/+ (closed triangle and box) and β2m−/− (+ and X) mice.

The above data support the concept that the ubiquitously expressed FcRn might regulate serum IgG levels. β2m−/− mice are known to be deficient in the expression of Class I MHC molecules and FcRn (Zijlstra et al., 1990; Koller et al., 1990), and therefore provide a valuable tool to test this hypothesis. In earlier studies using BALB/c mice, the HQ-310/HN-433 mutant was found to have a significantly shorter β phase half life than the WT Fc-hinge fragment (Kim et al., 1994a). These two recombinant Fc-hinge fragments, in addition to mIgG1, were therefore radiolabeled and their pharmacokinetics compared in β2m−/− and β2m+/+ mice (C57BL/6×129/Ola and C57BL/6 backgrounds) (FIG. 4A and FIG. 4B; TABLE III). The β phase half lives of all three proteins in the two β2m−/− mice strains are not significantly different and are extremely short (FIG. 4A and FIG. 4B; TABLE III). In contrast, the β phase half lives of mIgG1 and WT Fc-hinge are substantially longer in β2m+/+ mice than that of the HQ-310/HN-433 mutant, consistent with earlier observations in BALB/c mice (Kim et al., 1994a). Unexpectedly, the half lives of mIgG1 and WT Fc-hinge are significantly longer in β2m+/+ (C57BL/6×129/Ola) than in β2m+/+ (C57BL/6) mice, and further analysis indicated that this is due to the abnormally low levels of serum IgGs in these mice.

ensure that β2m−/− mice do not have some generalized defect in the maintenance of Ig levels, the pharmacokinetics of murine IgA were also determined in both β2m−/− and β2m+/+ mice (FIG. 4A and FIG. 4B; TABLE III). There is no significant difference in clearance rates and the IgA β phase half lives are typical of those observed in other β2m+/+ strains (TABLE III and Waldmann and Strober, 1969; Vieira and Rajewsky, 1988).

Analysis of Serum Ig Levels

Determination of serum IgG levels in β2m−/− mice of both backgrounds indicated that they are abnormally low (TABLE IV), consistent with the observations of others (Spriggs et al., 1992; Israel et al., 1995). In addition, for β2m+/+ mice of the C57BL/6×129/Ola background, serum IgG levels are lower than those of C57BL/6 β2m+/+ mice. The concentrations of IgA and IgM have also been analyzed for both β2m+/+ and β2m−/− mice and their levels are in the normal range (Goding, 1983). Based on the pharmacokinetics and serum IgG1 concentrations, the synthetic rates of IgG1 can also be determined (TABLE V) and these data are discussed more fully below.

TABLE III

β Phase Half Lives of
Igs and Fc-Hinge Fragments in β2m−/− and β2m+/+ Mice

| | β Phase Half Life (Hours) | | | |
|---|---|---|---|---|
| Strain of Mice | mIgG1 | IgA | WT Fc[a] | HQ-310/HN-433 |
| β2m−/− (C57BL/6) | 17.6 ± 0.7 (5)[b] | 24.0 ± 0.8 (3) | 12.6 ± 0.7 (4) | 14.8 ± 0.6 (3) |
| β2m−/− (mixed)[c] | 21.2 ± 0.9 (3) | 25.0 ± 2.2 (4) | 12.8 ± 1.5 (5) | 13.7 ± 1.7 (6) |
| β2m+/+ (C57BL/6) | 97.7 ± 5.6 (3) | 21.3 ± 0.7 (3) | 76.9 ± 3.6 (4) | 14.3 ± 0.5 (4) |
| β2m+/+ (mixed) | 199.5 ± 30.8 (3) | 27.0 ± 1.2 (3) | 154.3 ± 30.8 (4) | 15.2 ± 1.1 (3) |

[a]Wild type Fc-hing fragment.
[b]Number of mice used in parentheses.
[c]C57BL/6 × 129/Ola background.

TABLE IV

Serum IgG, IgG1, IgA and
IgM Concentrations in β2m−/− and β2m+/+ Mice

| | Concentration (mg/ml) | | | |
|---|---|---|---|---|
| Strain of Mice | IgG | IgG1 | IgA | IgM |
| β2m−/− (C57BL/6) | 0.30 ± 0.05 (9)[a] | 0.05 ± 0.01 (9) | 0.58 ± 0.16 (9) | 0.12 ± 0.02 (9) |
| β2m−/− (mixed)[b] | 1.22 ± 0.35 (19) | 0.07 ± 0.03 (19) | 1.46 ± 0.68 (19) | 0.35 ± 0.10 (19) |
| β2m+/+ (C57BL/6) | 7.80 ± 1.22 (14) | 1.39 ± 0.33 (14) | 2.27 ± 0.48 (14) | 0.24 ± 0.11 (14) |
| β2m+/+ (mixed) | 1.52 ± 0.29 (13) | 0.25 ± 0.10 (13) | ND | ND |

[a]Number of mice used in parentheses.
[b]C57BL/6 × 129/Ola background.

TABLE V

Synthesis Rates of IgG1 in
β2m−/− and β2m+/+ Mice

| Strain of Mice | Synthesis Rate (mg/day/mouse) |
|---|---|
| β2m−/− (C57BL/6) | 0.189 |
| β2m−/− (mixed)[a] | 0.220 |
| β2m+/+ (C57BL/6) | 0.946 |
| β2m+/+ (mixed) | 0.083 |

[a]C57BL/6 × 129/Ola background.

EXAMPLE 4

The following example illustrates the increased half life and serum persistence of an IgG fragment produced by random mutagenesis of amino acid residues proximal to the FcRn-IgG interaction site. The results provide support for the involvement of FcRn in the homeostasis of serum IgGs in mice and also demonstrate a method for increasing the half life of immunoglobulin fragments. The indications that a homologous FcRn regulates IgG levels in humans indicates that this approach has implications for increasing the serum persistence of therapeutic antibodies.

Construction of Library of Fc-hinge Mutants

The wild type (WT) Fc-hinge gene (Kim et al., 1994a) was used as a template in splicing by overlap extension (Horton et al., 1989) with the following oligonucleotides: HingebakNco (Kim et al., 1994a), 5' ATC ACC ATG GCC GTG CCC AGG GAT TGT GGT TG 3', SEQ ID NO:3, (NcoI site indicated by underlining); 252 for, 5' CAA CAC ACG TGA CCT TAG CSN NCA GSN NAA TSN NGA GC 3', SEQ ID NO:10, (N=T,C,G or A and S=A,G or C; S was inserted in complement at the wobble position to minimize the generation of stop codons); 252bak 5' GTC ACG TGT GTT G 3', SEQ ID NO:11; Xmafor, 5' GCT CCT CCC GGG GTT GCG T 3', SEQ ID NO:12 (XmaI site indicated by underlining). The PCR™ product was digested with XmaI and NcoI and used to replace the corresponding segment of the WT Fc-hinge gene (NcoI site in pelB leader and XmaI at position 211 of Fc-hinge) in pHEN1 (Hoogenboom et al., 1991). A library size of 20,000 clones was generated by electroporation of E. coli TG1 as described (Marks et al., 1991).

Panning of the Library

The library stock was used to generate phage as described (Marks et al., 1991). Phage (100 μl of 2×10$^{12}$ p.f.u./ml) were panned using a solution panning approach as follows: phage were resuspended in 2% milk powder, 20 mM MES (MM buffer) pH 6.0 and mixed with 350 ng recombinant soluble FcRn (Popov et al., 1996) for 1 hour at room temperature with agitation. Thirty microliters of a 50% suspension of Ni$^{2+}$-NTA-agarose (Qiagen) in MM buffer, pH 6.0 were then added, incubated for 10 minutes and pelleted by centrifugation. Beads were washed 20 times with 0.5 ml MM buffer pH 6.0, and phage were eluted by incubation in 100 μl phosphate buffered saline, pH 7.4, for 20 minutes at room temperature. Phage were used to reinfect exponentially growing E. coli TG1 as described (Marks et al., 1991; Ward, 1995). Two rounds of panning were carried out.

Generation of Osmotic Shock Fractions from Selected Clones

Colonies from plates resulting from panning were grown up as 1 ml cultures and induced for Fc-hinge expression as described (Kim et al., 1994a). Osmotic shock fractions were made by resuspension of cell pellets in 15 μl chloroform (Ames et al., 1984) and diluted 10-fold in 50 mM MES, pH 6.0, 0.01% Tween, 150 mM NaCl. Cell debris was pelleted by centrifugation and the supernatants used in Surface Plasmon Resonance (SPR) studies. To estimate the amount of each Fc-hinge fragment in osmotic shock fractions, these fractions were analyzed by immunoblotting using detection with the anti-c-myc antibody as described previously (Ward et al., 1989).

Expression and Purification of Soluble Fc-hinge Fragments

The genes encoding mutated Fc-hinge fragments were recloned as NcoI-NotI fragments into a modified form of VβpelBhis (Ward, 1992) with an inframe NotI site inserted immediately 5' to the codons encoding the polyhistidine tag. Recombinant clones were grown, induced for expression and Fc-hinge fragments purified as described previously (Kim et al., 1994a). Prior to use in SPR studies, Fc-hinge fragments were further purified by size exclusion on a Superdex-75 (Pharmacia, Piscataway, N.J.) column if analytical analysis of the preparation on the same column showed more than one peak at a migration corresponding to 55 kDa.

Pharmacokinetic Analyses

Proteins were radiolabeled with Na $^{125}$I using Iodo-Gen (Amersham, Arlington Heights, Ill.) and pharmacokinetic analyses carried out in SWISS (Taconic) and BALB/c (Harlan) mice as described previously (Kim et al., 1994a).

Surface Plasmon Resonance (SPR) Measurements

These studies were carried out using a BIAcore 2000 (BIAcore Inc.) and methodology similar to that described previously for analyzing Fc-FcRn interactions (Popov et al., 1996). Binding activities of Fc-hinge fragments in osmotic shock fractions were semi-quantitatively analyzed using FcRn coupled to the BIAcore sensor chip (research grade CM5 chip), and clones producing fragments with apparently higher affinities (particularly those with lower off-rates at pH 6.0) than WT Fc-hinge were examined further as purified proteins. The binding of purified Fc-hinge fragments at concentrations ranging from 100–300 nM to immobilized FcRn were analyzed using a flow-rate of 40 μl/min. Fc-hinge fragments were also flowed over an uncoated CM5 chip, and the sensorgrams from these analyses subtracted from those obtained with FcRn-coupled chips using BIA evaluation 2.1 software. For on- and off-rate calculations, the same software was used to fit data to the equations $R=R_{eq}(1-e^{-(ksCn+kd)(t-to)})$ and $R=R_0 e^{-kd(t-to)}$, respectively. Fitting of data to more complex dissociation models (for example, for two parallel dissociation reactions) resulted in negative values for $k_{d1}$ for some mutants, and this model was therefore not appropriate. To minimize effects on $k_d$s due to rebinding, early parts (first 10–15 secs) of dissociation plots were used for analyses. For the WT Fc-hinge, this analysis resulted in a higher off-rate than that calculated previously (Popov et al., 1996), and is the primary cause of the approximate 4-fold lower affinity observed in this example than that described earlier. For each Fc-hinge fragment, values of $k_a$ and $k_d$ were extracted from 3–4 sensorgrams and the average value calculated. $K_D$s ($k_d/k_a$) for each sensorgram were also calculated and the average value determined.

Mutagenesis and Selection

Three residues (T252, T254 and T256) that are in close proximity to I253SEQ ID NO:37 (position 256corresponds to residue 18 in SEQ ID NO: 39, solvent exposed and not highly conserved in IgGs (Kabat et al., 1991) were chosen for random, PCR™ directed mutagenesis. The recombinant Fc-hinge fragments were expressed as a phage display library (approx. 20,000 clones) using the vector pHEN1 (Hoogenboom et al., 1991). The leakiness of readthrough of the amber codon results in a mixture of Fc-hinge:gene III coat protein and soluble Fc-hinge fragments being expressed and assembled as phage displayed Fc-hinge homodimers linked to the gene III coat protein. Two rounds of panning were carried out by incubating phage preparations with recombinant, soluble FcRn (polyhistidine tagged) in solution followed by capture of phage-FcRn complexes using Ni$^{2-}$-NTA-agarose beads. Bound phage were eluted at pH 7.4 to select for Fc-hinge fragments that retained pH dependence of binding that was characteristic of the wild type (WT) Fc-hinge.

Recombinant Fc-hinge fragments from ten of the clones resulting from the panning were analyzed further as soluble fragments in osmotic shock fractions of E. coli transfectants. Using surface plasmon resonance (SPR), five were observed to have a similar or higher affinity for binding to immobilized FcRn than that of the WT Fc-hinge fragment. The genes encoding these Fc-hinge fragments were recloned into a vector with an in-frame C-terminal polyhistidine tag to allow purification of soluble protein on $Ni^{2+}$-NTA-agarose. Following purification, three Fc-hinge fragments were found to have HPLC and SDS-PAGE profiles similar to the WT Fc-hinge (about 55 kDa, comprising a mixture of sulfhydryl linked and noncovalently linked homodimers) and these proteins were subsequently analyzed.

The amino acid sequences of the three mutants at codon positions 251–257 are shown in Table VI. The mutants were named according to the amino acids at positions 252, 254 and 256 (Table VI). The sequences of the remainder of the corresponding genes were the same as that of the WT Fc-hinge fragment with the exception of mutant ASA which had a guanosine (G) to adenosine (A) change at codon 272, resulting in a change of glutamic acid to lysine. This amino acid is located in proximity to the hinge region of IgG (Deisenhofer, 1981) and is therefore unlikely to affect the Fc-FcRn interaction.

TABLE VI

Amino acid sequences of the mutations and flanking regions for the Fc-hinge mutants

| Name | Sequence (251–257) |
| --- | --- |
| ASA | LAISLAP* |
| VSH | LVISLHP |
| LSF | LLISLFP |

*Residues resulting from mutagenesis are indicated in bold.

Pharmacokinetics of the Fc-hinge Fragments

Figure 5:
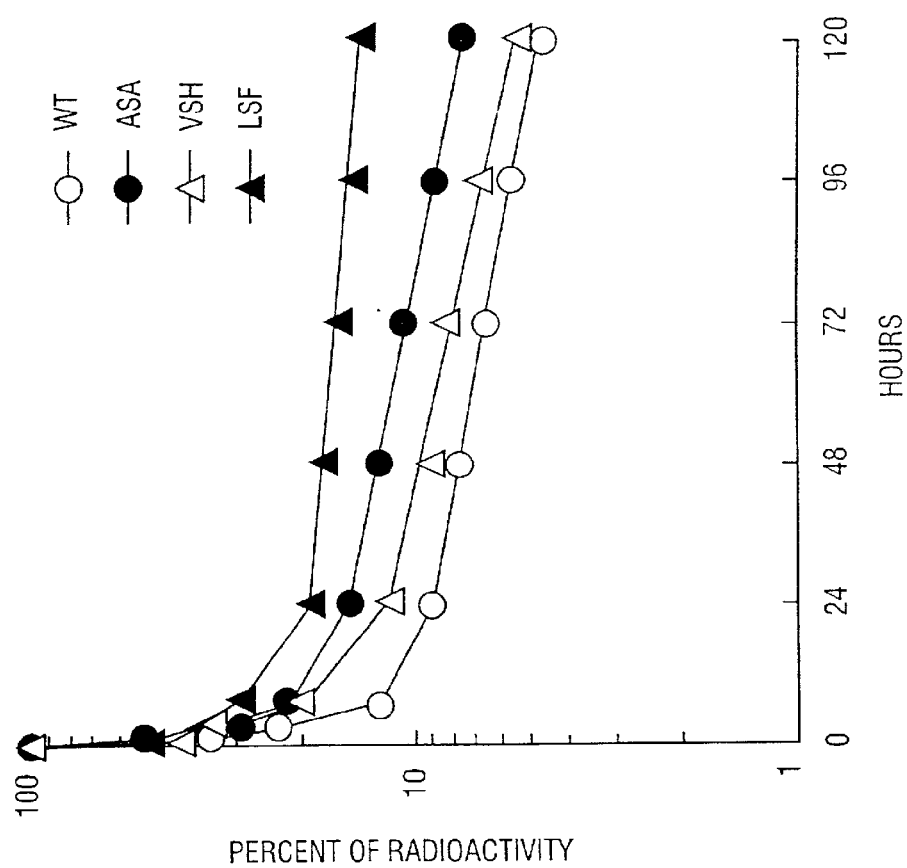
FIG. 5. Clearance curves of Fc-hinge fragments in SWISS mice. Curves for one representative mouse from within each group are shown.

The Fc-hinge fragments were radioiodinated and their pharmacokinetics in SWISS mice analyzed (Table VII: FIG. 5). Of the three mutants, mutant LSF had a significantly longer β-phase half life than either the WT Fc-hinge fragment or mutants ASA or VSH. The half lives of the latter three fragments were not significantly different from each other. Pharmacokinetic studies were also carried out in BALB/c mice, and again mutant LSF had a significantly longer β phase half life than either the WT Fc-hinge or mutants ASA and VSH (Table VII). In BALB/c mice, as in SWISS mice, the half lives of the latter three fragments were not significantly different.

TABLE VII

Pharmacokinetics of the WT and mutant Fc-hinge fragments

| Fc-hinge fragment | SWISS mice Number of Mice | β-phase half life (h)* | BALB/c mice Number of mice | β-phase half life (h)* |
| --- | --- | --- | --- | --- |
| WT | 9 | 123.5 ± 13.3 | 4 | 92.8 ± 12.9 |
| ASA | 4 | 116.0 ± 19.9 | 9 | 104.6 ± 10.4 |
| VSH | 4 | 98.2 ± 6.5 | 9 | 107.1 ± 10.8 |
| LSF | 9 | 152.3 ± 16.0 | 5 | 152.8 ± 12.0 |

*by student t-test the values for WT were not significantly different from those of the ASA and VSH mutants, whereas the values for the LSF mutant were significantly different (p < 0.003 and p < 0.001 for SWISS and BALB/c mice, respectively).

Surface Plasmon Resonance (SPR) Analyses

Figure 6A:
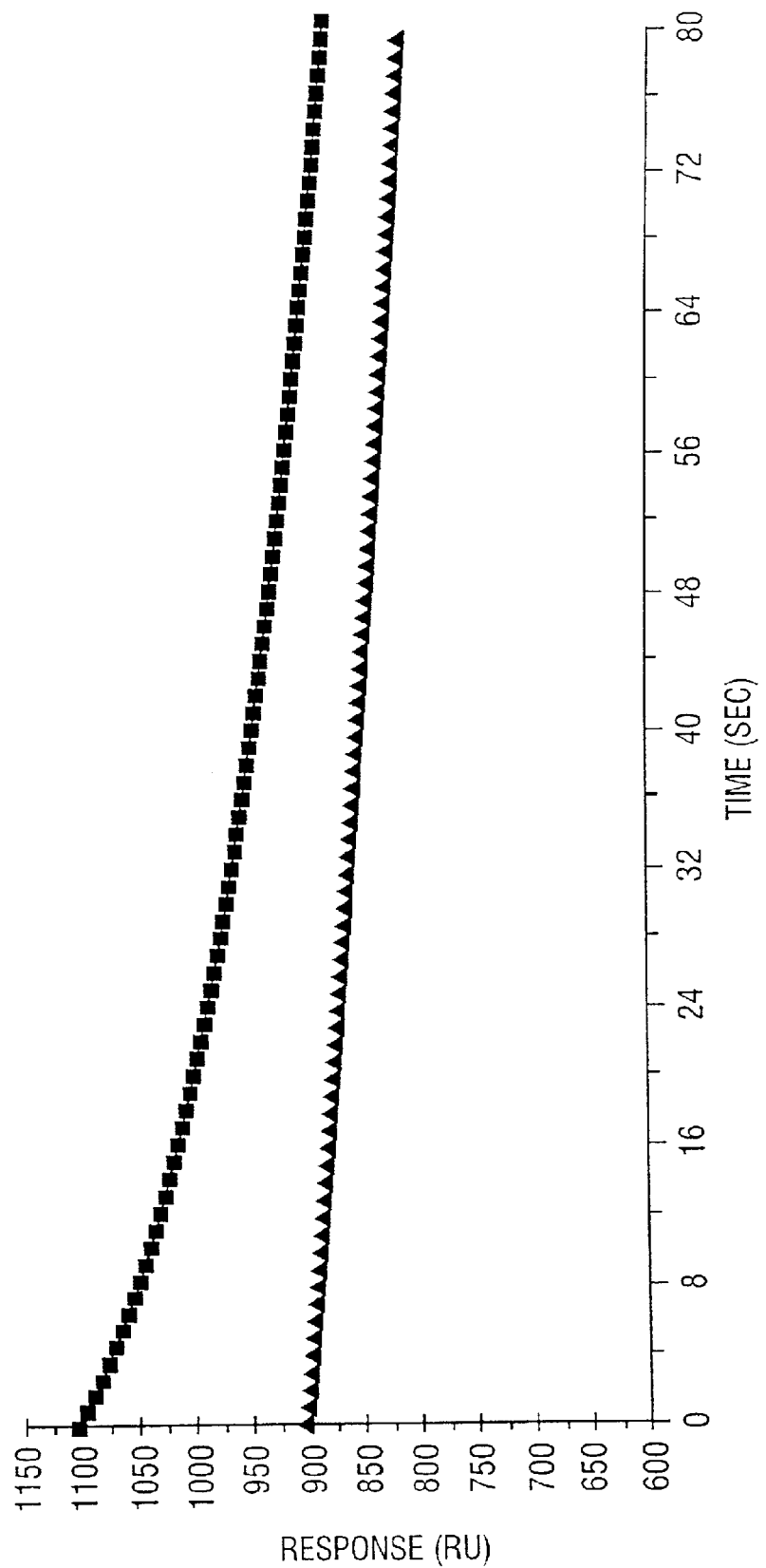
FIG. 6A. Regions of SPR sensorgrams showing dissociation of wild type (WT) (filled squares) and LSF mutant (filled triangles) Fc-hinge fragments at pH 6.0. Plots are drawn using BIAevaluation 2.1 software. Responses as a function of time are shown in response units (RUs).
Figure 6B:
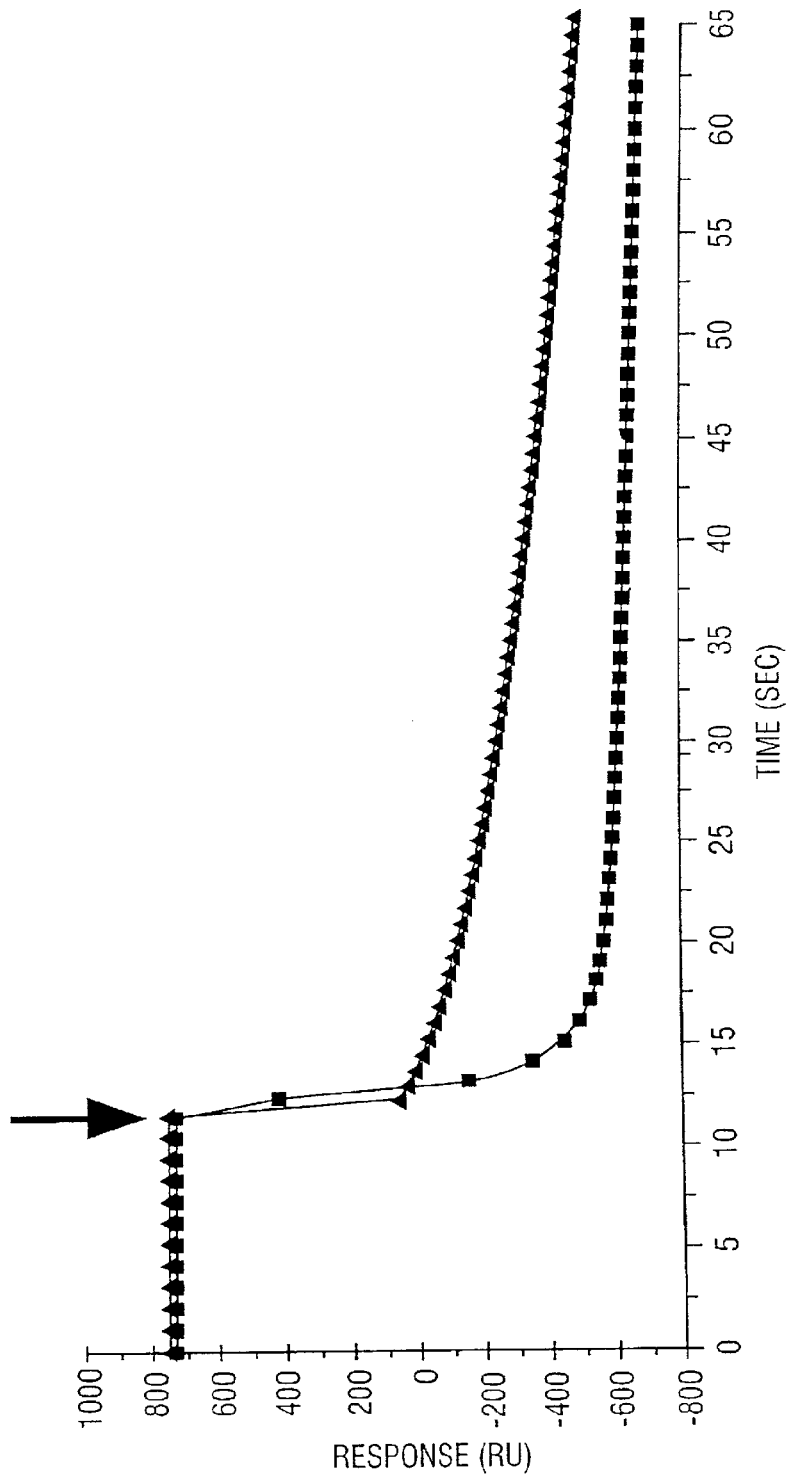
FIG. 6B. Regions of SPR sensorgrams showing dissociation of WT (filled squares) and LSF mutant (filled triangles) Fc-hinge fragments at pH 7.4. The arrow indicates the point at which the buffer was changed from pH 6.0 to 7.4. Plots are drawn using BIAevaluation 2.1 software. Responses as a function of time are shown in response units (RUs). The bulk shift downwards due to the pH 7.4 buffer relative to the pH 6.0 buffer (latter used as a baseline) results in the negative RU values.

The interaction kinetics of each of the three mutants with recombinant, immobilized mouse FcRn were analyzed using SPR (Table VIII). All mutants had similar on-rates ($k_a$s) to that of the WT Fc-hinge fragment. The affinity ($K_D$) differences for mutants ASA (4.13 nM) and LSF (2.16 nM) compared with WT (7.44 nM) were primarily due to significant differences in off-rates, with ASA and LSF having approximately 2- and 4-fold lower $k_d$s, respectively (Table VIII; FIG. 6A and FIG. 6B). The relative affinities of these two mutants were also analyzed using inhibition binding studies in which the ability of each Fc-hinge fragment to inhibit the binding of radiolabeled, soluble FcRn to murine IgG1 coupled to Sepharose was quantitated. Consistent with the SPR analyses, the amount of Fc-hinge fragment needed for 50% inhibition of binding decreased in the order WT>ASA>LSF.

TABLE VIII

SPR analyses of the kinetics of binding of Fc-hinge fragments to FcRn

| Fc-hinge | $k_a(M^{-1}s^{-1})/10^5$ | | $k_d(s^{-1})/10^{-3}$ | | $K_D(k_d/k_a)$(nM) | |
| --- | --- | --- | --- | --- | --- | --- |
| Wild type | 6.20 | ±0.19 | 4.61 | ±0.10 | 7.44 | ±0.19 |
| ASA | 5.01 | ±0.17 | 2.07 | ±0.03 | 4.13 | ±0.10 |
| VSH | 5.38 | ±0.14 | 4.48 | ±0.40 | 8.33 | ±0.68 |
| LSF | 4.72 | ±0.20 | 1.02 | ±0.20 | 2.16 | ±0.36 |

Importantly, the mutations had little effect on the characteristic pH dependence of the Fc-FcRn interaction which is believed to be essential for the correct functioning of this Fc receptor. The off-rates at pH 7.4 for WT, ASA and VSH Fc-hinge fragments were immeasurably fast by SPR. However, mutant LSF had a lower off-rate at pH 7.4 than the WT, ASA or VSH fragments (FIG. 6A and FIG. 6B), although the off-rate of approximately 0.027 $s^{-1}$ is still about 25 fold faster than at pH 6.0 (Table VIII). The retention of the pH dependent binding was consistent with the suggested involvement of H310, H435 and H436, located in loops adjacent to the mutated residues, in mediating this property (Raghavan et al., 1995; Medesan et al., 1997).

The SPR data indicated that the longer half life of mutant LSF relative to WT was accounted for by an approximately 3.5 fold higher affinity for interaction with FcRn, which is primarily due to a decrease in off-rate. These data are consistent with the concept that FcRn is saturable (Brambell, 1964), and that higher affinity Fc fragments have a competitive advantage with endogenous IgGs for being salvaged and recycled rather than degraded. However, the ASA mutant had a 1.8 fold higher affinity for FcRn than WT and yet did not show a significantly longer in vivo half life, suggesting that for significant effects on serum persistence to be observed substantial increases in affinity for FcRn binding were required. Alternatively, the mutations in the ASA mutant may have resulted in an Fc-hinge fragment that had lower stability in the serum, due to enhanced susceptibility to attack by serum proteases or to denaturation.

Analysis of the sequences of the three mutants indicated that a number of different residues can be tolerated at positions 252, 254 and 256 without being detrimental to FcRn binding (mutant VSH) and for mutants ASA and LSF, the affinity was even improved. In this respect, the data indicated that for positions 252 and 256, the WT residues may not make favorable contacts with FcRn as replacement of both T252 and T256 with alanine in the ASA mutant resulted in an affinity increase, contrasting with the apparently essential role of I253 in mediating a high affinity Fc-FcRn interaction, as substitution with alanine at this location resulted in a substantial loss (3000-fold) in affinity (Popov et al., 1996). It is envisioned that other residues could substitute for I253 without alteration in FcRn binding ability, but I253 is conserved across all mammalian IgGs (Kabat et al., 1991).

There appears to be a selection for amino acids with a hydrophobic side chain at position 252, and sequencing of a further mutant with FcRn binding activity similar to that of the WT Fc-hinge revealed Phe at this position. Interestingly, all three mutants had serine at position 254 which is also present in the majority of naturally occurring IgGs of mouse, rat and man (Kabat et al., 1991). The apparent selection of mutants with serine at this position suggests that for retention of FcRn binding activity, serine is the preferred residue. However, the WT Fc-hinge (IgG1) has threonine at this position and still shows a high affinity Fc-FcRn interaction; therefore, it is envisioned that other residues may be present at this position and FcRn binding activity will be retained.

Analyses of the sequences of the mutants indicated that FcRn binding activity was retained with a diverse set of amino acids (Ala, His and Phe) at position 256, suggesting that this region may not be in close proximity to the Fc-FcRn interaction. Residues at this position are, however, highly conserved in rodent and human IgGs (serine or threonine in about 94% of IgGs analyzed; Kabat et al., 1991), indicating that this amino acid might have an as yet unidentified function. It is also possible that the hydrophobic side chain of F256 of the LSF mutant made favorable interactions with FcRn that could not be made by the less hydrophobic alanine or histidine residues in the ASA and VSH mutants, respectively. Such interaction would explain the increased affinity of the LSF mutant relative to VSH, as these two mutants only differed markedly from each other at this position.

Mutant LSF had a lower off-rate from FcRn than the WT Fc-hinge or mutants ASA and VSH at pH 7.4, although this off-rate was significantly faster than that at pH 6.0. This lower off-rate implies that the half life of FcRn on the cell surface (pH 7.4) is sufficiently long to allow significant amounts of this mutant to dissociate into the serum. In this respect the half life of FcRn-LSF mutant complexes at pH 7.4 is about 26 seconds.

These data extend the correlation between affinity of an Fc-hinge fragment for FcRn and β phase half life and further support the proposal (Ghetie et al., 1996; Junghans and Anderson, 1996; Israel et al., 1996) that FcRn is directly involved in IgG homeostasis. It is envisioned that further affinity improvements may be made by targeting other regions of the mIgG1 molecule, such as those in the surface loop containing H310 in the CH2 domain. The observation that aglycosylated Fc-hinge fragments have the same half life as complete glycosylated IgG1 (Kim et al., 1994a) indicates that these data have direct relevance to prolonging the serum persistence of intact IgGs. Furthermore, the site that has been mutated is distal to the interaction sites of FcγRI, FcγRII, FcγRIII (Duncan et al., 1988; Sarmay et al., 1992) and complement C1q (Duncan and Winter, 1988), suggesting that the mutations resulting in longer serum persistence will not affect either ADCC or complement fixation. Finally, the identification of a human homolog of mouse FcRn (Story et al., 1994) suggests that these studies are of relevance to the optimization of the pharmacokinetics of therapeutic antibodies for the treatment of diseases such as cancer and autoimmunity.

EXAMPLE 5

In this example, peptides that bind to FcRn with high affinity at pH 6 and low affinity at pH 7.4 are isolated. Following isolation, binding peptides are analyzed to determine whether they compete with Fc for binding to FcRn i.e., whether they bind to the same or an overlapping site. Peptides, prepared following the disclosed methodology, may be linked to other therapeutic proteins or drugs and thereby effectively increase the half lives of the proteins and tag the drugs. Small peptides are relatively easier to make in large quantities compared to full length proteins; however, to date, peptides have had limited therapeutic use due to their short half lives.

Generation of Peptide Libraries

The phage display vector pHEN1 (Hoogenboom et al., 1991) is used. Random peptide libraries are generated by synthesizing a sense strand oligonucleotide with randomly inserted bases at each position, with the exception of the wobble position that is either T or G in the sense strand to minimize the occurrence of stop codons. Initially, oligonucleotides are designed to encode 10 and 15 amino acids, although this length may be varied. The oligonucleotides are made with overhangs encoding NcoI and NotI restriction sites. Oligonucleotide duplexes are generated using the PCR™ and primers that anneal to the 5' and 3' ends of the synthesized oligonucleotides. The PCR™ products are ligated into NcoI-NotI restricted pHEN1 and ligation mixes are transformed into competent E. coli cells as described previously (Ward, 1995; Popov et al., 1996a). Inserts of 20–30 individual clones are sequenced (Sambrook et al., 1989) to analyze the diversity of the library.

Panning of the Libraries and Selection of Binders

Libraries of clones are grown up, and extruded phage particles concentrated as described previously (Ward, 1995; Popov et al., 1996a). Phage are used in pannings with the following procedure that is designed to isolate high affinity (low off-rate) peptides. Phage are incubated with soluble biotinylated FcRn at limiting concentrations (10 nM) in an analogous way to that described by Hawkins and colleagues (1992), with the exception that all incubations are carried out at pH 6. Following a 1 hour incubation, aliquots of the mixture are diluted into excess unlabeled FcRn (20 μM) and incubated for varying times prior to addition of streptavidin-coated paramagnetic beads to capture biotinylated FcRn-phage complexes. Alternatively, the panning procedure described in Example 4 is used. Phage are then eluted with pH 7.4 buffer and used to reinfect E. coli prior to expansion for a second round of panning.

Following 2–3 rounds of panning, E. coli clones generated by infection with eluted phage are grown up and extruded phage analyzed in enzyme linked immunosorbent assays (ELISAs) for binding to FcRn coated onto 96 well microtiter plates. Phage with binding activity are further analyzed in competition binding assays in which soluble Fc or IgG is added to the phage prior to addition to the wells. Clones producing phage that are inhibited in their binding to FcRn by soluble Fc/IgG are characterized further.

The genes encoding the peptides that bind to FcRn are sequenced and the corresponding peptides synthesized. The affinities of the peptide-FcRn interactions are determined using SPR and the BIAcore (Pharmacia).

The peptides are synthesized in biotinylated form to allow direct coupling to BIAcore chips via streptavidin (streptavidin-coated chips are commercially available from a number of sources). On- and off- rates at both pH 6 and pH 7.4 are determined using previously described methods (Popov et al. 1996a; Jönsson et al. 1991). Peptides that show the highest affinity at pH 6 and/or most marked pH dependence are analyzed further.

FcRn-mediated Transfer of the Peptides

Using methodology analogous to that described for Madin-Darby Canine Kidney (MDCK) cell monolayers expressing the poly IgA receptor (Mostov and Dietcher 1986) an in vitro assay for the functional activity of FcRn is developed. This assay allows the determination of the functional activity of FcRn in mediating the trafficking of bound ligands from one side of a cell monolayer to the other. An alternative assay would analyze transfer of (radiolabeled)

peptides in neonatal mice as described previously for Fc fragments (Kim et al. 1994b).

For the in vitro and in vivo assays, peptides are synthesized with N-terminal tyrosines and radiolabeled using the Iodo-Gen reagent (Amersham). If a peptide contains one or more tyrosines at internal positions, this clearly is not a useful approach. If such is the case, the peptide is extended with an N-terminal glycine during synthesis, linked to the resin via a Rink linker (Rink, 1987) and then directly coupled to radiolabeled succinimydyl hydroxyphenyl propionate at the N-terminus. Various concentrations (1 µg/ml–1 mg/ml) of peptides are added to the appropriate side of the transwell, and transfer of peptide across the monolayer quantitated by gamma counting.

As the Fc-hinge has two FcRn interaction sites per molecule, one may prefer to prepare "repeat" peptides, that is, a peptide that has two interactive sites per molecule, in order to achieve the desired pharmacokinetic characteristics (refer to Example 6 and Table X for exemplary data demonstrating the improved pharmacokinetics achieved by having two interactive sites per protein molecule).

EXAMPLE 6
Site-directed Mutagenesis of the Murine IgG1Fc Region

Recombinant Fc-hinge fragments have been used to determine the site of the murine IgG molecule that is involved in catabolism control (Kim et al., 1994a). Earlier work indicated that Staphylococcal protein A (SpA) complexed with IgG was cleared more rapidly than the uncomplexed IgG molecule (Dima et al., 1983). SpA binds to residues that are located at the CH2–CH3 domain interface (Deisenhofer, 1981) and this suggested that amino acid residues located in this region are also involved in the control of catabolism of the IgG molecule. Thus, the Fc mutants have been expressed in recombinant $E.\ coli$ cells and purified using $Ni^{2+}$-NTA-agarose.

The wild type (WT) and mutant Fc-hinge fragments are each purified in yields of 0.5 milligrams per liter of culture. Analyses by HPLC and reducing and non-reducing polyacrylamide gel electrophoresis indicates that the WT and mutant Fc-hinge fragments are expressed and purified as disulfide linked homodimers, as would be expected for correctly folded Fc-hinge fragments.

Pharmacokinetics of the WT and Mutant Fc-hinge Fragments

The WT and mutant Fc-hinge fragments were radiolabeled using the Iodo-Gen reagent (Fraker et al., 1978) and used in pharmacokinetic studies in mice (Kim et al., 1994a). For all proteins, greater than 90% of the cpm were precipitable by 10% TCA. In addition, analyses using HPLC (SEC-250 columns, Bio-Rad) of plasma samples 24 hours after injection indicated that the WT and mutant Fc-hinge fragments persisted in the serum as intact molecules (size 55 kDa) that were not associated with other serum proteins (Kim et al., 1994a). The pharmacokinetic parameters are shown in Table IX.

TABLE IX

Pharmacokinetic parameters of WT and mutant Fc fragments

| Fc-hinge Fragment | α phase t½ (hours) | β phase t½ (hours) | MRT[1] (hours) | AUC[2] (total: ng/hour/ml) | PC[3] (ng/hour) |
|---|---|---|---|---|---|
| IgG1 | 20.1 ± 0.4 | 85.3 ± 0.1 | 117.1 ± 6.0 | 5651 ± 75 | 1.85 ± 0.02 |
| Wild type | 10.5 ± 0.8 | 82.9 ± 10.0 | 104.4 ± 12.8 | 1949 ± 257 | 5.4 ± 0.8 |
| I-253 | 6.7 ± 0.2 | 20.0 ± 0.6 | 16.3 ± 0.8 | 548 ± 27 | 22.5 ± 1.2 |
| HQ-310 | 6.0 ± 0.6 | 17.5 ± 1.6 | 12.1 ± 1.0 | 528 ± 127 | 20.4 ± 4.7 |
| HN-433 | 10.3 ± 1.2 | 50.3 ± 2.9 | 60.0 ± 5.1 | 1469 ± 232 | 6.9 ± 0.9 |
| HQ-310/ HN-433 | 5.8 ± 0.2 | 15.6 ± 0.8 | 10.4 ± 0.6 | 529 ± 70 | 20.0 ± 4.3 |
| H-285 | 8.7 ± 1.1 | 761 ± 4.6 | 102.1 ± 21.0 | 1572 ± 310 | 6.5 ± 1.5 |

[1]MRT, mean residence time
[2]AUC, area under curve
[3]PC, plasma clearance

It is clear from these data (Table IX) that mutations in the CH2 domain (HQ-310 and I-253) have a more marked effect on the α and β phase half lives than mutations in the CH3 domain (HN-433). However, data from a further study (see Example 10) indicate that His435 and His 436 are important for serum persistence and that mutation of His433 and Asn434 individually have no effect on serum persistence. Furthermore, the HQ-310/HN-433 mutant has the shortest α and β phase half lives. To analyze the folded state of the mutant Fc-fragments, circular dichroism (CD) analyses have been carried out in the range 190–260 nm (Kim et al., 1994a; Medesan et al., 1997). The resulting spectra indicate that the mutations do not result in misfolding of the recombinant Fc fragments (Kim et al., 1994a; Medesan et al., 1997). Furthermore, denaturation analyses using CD indicate that the WT and mutant Fc fragments all have similar denaturation temperatures (65° C.) under the conditions used (10 mM sodium phosphate, pH 7.0). As a further control for these studies, a conserved histidine (residue 285, EU numbering, Edelman et al., 1969) of the IgG1 Fc has been converted to alanine and the mutant (designated H-285) characterized pharmacokinetically (Kim et al., 1994c). The β phase half life (76+/−14.6 hours) of this mutant is statistically indistinguishable from that of the WT Fc (Table IX), indicating that mutation of a histidine that is distal to the CH2–CH3 domain interface (Deisenhofer et al., 1976) does not affect the catabolic rate of the Fc fragment. This further supports the idea that the CH2–CH3 domain mutations have specific effects on the pharmacokinetics, and do not result in more rapid clearance of the Fc due to a general destabilizing effect on Fc structure.

Expression of the Fc Derived Fragments

The genes encoding the CH2-hinge fragment, CH2 domain and CH3 domain were isolated using designed oligonucleotide primers and the PCR™ (Saiki et al, 1988) and ligated into VβpelBHis (Ward, 1992) as NcoI-BstEII fragments. The CH2-hinge, CH2 domain and CH3 fragments have been expressed and purified using $Ni^{2+}$-NTA-agarose as described (Kim et al., 1994c), and the yields of expressed protein are 1–1.5 (CH2-hinge), 2 (CH2 domain) and 1.5–2 (CH3 domain) milligrams per liter of culture. As a control for use in these studies, the anti-lysozyme D1.3 Fv (Ward et al., 1989) was also expressed and purified from recombinant $E.\ coli$ cells.

Analyses using reducing and non-reducing SDS gel electrophoresis indicate that the Fc and CH3 fragments are expressed as a homodimer. In contrast, the CH2-hinge fragment is expressed as a mixture of monomer and —S—S linked dimer. The dimer was separated from the monomer using HPLC and used in pharmacokinetic studies. The CH2 domain was expressed and purified as a monomer, presumably due to the relative weakness of the CH2–CH2 domain interaction in an IgG molecule (Deisenhofer et al., 1976).

Pharmacokinetics of the Expressed Fragments

To determine the clearance rates of the IgG fragments in vivo, they were radiolabeled with $^{125}$-I using the Iodo-Gen reagent (Fraker and Speck, 1978). The α and β phase half lives in mice were determined as described (Kim et al., 1994a; 1994c), and are shown in Table X. The difference in β phase half lives of the CH2-hinge dimer and CH2 domain monomer suggest that two catabolic sites per fragment are needed for serum persistence.

TABLE X

Half-lives of recombinant Fc and Fc-derived fragments

| | | Half Life (hrs) | |
|---|---|---|---|
| Derivative | Number of Mice | α-phase | β-phase |
| IgG1 | 7 | 19.2 ± 1.2 | 89.2 ± 10.6 |
| CH2-hinge dimer | 10 | 6.3 ± 1.2 | 61.6 ± 10.7 |
| CH2-hinge monomer (reduced & alkylated) | 7 | 4.3 ± 0.1 | 29.1 ± 1.2 |
| CH2 | 4 | 2.9 ± 0.1 | 25.5 ± 2.3 |
| CH3 | 9 | 3.4 ± 0.1 | 21.3 ± 2.3 |
| Fv | 4 | 3.4 | 24.1 ± 3.5 |
| WT Fc-hinge | 9 | 10.5 ± 0.8 | 82.9 ± 10.0 |
| HQ-310/HN-433 mutant Fc-hinge | 7 | 5.8 ± 0.2 | 15.6 ± 0.8 |
| Fc-hybrid | 16 | 7.3 ± 1.2 | 37.9 ± 7.1 |

Figure 7:
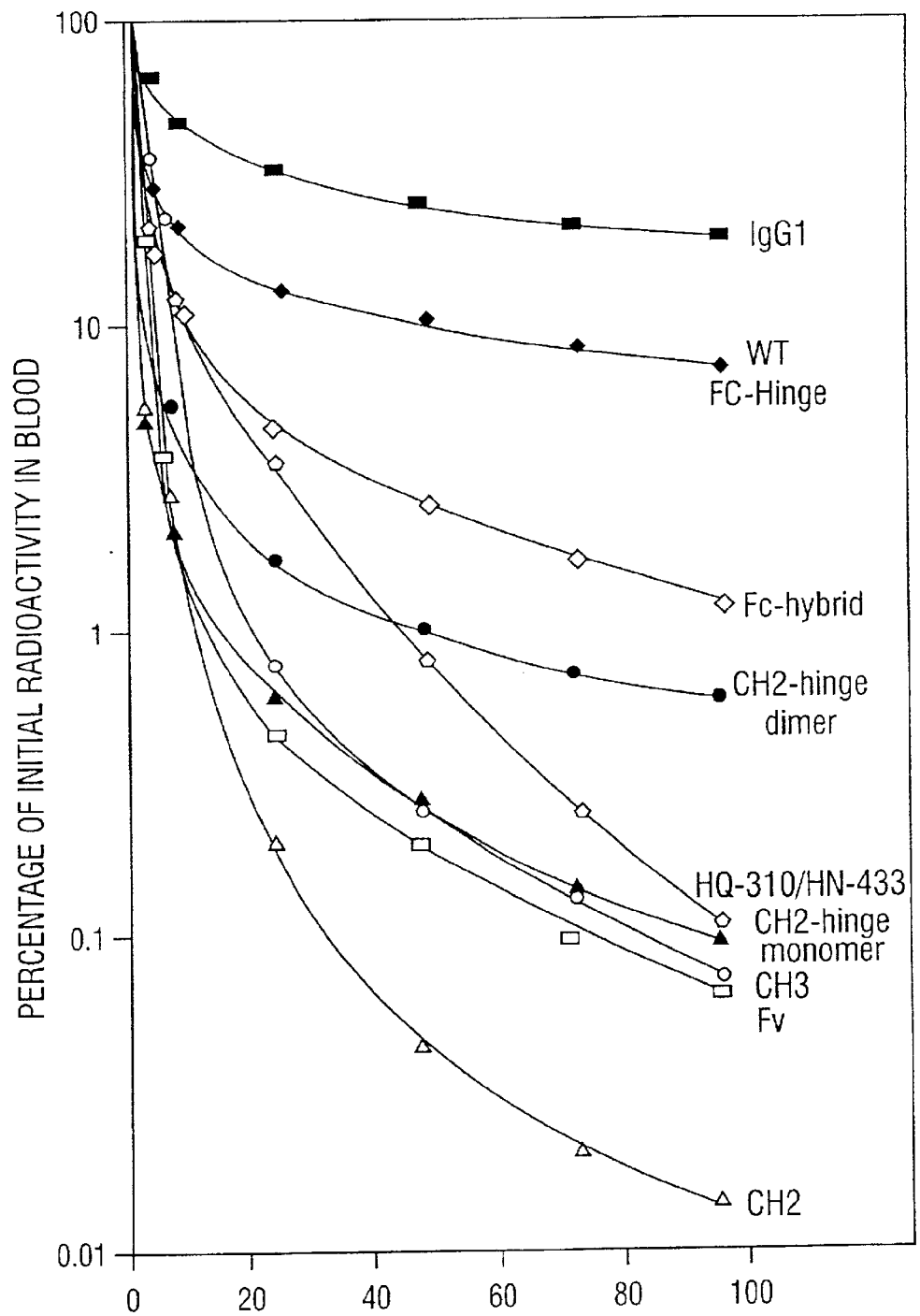
FIG. 7. Clearance curves of the murine IgG1 molecule and IgG1-derived fragments.

To exclude the possibility that the shorter half life of the CH2 domain versus the CH2-hinge dimer was due to the presence of the hinge sequences in the latter, the CH2-hinge dimer was converted into a monomer by reduction and alkylation (Kim et al. 1994c). The resulting monomer was analyzed pharmacokinetically and found to have a short β phase half life (29.1 hours) similar to that of the CH2 domain monomer (25.5 hours). This indicates that two catabolic sites per CH2-hinge fragment result in longer serum persistence than one site per CH2-hinge. Alternatively, the size differences between the monomer and dimer may account for the differences in serum persistence. To investigate this possibility, a hybrid Fc fragment was made which comprised one WT Fc polypeptide associated with one mutant (HQ-310/HN-433) polypeptide This hybrid was isolated by tagging the mutant Fc with a c-myc tag (in a plasmid conferring kanamycin resistance) and the WT Fc with a His$_6$ peptide (in a plasmid conferring ampicillin resistance) and co-expressing the two polypeptides in the same bacterial cell (Kim et al. 1994c). Heterodimers were purified using an Ni$^{2+}$-NTA-agarose column followed by a 9E10-Sepharose column (the latter recognizes the c-myc epitope, Ward et al., 1989). The hybrid protein was used in pharmacokinetic studies (FIG. 7 and Table X). The β phase half life of 37.9 hours for the Fc-hybrid is less than that of WT homodimers but greater than that of mutant homodimers. This indicates that one catabolic site per Fc is insufficient to confer the pharmacokinetic characteristics of the WT homodimer on the Fc fragment. Within the framework of the Brambell hypothesis (Brambell et al., 1964; Brambell, 1966) the data suggest that the hybrid has reduced avidity for binding to protective receptors and as a result is cleared more rapidly that WT Fc homodimers. However, the more rapid clearance of the mutant homodimer relative to the Fc-hybrid suggest that the latter retains a higher binding affinity for the protective receptors than the homodimer and binding of this Fc-hybrid to recombinant FcRn has recently been shown using SPR (Popov et al., 1996b).

Intestinal Transfer of Fc Fragments in Newborn Mice

The effects of the mutations shown in Table XI on the intestinal transfer of recombinant Fc fragments in newborn mice have been analyzed using a variety of approaches which are described below.

TABLE XI

Fc derivatives used in intestinal transfer studies

| Designation | Mutation |
|---|---|
| WT Fc | None |
| I-253 | Ile 253 to Ala 253 |
| HQ-310 | His 310 to Ala 310 and Gln 311 to Asn 311 |
| HN-433 | His 433 to Ala 433 and Asn 434 to Gln 434 |
| HQ-310/HN-433 | HQ-310 and HN-433 within same Fc-hinge |
| Fc-hybrid | Hybrid comprising heterodimer of WT-Fc-hinge and HQ-310/HN-433 mutant |

Direct Transfer of Fc Fragments from Gut Lumen to Plasma

The complete IgG1molecule (mIgG1), WT and mutant (HQ-310/HN-433) Fc fragments were radiolabeled and analyzed in in vivo transfer assays in 10–14 day old mice (Kim et al., 1994b). As controls, an Fc fragment produced by papain digestion and an Fab fragment were used. The hybrid Fc fragment was also analyzed.

Figure 8:
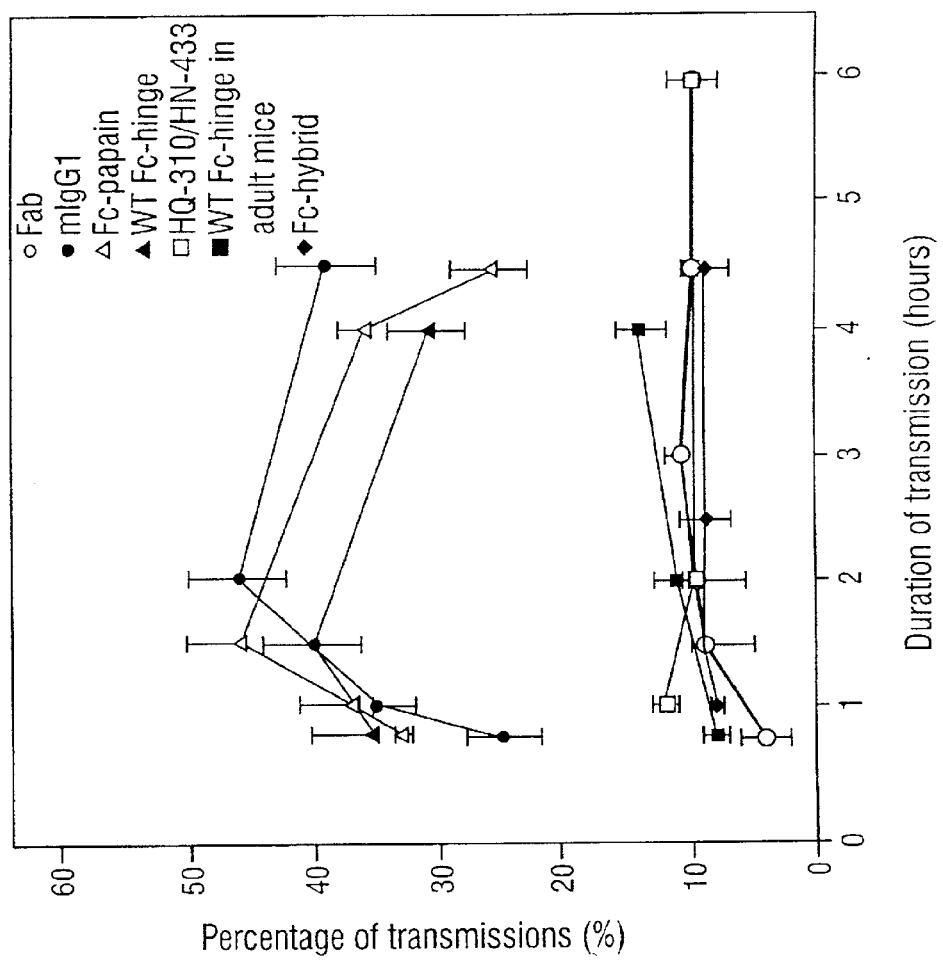
FIG. 8. Intestinal transfer of murine IgG1, Fab, Fc-papain and recombinant Fc fragments. The numbers of mice used for each study were 6(Fab), 12 (mIgG1), 16 (Fc-papain), 31 (WT Fc), 5 (HQ-310/HN-433), 5 (WT Fc in adult mice) and 14 (Fc-hybrid).

The results shown in FIG. 8 indicate that the WT Fc fragment is transferred as well as the Fc-papain and mIgG1, indicating that glycosylation (or lack of it) does not affect transfer. This is consistent with earlier data of Hobbs and colleagues (Hobbs et al., 1992). These results also show that mutant HQ-310/HN-433 is impaired in transfer, suggesting that the catabolic site overlaps that involved in intestinal transfer and that the Fc-hybrid is impaired in transfer, indicating that two functional sites per Fc are required. This resembles the findings regarding the need for two catabolic sites in catabolism control (data above and Kim et al. 1994c).

However, these data do not distinguish between a defect of the mutant Fc fragments in binding to the neonatal intestinal receptor, FcRn, and/or transcytosis, and therefore further studies involving inhibition of transfer were carried out.

Competition Transfer Assays

Figure 9:
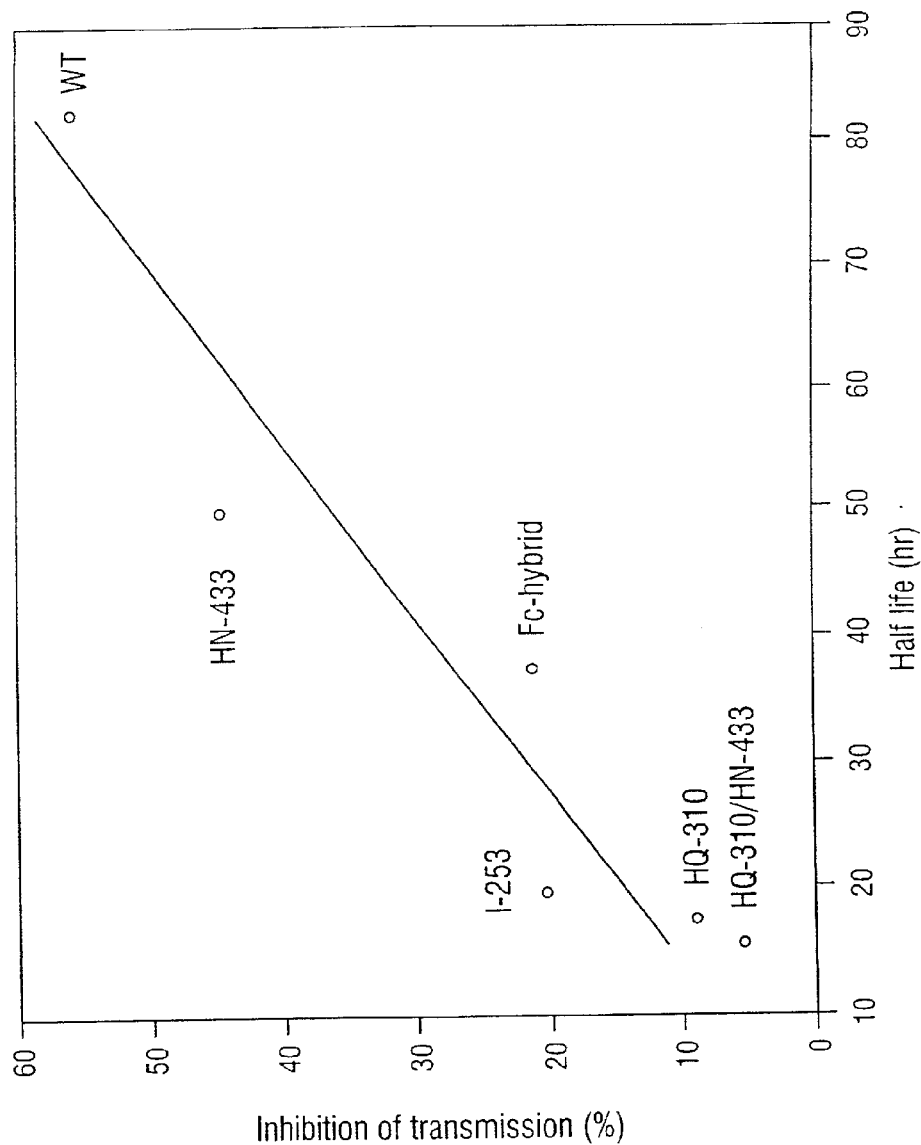
FIG. 9. Correlation between β phase half life and inhibition of transfer for the recombinant WT and mutant Fc fragments.

In these assays, the abilities of unlabeled WT and mutant Fc fragments to inhibit transfer of radiolabeled murine IgG1 were analyzed. In addition to the HQ-310/HN-433 mutant, the mutants described in Table XI were also used. The results of these studies are shown in Table XII. The data clearly show that the mutants are defective in competing with the complete IgG1 molecule for binding to FcRn. Furthermore, the effect of each mutation on half life shows an excellent correlation with the effect on inhibitory capacity (FIG. 9).

TABLE XII

Inhibition of intestinal transmission of radiolabeled murine IgG1 (mIgG1) by recombinant Fc derivatives

| Competitor | Inhibition of transmission (%)* |
|---|---|
| IgG1 | 51.4 |
| Ec-papain | 62.5 |
| WT Fc | 55.3 |
| I-253 | 20.2 |
| HQ-310 | 8.9 |
| HN-433 | 44.4 |
| HQ-310/HN-433 | 5.4 |

TABLE XII-continued

Inhibition of intestinal transmission of
radiolabeled murine IgG1 (mIgG1) by recombinant Fc derivatives

| Competitor | Inhibition of transmission (%)* |
|---|---|
| Fc-hybrid | 21.5 |
| BSA# | 8.9 |

Figure 10:
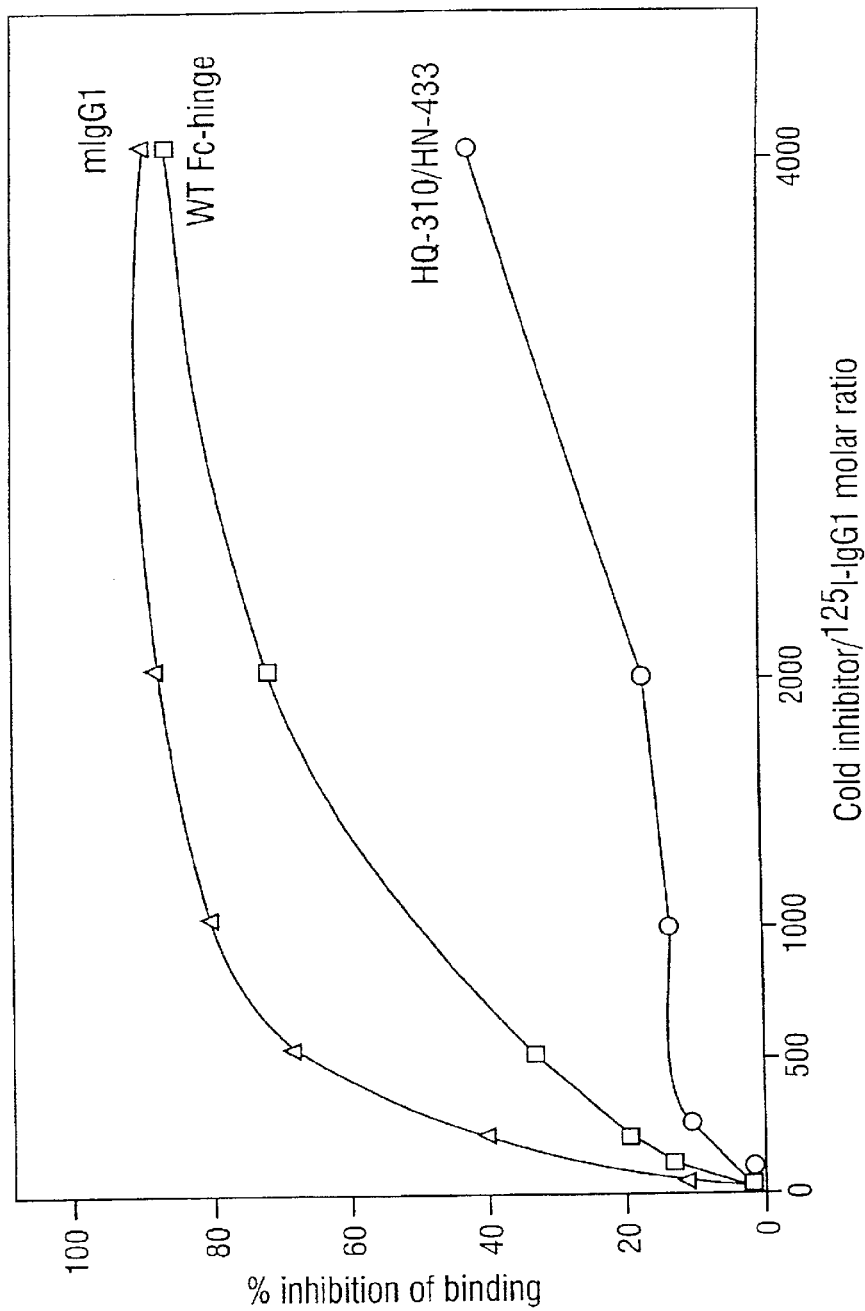
FIG. 10. Inhibition of binding of $^{125}$I-IgG1 to isolated brush borders by unlabeled IgG1, WT and HQ-310/HN-433 mutant Fc fragments.

*relative to transmission of radiolabeled IgG1 in presence of PBS
BSA, bovine serum albumin To further confirm and extend these results, neonatal brush borders were isolated and used in binding studies with the WT Fc and HQ-310/HN-433 mutant Fc, in which the ability of mIgG1, WT Fc and HQ-310/HN-433 mutant to inhibit binding of mIgG1 to isolated neonatal brush borders was assessed (FIG. 10).

In conclusion, these studies have resulted in the identification of the site of the murine IgG1 molecule that is involved in interacting with FcRn during intestinal transfer in neonatal mice. The data indicate that the catabolic site and FcRn binding site are closely related.

Maternal-fetal Transfer of WT and Mutant Fc Fragments

Studies have been carried out to analyze the maternal-fetal transfer of murine IgG1 (mIgG1), WT Fc and HQ-310/HN-433 mutant, using the methodology described below in Example 9. The data clearly show that the mutant is transferred at significantly lower levels than mIgG1 and WT Fc (Table XIII).

TABLE XIII

Maternal-fetal transfer of mIgG1, WT Fc and HQ-310/HN-433 mutant

|  | mIgG1 | WT Fc | HQ-310/HN-433 |
|---|---|---|---|
| Radioactivity injected (cpm) | 2,005,435 | 1,890,540 | 1,958,436 |
| Radioactivity in maternal blood at 3 min. (cpm) | 1,085,000 | 770,350 | 836,150 |
| Radioactivity in maternal blood at 4 h. (cpm) | 725,501 | 215,431 | 219,431 |
| Radioactivity in fetuses at 4 h. (cpm) | 28,450 | 13,750 | 1,359 |
| Percent of transmission relative to 3 min. levels | 2.71 | 1.78 | 0.16 |
| Percent of transmission relative to 4 h. levels | 4.05 | 6.38 | 0.62 |

EXAMPLE 7

The data described above in Examples 3 and 4 indicate that murine FcRn and FcRc (the putative 'protective' receptor involved in catabolism control) are related, and may even share common sequences. Thus the isolation of the gene encoding a putative FcRc from murine tissues and cell lines was undertaken and is described in this example.

PCR™ primers based on the sequence of murine FcRn (Ahouse et al., 1993) that are not homologous to murine Class I molecules (Simister and Mostov, 1989a) were designed as follows:

Primer A: 5' CAG GAA GCT GAC CCC TGT GGG NN 3' (SEQ ID NO:13)

This primer encodes bases 190–212 of the sense strand of murine FcRn.

Primer B: TTC CGT CTC AGG CCA CTC CCC NN 3' (SEQ ID NO:14)

This primer is complementary to bases 452–474 of the sense strand of FcRn. Note that for both primers, two degenerate bases were inserted at the 3' end of each primer in case the sequence of FcRc did not match FcRn precisely.

Total RNA was isolated from two endothelial cell lines [SVEC, derived from C3H/HeJ mice (O'Connell and Edidin, 1990) and MPCE, derived from lungs of B10.DBA/2 mice; obtained from Prof. P. Thorpe and Prof. A. Curtis, respectively] and cDNA synthesis primed with primer B. The cDNA was then used in PCRs™ with primers A and B, and for both cDNAs, PCR™ products of 285 bp were generated. No product was observed in the negative controls, indicating that this result is not due to PCR™ contamination by neonatal murine intestine. The PCR™ products were cloned using the TA cloning system (Promega) and sequenced using the dideoxynucleotide method (Sanger et al., 1977). Sequencing of multiple independent clones indicates the sequence of the 285 bp fragment is the same as that of FcRn with the exception of one base change (A to G) which converts valine to methionine at codon 73.

The isolation of this 285 bp fragment from endothelial cell lines prompted the design of PCR™ primers to amplify the genes encoding the transmembrane regions and cytoplasmic tail as follows:

Primer C: 5' TCT GGC TCC TCC GTG CT 3' (SEQ ID NO:6)

(encodes bases 640–656 of the sense strand of FcRn)

Primer D: 5' TCA GGA AGT GGC TGG AAA GGC ATT 3' (SEQ ID NO:15)

(complementary to bases 1075–1095 of sense strand of FcRn).

Complementary DNA (cDNA) was synthesized from RNA derived from the two endothelial cell lines, murine heart, liver, lung, spleen, yolk sac, neonatal brush border and T/B cell hydridomas priming with primer D. For tissues, BALB/c mice were used, and the 2B4 (T cell; Chien et al., 1984) and Y-3P (B cell, Janeway et al., 1984) hybridomas were derived from B10.A and BALB/cByJ mice, respectively. The use of these cDNAs in PCR™ with primers C and D resulted in the isolation of products of the predicted size from all cells except the T and B cell hybridomas. In all cases, PCR™ products of the expected size were seen using β-actin specific primers.

There are consistently quantitative differences in the amounts of PCR™ product obtained from the above tissues/cells, which in turn suggests different levels of mRNA, with yolk sac and neonatal intestine (brush border) producing the highest amounts, and the amounts in the other tissues decreasing in the order: liver>spleen, lung>heart. Quantitative PCR™ are carried out to assess the mRNA levels in these different cell types. PCR™ products from liver, spleen, neonatal brush border and lung have been cloned and sequenced in the region 640–870 and found to share a high degree of homology with FcRn. Furthermore, the complete FcRn homolog has been isolated from the two endothelial cell lines using primers D and E and multiple independent isolates sequenced; there are a total of 4 nucleotide differences, 3 of which are silent and one A to G change (converting valine to methionine) at codon 73. The silent mutations at codons 233, 251 and 265 are also seen in PCR™ products isolated from the liver, spleen, neonatal brush border and lung (derived from BALB/c mice).

Primer E: 5' ATG GGG ATG CCA CTG CCC TGG 3' (SEQ ID NO:16) (encodes bases 1–21 of the sense strand of FcRn, including leader peptide).

The sequence differences between the published FcRn sequence and the FcRn gene isolated are most likely allelic differences due to the different mouse strains used by the inventors and Simister and colleagues who used FVB/N mice (Ahouse et al., 1993), who found no hybridization of an FcRn cDNA probe to mouse placenta, adult mouse proximal small intestine, thymus, spleen, kidney nor liver, although expression at the protein level in mouse fibroblasts was not excluded. The reasons for these differences may be due to differences in the sensitivity of the methods used i.e. PCR™ versus northern blotting. Consistent with the data, Simister and colleagues (Story et al., 1994) have recently reported that an FcRn homolog was expressed at high levels in human placenta, in addition to ubiquitous expression in many other adult human tissues. For the rat also, weak hybridization of FcRn probes to RNA from adult tissues was observed after high stringency washes (Simister and Mostov, 1989a; Simister and Mostov, 1989b). Low level expression of the receptor involved in the control of catabolism in the ubiquitous endothelial cells, i.e. in all vascularized organs, would be consistent with the proposed role of this protein in maintaining constant serum IgG levels. These expression data, together with the data presented in Examples 3 and 4 above, suggest that FcRc and FcRn are one and the same.

Expression of FcRn in Soluble Form in the Baculovirus System

The gene encoding the extracellular regions (codons 1–290, including leader peptide) of FcRn has been tagged with 3' His$_6$ peptide codons (Ward, 1992), tailored with BamHI sites using the PCR™ and ligated into the BglII site of pACUW51 (Invitrogen) for expression in the baculovirus system (O'Reilly et al., 1992). The gene encoding β2-microglobulin was also amplified using the PCR™ and tagged with BglII sites and ligated into the BamHI site of pACUW51. The vector FcRn-pAC was used to transfect *Spodoptera frugiperda* (Sf9) cells and recombinant viruses plaque purified. A recombinant virus stock has been generated and used to infect High-5 cells (*Trichoplusia ni*; Invitrogen) which expresses higher levels of recombinant protein than Sf9 cells. Following 4 days of infection, culture supernatant and lysed pellets were passed over $Ni^{2+}$-NTA-agarose and bound protein eluted. Using this system, 15 milligrams of FcRn per liter of cells can be routinely purified. SDS-PAGE and immunoblotting (using anti-β2-microglobulin sera analyses indicate that the protein is purified as a heterodimer of heavy chain and β2-microglobulin. HPLC analysis indicates that the FcRn heavy chain is quantitatively associated with β2-microglobulin. Furthermore, binding studies with radio-labeled soluble FcRn (designated sFcRn) to murine IgG1-Sepharose indicate that sFcRn binds to mIgG1 coupled to Sepharose in a pH dependent and specific way (Table XIV).

TABLE XIV

Binding of sFcRn to mIgG1-Sepharose

| pH of incubation | Initial radioactivity added | Bound radioactivity | Bound radioactivity after pH 7.5 wash |
| --- | --- | --- | --- |
| 6.0 | 913,948 cpm # | 271,425 cpm | 42,552 cpm |
| 6.0 | 937,685 cpm | 227,828 cpm | 42,656 cpm |
| 6.0 | 937,985 cpm | 70,659 cpm* | 26,492 cpm |
| 7.5 | 931,302 cpm | 19,576 cpm | 16,816 cpm |
| 7.5 | 943,936 cpm | 11,556 cpm | 10,269 cpm |
| 7.5 | 958,958 cpm | 12,339 cpm | 9,468 cpm |

*in presence of 500 μg mIgGI
specific activity of labeled rFcRn was $10^6$ cpm/μg Binding of WT and Mutant Fc Fragments to FcRn Studies in which the binding of $^{125}$-I sFcRn to IgG-Sepharose was inhibited by murine IgG1, WT or mutant Fc fragments indicate that the I-253, HQ-310, HQ-310/HN-433 mutants are all deficient, relative to WT Fc, in binding to sFcRn. This is consistent with the in vivo transfer data and in vitro binding studies with isolated brush borders (Table XV).

TABLE XV

Inhibition of binding of$^{125}$-I labeled sFcRn to murine IgG1-Sepharose by murine IgG1, WT and mutant Fc fragments

| | % inhibition Molar ratio of inhibitor/FcRn | |
| --- | --- | --- |
| Inhibitor | 1/500 | 1/1000 |
| mIgG1 | 24.7 | 45.6 |
| WT Fc | 18.4 | 34.1 |
| HQ-310/HN-433 | 0.2 | 4.0 |
| I-253 | 2.3 | 6.5 |
| HQ-310 | 1.6 | 6.1 |

Expression of Fc Fragments on the Surface of Bacteriophage

Construction of Phage Display Vectors

Figure 11:
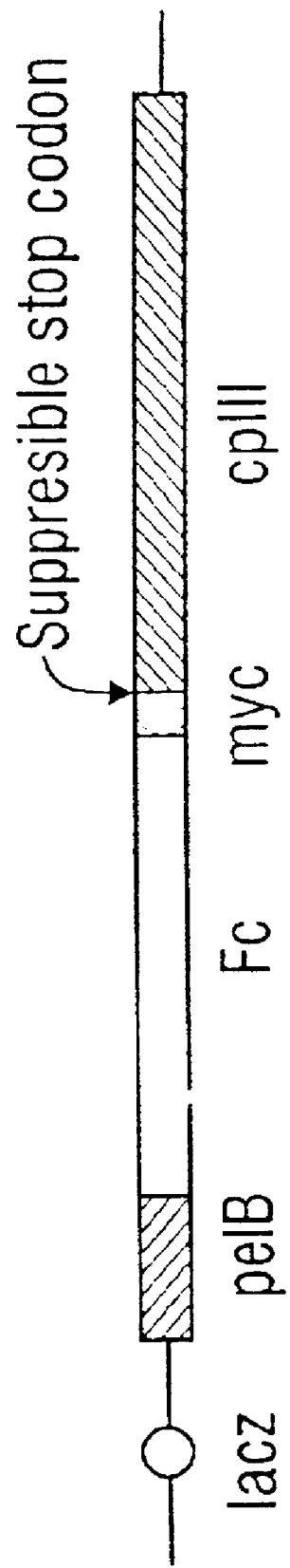
FIG. 11. Expression/phage display vector containing Fc gene (WT or mutant). Open circle=lacz promoter, hatched box=pelB leader, open box=WT Fc or HQ-310/HN-433 mutant, filled in box=c-myc tag and stippled box=cpIII gene. Single lines =backbone vector.

The phagemid constructs shown in FIG. 11 were made. The genes encoding the WT Fc and HQ-310/HN-433 fragments (including hinge regions) were tailored by the PCR™ for ligation as NcoI-NotI fragments into the vector pHEN1 (Hoogenboom et al., 1991). The advantage of using pHEN1 for this work is the following: the Fc gene is linked via a suppressible stop codon (amber) to the cpIII coat protein of the filamentous bacteriophage, fd. Thus, transfection of the amber suppressor strain *E. coli* TG1 (Gibson, 1984) with the phagemid followed by superinfection with helper phage results in extrusion of phagemid particles (Hoogenboom et al., 1991) that, in this case, bear surface bound Fe fragments. However, the suppression is not complete so that a significant proportion of Fc fragments are exported as soluble, unlinked molecules (clearly observed on immunoblots). These soluble Fe fragments therefore associate with surface bound Fe fragments to form homodimers, in a similar way to that described previously for the heavy and light chain components on Fab fragments (Hoogenboom et al., 1991).

Functional Activity of Phage Displayed Fc Fragments: Binding to sFcRn

*E. coli* TG1 transformants harboring either the WT Fe or HQ-310/HN-433 mutant in pHEN1 have been grown up, phage extruded and concentrated by polyethylene glycol precipitation (Marks et al., 1991). The phage pellets were resuspended in 2% milk powder/PBS (pH 6) and purified sFcRn added at a concentration of 10 μg/ml in the presence or absence of 50 μg of murine IgG1. Following two hours of incubation, sFcRn-phage complexes were isolated by the addition of 10 μl of $Ni^{2+}$-NTA-agarose and the agarose beads washed extensively with 0.1% Tween/PBS (pH 6) followed by PBS, pH 6. Specifically bound phage were eluted using 50 mM Tris-HCl pH 7.5 and used to infect exponentially growing *E. coli* TG1 as described (Marks et al., 1991). Infected TG1 cells were serially diluted, plated and the cfu determined (Table XVI).

TABLE XVI

Panning of phage bearing Fc fragments against sFcRn

| Amount of IgGI added (µg) | Number of colonies | |
|---|---|---|
| | WT Fc bearing phage | HQ-310/HN-433 bearing phage |
| 50 | 41 | 230 |
| 0 | >2000 | 109 |

From these data and Example 4 it is clear that this system results in the phage display of Fc fragments that bind to sFcRn specifically, and is therefore a suitable system for the selection of Fc mutants that have higher affinity for FcRn binding.

EXAMPLE 8

The this example, the roles of residues His 433, His435 and His 436 in control of serum IgG levels and transcytosis are examined in pharmacokinetic studies. It has been noted previously that the mIgG2b molecule has a shorter serum persistence than either mIgG2a or mIgG1 (Pollock et al., 1990), but the sequences that are responsible for this have not been mapped. Based on earlier data the inventors stipulated that the difference in half life may be due to sequence differences in the CH3 domain at positions 433, 435 and 436. In IgG2a and IgG1, the residues at these positions are His433, His435 and His436 and data indicate that His435 and His436 (and His433 if in the context of the double mutation of His433-Asn434) are involved in regulating serum persistence (Medesan et al., 1997). In mIgG2b, the residues at these positions are Lys433, Tyr435 and Tyr436. The inventors mutated residues 433, 435 and 436 in mIgG2b to the corresponding residues in mIgG1, in the expectation that these mutations might increase the half life of the mIgG2b molecule.

Preparation and Radiolabeling of Proteins

Recombinant Fc fragments are purified using $Ni^{2+}$-NTA-agarose and radioiodinated using the Iodo-Gen reagent (Amersham) as described previously (Kim et al., 1994a).

Pharmacokinetic Studies

Essentially the methodology described previously (Kim et al., 1994a) is used. In brief, proteins are radiolabeled, a specific activity of $10^7$ cpm/µg is routinely obtained using this method) and free iodine is removed by two successive gel filtrations on Sepharose G-25M. Radiolabeled Fc fragments are analyzed on SEC-250 columns by permeating HPLC prior to injection into mice. Radiolabeled proteins are injected into the tail vein in a volume not larger than 150 µl and a radioactive load of $1-5 \times 10^7$ cpm. Mice are bled with heparinized capillary tubes at intervals up to 120 hours post injection. Radioactivity present in plasma is determined as described (Kim et al., 1994a), and aliquots of the plasma added to 10% trichloroacetic acid (TCA) to determine the non-precipitable cpm. Plasma is collected at 24 hours post-injection and analyzed by HPLC on SEC-250 columns (Kim et al., 1994a).

Generating a Murine IgG2b (mIgG2b) Antibody with Longer Serum Persistence

Unexpectedly, the mIgG2b Fc-hinge fragment, expressed and purified from *E. coli*, has a shorter serum persistence than the complete gylcosylated murine IgG2b molecule (note that this is in contrast to the results obtained for the murine IgG1 Fc-hinge where *E. coli* expressed material has the same half life as complete glycosylated IgG1. Therefore, vectors have been built to express the complete murine IgG2b molecule (wild type and a mutated derivative in which Lys433, Tyr435 and Tyr436 were changed to His433, His435 and His436; the latter is designated KYY mutant) using the baculovirus expression system. Expression in insect cells is known to result in glycosylated protein, using the same recognition sequences for glycosylation as those used in mammalian cells. The genes encoding the IgG2b constant region were isolated and spliced, using the PCR™ and appropriate oligonucleotide primers, to the gene encoding the VH domain gene of an anti-lysozyme antibody (D1.3; Amit et al., 1986). Similarly, the gene encoding the murine Cκ domain was spliced to the D1.3 Vκ domain. Secretion leaders were also inserted upstream of both heavy and light chain genes using the PCR™. The immunoglobulin genes encoding the light and heavy chains were then ligated into pACUW51 (Pharmingen), a baculovirus expression vector.

The vectors were transfected into Sf9 (*Spodoptera frugiperda*) cells, recombinant viruses plaque purified and used to infect High 5 (*Trichoplusia ni*) cells for expression. Following 4 days of infection, recombinant antibodies were purified from the culture supernatants using lysozyme Sepharose as described (Ward et al. 1989). The mutant mIgG2b (KYY) molecule was purified and its in vivo half life analyzed in SWISS mice. The half life has been compared with myeloma (B cell) expressed mIgG2b (unmutated) and mIgG1, and the results are shown in Table XVII.

TABLE XVII

Half lives of mIgG1, mIgG2b (myeloma expressed) and mutated mIgG2b (KYY mutant)

| Antibody | β phase half life (hours) |
|---|---|
| mIgG1 | 123.5 ± 13.3 |
| mIgG2b (WT) | 56.1 ± 5 |
| mIgG2b (KYY mutant) | 110.9 ± 16.2 |

Clearly, the mutations have resulted in a significant increase in half life (56.1 hours to 110.9), and the half life of the mutated IgG2b molecule is the same as that of mIgG1 in SWISS mice. Thus, some or all of the residue differences at 433, 435 and 436 account for the half life differences between wild type mIgG2b and mIgG1.

EXAMPLE 9

Materials and Methods

Generation of Mutated Fc Hinge Fragments Derived from mIgG1

Mutations were made using designed mutagenic oligonucleotides and either splicing by overlap extension (Horton et al., 1989) or site-directed mutagenesis (Carter et al., 1985; Kunkel, 1985). The mutants are described in Table XVIII and the generation of mutants 1253A and H285A has been described previously (Kim et al., 1994a; 1994c). For other mutants, mutagenic oligonucleotides used in site-directed mutagenesis were as follows (underlines indicate mutated bases): H433A, 5'-GGTGGTTGGCCAGGCCCCT-3' SEQ ID NO:17; H435A, 5'-CAGTATGGGCGTTGTGCA-3' SEQ ID NO:18; and H436A, 5'-CTCAGTAGCGTGGTTGTG-3' SEQ ID NO:19. Mutants H310A, N434A, and N434Q were made using splicing by overlap extension (Horton et al., 1989) with the following mutagenic oligonucleotides: H310A, 5'-CCCATCATGGCCCAGGACTGG-3' SEQ ID NO:20 and 5'-CCAGTCCTGGGCCATGATGGG-3' SEQ ID NO:21; N434A, 5'-GGCCTGCACGCGCACCATACT-3'

SEQ ID NO:22 and 5'-AGTATGGTGCGCGTGCAGGCCCTC-3' SEQ ID NO:23; and N434Q, 5'-AGTATGGTGTTGGTGCAG-3' SEQ ID NO:24 and 5'-CTGCACCAACACCATACT-3' SEQ ID NO:25. For all mutants, the corresponding genes were sequenced using the dideoxynucleotide method (Sanger et al., 1977) and Sequenase® before functional analysis.

Expression and Purification of the Recombinant Proteins

Wild-type (WT) and mutant Fc hinge fragments tagged with carboxyl-terminal hexahistidine peptides were purified using $Ni^{2+}$-NTA-agarose (Qiagen, Chatsworth, Calif.) as described previously (Kim et al., 1994a). After dialysis against 15 mM phosphate buffer/50 mM NaCl, pH 7.5, the mutants were either kept at 4° C. for short term storage (<10 days) or freeze dried for longer term storage. Recombinant soluble mouse FcRn was expressed and purified using the baculovirus system as described previously (Popov et al., 1996b) and stored at 4° C.

TABLE XVIII

Recombinant Fc-Hinge Derivatives Used in this Study

| Designation | Mutation | Domain |
|---|---|---|
| WT Fc-hinge | None | |
| I253A[a] | Ile 253 to Ala | CH2 |
| H285A[a] | His 285 to Ala | CH2 |
| H310A | His 310 to Ala | CH2 |
| H433A | His 433 to Ala | CH3 |
| H433A/N434Q[a] | His 433 to Ala and Asn 434 to Gln | CH3 |
| N434A | Asn 434 to Ala | CH3 |
| N434Q | Asn 434 to Gln | CH3 |
| H435A | His 435 to Ala | CH3 |
| H436A | His 436 to Ala | CH3 |

[a]Mutants described previously (Kim et al., 1994a; 1994c)

Analysis of the Mutant Fc Hinge Fragments Using SDS-PAGE and Circular Dichroism (CD)

SDS-PAGE (Laemmli, 1970) and CD analyses were conducted as described previously (Laemmli, 1970).

Radiolabeling of the Proteins

Monoclonal mIgG1, recombinant mouse Fcγ, hinge fragments, and recombinant mouse FcRn (mFcRn) (Popov et al., 1996b) were radiolabeled with [$^{125}$I]Na (Amersham, Arlington Heights, Ill.) using the Iodogen reagent (Fraker and Speck, 1978) as described previously (Kim et al., 1994a). Free iodine was removed by centrifugation on MicroSpin G-25 columns (Pharmacia, Piscataway, N.J.). The specific activities of the radiolabeled proteins were approximately $5\times10^6$ cpm/μg, with <5% free iodine. The radioactive proteins were stored at 4° C. for not more than 1 wk before injection into mice.

Chromatographic Analysis

All radiolabeled Fc hinge fragments were analyzed on an s-250 column (Bio-Rad, Hercules, Calif.) by permeation HPLC. The sera collected from mice injected with radiolabeled Fc hinge fragments at 24 h were pooled and analyzed by HPLC on an s-250 column (Bio-Rad). The radioactivities of the chromatographic fractions were measured with a gamma counter, and the molecular mass and heterogeneity of the radioactive peak were determined.

Determination of Serum IgG Concentration

The concentration of serum IgG was determined using radial immunodiffusion with Nanorid and Bindarid kits (The Binding Site, Birmingham, UK). Precipitin ring diameters were measured electronically.

Pharmacokinetic Analyses

Pharmacokinetics of radioiodinated Fc hinge fragments were determined in 6-wk-old BALB/c mice (Harlan Sprague-Dawley Laboratory, Indianapolis, Ind.) as described previously (Kim et al., 1994a; 1994c).

Maternofetal Transmission

Previously described methodology (Medesan et al., 1996) was used with pregnant outbred SCID) mice (Taconic Co., Germantown, N.Y.) near term (15–18 days). In brief, mice were fed 0.01% NaI in drinking water and then 1 day later injected with radiolabeled protein ($2\times10^7$ and $5\times10^7$ cpm) in the tail vein. Mice were bled with a 20-μl capillary 3 min postinjection, and 24 h later fetuses were delivered by cesarean section. The fetuses of a litter were pooled (discarding the placenta), washed in saline, weighed, frozen in liquid nitrogen, and homogenized in 10 vol of 10% TCA. The suspension was centrifuged, and the radioactivity of the precipitate was determined in a gamma counter. The percentage of transmission was calculated with the formula: % transmission (% T)=(R3)/[(R1−R2)×(W×0.72)/0.02], where R1 is radioactivity in maternal blood at 3 min, R2 is radioactivity in maternal blood at 24 h, W is body weight (grams), and R3 is radioactivity of the fetuses.

The total weight and number of fetuses in a given litter varied from litter to litter, and therefore, the transmission data are presented per unit weight of fetuses rather than the amount transferred per litter (% T/g) (Medesan et al., 1996). The blood volume of pregnant mice was considered to be 7.2% of body weight (Guyer et al., 1976). The radioactivity in the maternal blood available for transmission to the fetus was calculated by deducting the radioactivity remaining at 24 h from that measured at 3 min after the injection of radiolabeled protein.

Inhibition of Transintestinal Transfer

BALB/c neonatal mice (10–14 days old) were intubated with a mixture of [$^{125}$I]mIgG1 and Fc hinge fragment at a Fc/IgG molar ratio of approximately 2000 as described previously (Kim et al., 1994b). The percentage of inhibition was calculated relative to the transfer of the same amount of [$^{125}$I]mIgG1 without inhibitor.

Inhibition of FcRn Binding to mIgG1-Sepharose

All Fc hinge derivatives were dialyzed into 50 mM phosphate buffer with 250 mM NaCl and 5 mM $Na_2$EDTA, pH 6.0 (PB-6), and adjusted to a concentration of 1 mg/ml. Three hundred microliters of Fc hinge (WT or mutant) or PB-6 were incubated in Eppendorf tubes with rotation for 30 min at 25° C. with 150 μl of mIgG1-Sepharose (1 mg/ml packed gel, 50% suspension), 50 μl of PB-6 containing 10 mg/ml OVA (Sigma Chemical Co., St. Louis, Mo.), and 10 μl of [$^{125}$I]FcRn (0.1 μg/200,000 cpm). Following incubation, 500 μl of ice-cold PB-6 was added, and the gel was washed three times by centrifugation at 12,000×g for 3 min using ice-cold PB-6-(plus 1 mg/ml OVA). The radioactivity bound to the gel was determined. The gel pellet was resuspended in 1 ml of PB-7.5 (50 mM phosphate buffer containing 250 mM NaCl, 5 mM $Na_2$EDTA with 1 mg/ml OVA), and the supernatant was discarded after centrifugation. The remaining radioactivity bound to the gel was determined. The radioactivity specifically bound to the mIgG1-Sepharose gel was calculated by subtracting the remaining radioactivity from the bound radioactivity. The inhibition of binding of FcRn to mIgG1-Sepharose by Fc derivatives was calculated using the equation: % inhibition=100−100 A/B, where A is the specific radioactivity bound to mIgG1-Sepharose in the presence of Fc hinge fragment, and B is the specific radioactivity bound in the absence of Fc hinge fragment.

Analysis of Binding to Staphylococcal Protein A (SpA)

SpA-agarose gel (0.5 ml) was equilibrated with BP-7 (50 mM phosphate buffer containing 250 mM NaCl, 5 mM Na₂EDTA) and 1 mg/ml OVA (BP-7.5). Fifty to one hundred microliters of each $^{125}$I-labeled Fc hinge fragment containing 50 μg of protein was loaded onto the column, incubated for 15 min, and then washed with 10 column volumes of the same buffer. Bound Fc hinge fragments were eluted with 100 mM acetic acid. The amounts of radioactivity in the flow-through, washes, and eluates were determined. The ratio of bound/unbound was calculated, and the percentage of binding of each mutant relative to the WT Fc hinge fragment was determined.

Results

Expression and Analysis of Mouse Fcγ₁ Hinge Mutants

Plasmids encoding the WT Fc hinge and mutants (Table XVIII) were constructed, and the proteins were expressed and purified using *Escherichia coli* as a host. With the exception of the H285A mutant, the residues that have been mutated are all in close proximity to the CH2–CH3 domain interface (Deisenhofer, 1981) and are also highly conserved in the IgG isotypes of both mouse and man (Kabat et al., 1991). As described previously, the radiolabled Fc hinge derivatives emerged essentially as single peaks with a retention time corresponding to 55 kDa when analyzed on an s-250 column (Kim et al., 1994a). Taken together with HPLC analyses, reducing and nonreducing SDS-PAGE analyses indicated that the Fc hinge derivatives are expressed as a mixture of noncovalently linked and sulfhydryl-linked homodimers. In addition, CD studies of the Fc hinge derivatives showed that the mutations did not result in large scale changes in the structures of the recombinant proteins.

Pharmacokinetic Analysis of the Fc Hinge Fragments

Radiolabeled Fc hinge fragments were injected into mice, and the serum radioactivity was monitored at various time points following injection. For each Fc hinge derivative, the elimination curves in different mice were similar.

For each recombinant Fc hinge fragment, the serum samples collected at the 24 h point from mice within one group were pooled and subjected to HPLC on an s-250 column. For all the Fc hinge fragments, the majority of the radioactivity eluted as a single peak with a retention time corresponding to the molecular mass of the injected protein (55 kDa). In agreement with previous results (Kim et al., 1994a), this indicates that the Fc hinge derivatives persist in serum as homodimeric molecules and are not proteolytically digested or associated with other serum proteins. The pharmacokinetic parameters of the Fc hinge derivatives are shown in Table XIX and the α-phase represents the equilibration time between the intra- and extravascular space, whereas the β-phase represents the elimination of the equilibrated protein from the intravascular space. Furthermore, during the α-phase, any misfolded protein molecules that might be present in the recombinant protein preparations are eliminated; and therefore, the β-phase represents the elimination of correctly folded protein from the intravascular space.

The data clearly demonstrate that some mutations have a significant effect on the β-phase half-life of the corresponding Fc hinge fragment. Thus, mutation of H310 in the CH2 domain has a marked effect on the catabolic rate (Table XIX). In contrast, mutation of H285, located in a loop on the external surface of the CH2 domain distal to the CH2–CH3 interface (Deisenhofer 1981), has no effect on the catabolic rate, and this is consistent with previous findings (Kim et al., 1994c). Simultaneous mutation of H433 and N434 decreases the β-phase half-life to 77 h (36% decrease), while single mutation at each of these positions yielded two mutants (H433A and N434A) with the same half-life as the WT Fc hinge. Substitution of N434 with glutamine instead of alanine (N434Q) also yielded an Fc hinge fragment with a half-life similar to that of the WT Fc hinge (Table A). The half-life of the H433A-N434Q mutant (76.9 h) is greater than the value reported previously (50.3 h) (Kim et al., 1994a), and this is also observed for the WT Fc hinge fragment (119 vs 82.9 h), H28A (106 vs 85 h), and I253A (26 vs 20 h). An explanation for these apparent discrepancies is that the BALB/c mice used in the present work (from Harlan Laboratories) have an IgG concentration of 1.0±0.4 mg/ml (average of 25 mice), which is considerably lower than that in BALB/c mice from the animal colony (4.6±0.8 mg/ml) used in earlier studies (Kim et al., 1994a, 1994c). The concentration-catabolism relation (Mariani and Strober, 1991) predicts that the half-life of IgG will be longer in mice with lower serum IgG concentrations, and this may explain the longer half-lives of the Fc hinge fragments in the cases above where direct comparisons have been made.

Mutation of H435 in the CH3 domain has an effect as marked as that induced by mutation of I253 or H310 in the CH2 domain, clearly indicating that this CH3 domain residue plays an important role in building the catabolic site of mIgG1. Furthermore, the H436A mutant has a half-life of 49 h, demonstrating that H436 plays a more minor role than I253, H310, or H435 in controlling catabolism (Table XIX).

TABLE XIX

Catabolism of recombinant Fc-hinge fragments in BALB/c mice

| Fc-hinge Fragment | α-Phase Half-Life | β-Phase Half-Life |
|---|---|---|
| WT Fc-hinge | 11.9 ± 0.2 | 119.1 ± 11.5 |
| I253A | 9.0 ± 1.8 | 26.2 ± 1.9 |
| H285A | 10.8 ± 3.0 | 106.4 ± 11.7 |
| H310A | 5.8 ± 0.2 | 16.8 ± 1.2 |
| H433A | 9.6 ± 1.0 | 114.8 ± 10.8 |
| H433A/N434Q | 9.4 ± 1.1 | 76.9 ± 10.3 |
| N434A | 9.0 ± 0.2 | 110.0 ± 9.2 |
| N434Q | 11.7 ± 0.3 | 115.0 ± 12.6 |
| H435A | 4.4 ± 0.2 | 17.4 ± 2.8 |
| H436A | 8.5 ± 0.3 | 48.7 ± 2.4 |

Maternofetal Transfer

The analysis of the pharmacokinetics of the Fc hinge fragments was extended to maternofetal transfer studies. The transfer of radiolabeled Fc hinge derivatives from the circulation of near-term pregnant SCID mice to the fetuses was analyzed by measuring the protein-bound radioactivity taken up by fetuses of one litter relative to the radioactivity present in the maternal blood during the 24-h interval used for the transfer study. In an earlier study it was demonstrated that both wt and mutant Fc hinge fragments are transferred to the fetuses as intact molecules (Medesan et al., 1996). Thus, differences in transfer do not appear to be due to differences in susceptibility to proteolysis of wt vs mutant molecules. The transmission of I253A, H310A, and H435A mutants was only approximately 10 to 20% that of the WT Fc hinge or H285A, demonstrating the central role played by these residues in the maternofetal transfer of IgG. Thus, these mutations have similar effects on maternofetal transfer and catabolism. However, the correlation between the β-phase half-life and maternofetal transmission found for I253A, H310A, H433A, and H435A was not observed for the H436A mutant. Relative to WT Fc hinge, this mutant has a similar activity in maternofetal transmission but a shorter half-life (Table XIX and FIG. 12A).

Intestinal Transfer

Figure 12B:
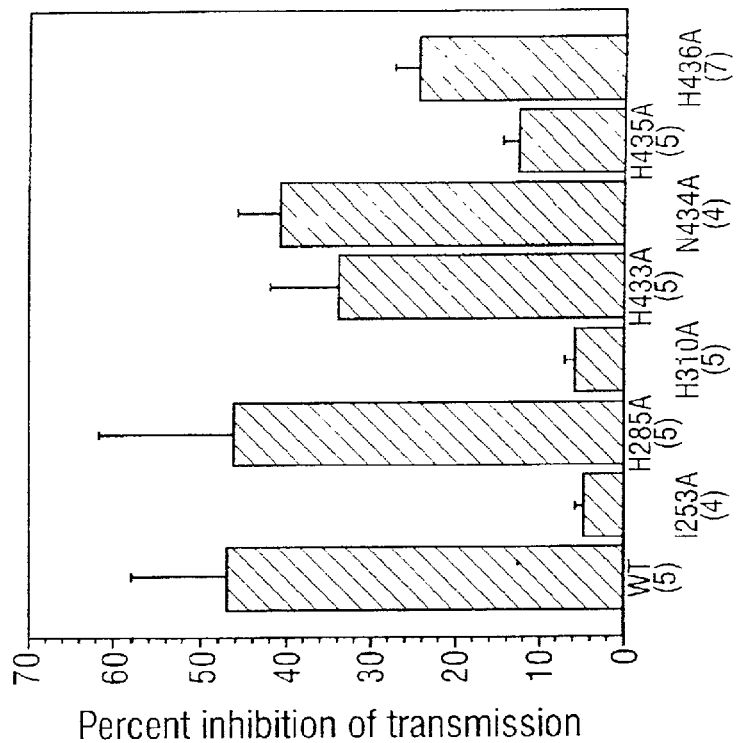
FIG. 12B. Inhibition of intestinal transmission of radiolabeled mIgg1 by recombinant Fc-hinge fragments in BALB/c neonates. The value for H433A is not significantly different from that for WT Fc-hinge. (by Student's test, p=0.127).
Figure 12A:
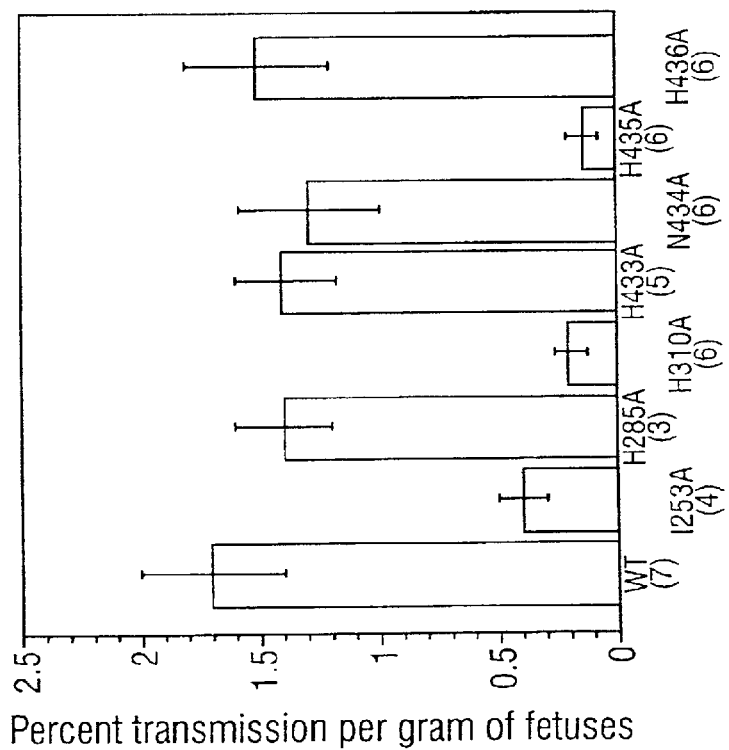
FIG. 12A. Transcytosis of recombinant Fc-hinge fragments. The numbers in parentheses represent the number of mice used for each experiment. Maternofetal transmission of recombinant Fc-hinge fragments in SCID mice.

The intestinal transmission of recombinant Fc hinge derivatives was analyzed by measuring their ability to inhibit the transfer of radiolabeled mIgG1 across the intestinal barrier of neonatal mice (FIG. 12B). The results are consistent with the data obtained for maternofetal transmission of the I253A, H310A, and H435A mutants, indicating that the same receptor and mechanism of transmission are involved in both transcytotic processes. However, the H436A mutant is transferred across the maternofetal barrier of SCID mice almost as efficiently as the WT Fc hinge (FIG. 12A) and yet does not inhibit the transfer of mIgG1 across the neonatal intestine as effectively. Thus, for this mutant, the half-life and inhibition of neonatal transfer are reduced relative to the WT Fc hinge, and yet maternofetal transfer appears to be unaffected.

Affinity for FcRn

The relative affinities of the recombinant Fc hinge fragments for binding to recombinant mFcRn were estimated by measuring their ability to inhibit binding of [$^{125}$I]FcRn to mIgG1-Sepharose (FIG. 13A). The data demonstrate that in all cases, the mutants with short half-life and decreased activity in transcytosis assays (maternofetal and neonatal) also have a lower affinity for binding to FcRn, with the exception of H436A. Despite a lower relative affinity for FcRn, this mutant is transferred across the maternofetal barrier as efficiently as WT Fc hinge, and yet has a reduced serum half-life and activity in intestinal transfer assays.

Binding to SpA

It has been previously shown that the SpA binding site and the catabolic site are located at the CH2–CH3 domain interface of mIgG1 (Kim et al., 1994a), and therefore, the effect of mutations on the binding of the Fc hinge fragments to SpA were analyzed in direct binding studies (FIG. 13B). The data indicate that H310A and H435A are greatly impaired in SpA binding (9–12% of WT), whereas mutation of I253 or H433 has a less marked effect (30–35% of WT).

This study demonstrates that amino acid residues of the CH2 domain (I253 and H310) and CH3 domain (H435 and, to a lesser extent, H436) are involved in regulating the transcytosis and serum persistence of mIgG1. Although this conclusion is drawn from the analysis of recombinant Fc hinge fragments that are expressed in an aglycosylated form, earlier studies demonstrated that the WT Fc hinge fragment has the same β-phase half-life (Kim et al., 1994a) and activity in transcytosis assays (Kim et al., 1994b) as complete glycosylated mIgG1, indicating that for this isotype it is valid to extend studies with aglycosylated Fc hinge fragments to complete IgGs. Thus, residues in both domains play a key role in the two processes that involve FcRn-mIgG1 interactions. This conclusion may appear to contradict an earlier statement that mutations in the CH2 domain have a more marked effect than mutations in the CH3 domain (Kim et al., 1994a; 1994c; 1994b; Medesan et al., 1996). However, in these earlier studies only the effect of simultaneous mutation of both H433 and N434 on transcytosis/catabolism was analyzed, and this indicated a minor role for these residues. In the current analysis, mutation of each of these two amino acids individually has insignificant effects on both transcytosis and catabolism. The most plausible explanation for the observed effects of mutation of both H433 and N434 is that simultaneous mutation of these two amino acids causes a local perturbation in the orientation of the adjacent histidine (H435), which, in contrast to H433 and N434, plays a critical role in the FcRn-mIgG1 interaction.

Further analysis of the region encompassing H310 and Q311, which had previously been analyzed in the context of simultaneous mutation of H310, Q311 to A310, N311, demonstrates the central role of H310 in the FcRn-mIgG1 interaction. Mutation of H310 to alanine has an effect that is as marked as that seen for the H310A/Q311N mutant analyzed earlier, and for this reason the effect of mutation of Q311 alone was not investigated in the current study. In contrast to I253, H310, and H435, H436 plays a more minor role in maintaining serum IgG levels and transcytosis. Both I253 and H310 are highly conserved in all murine and human IgG isotypes (Kabat et al., 1991), whereas H435 and H436 show a lesser degree of conservation (Y435, Y436 in mIgG2b; L436 in a mIgG2a allotype; Y436 in human IgG1, IgG2, and IgG4, F436 in human IgG3 and R435 in a human IgG3 allotype). These sequence differences might account for the shorter serum half-lives of mIgG2b and human IgG3 (Ward and Ghetie, 1995) relative to other IgG isotypes. To date, there are no consistent data available concerning the relative transcytotic activities of different human (Mellbye and Natvig, 1973) and mouse IgG (Guyer et al., 1976) isotypes, and therefore, it is not possible to hypothesize about the effects of amino acid differences at positions 435 and 436 on maternofetal or neonatal transfer. In contrast to IgGs, IgM, IgE, and IgA have short serum half-lives and are not transferred across the placental/yolk sac barrier or neonatal gut (Zuckier et al., 1989; Wild, 1973). Consistent with these observations, none of the residues shown in this study to be important for mediating the Fc-FcRn interaction are present in IgM, IgE, and IgA, although these three Ig classes of both humans and mice share significant homology with IgGs in other regions of the respective molecules (Kabat et al., 1991).

I253 is a highly exposed, hydrophobic residue that is conserved in all IgG molecules belonging to mammals (Kabat et al., 1991). In this study mutation of this isoleucine to alanine resulted in considerable decreases in the serum half-life and transcytosis across the maternofetal barrier or neonatal intestine. This clearly indicates that I253 fulfills a key physiological role beyond binding to SpA (Deisenhofer, 1981). The amino acid residues flanking I253 are involved in the binding of human Fc to SpA (Deisenhofer, 1981), and their participation in the binding of FcRn cannot be excluded. Thus, M252 is highly conserved in all IgG isotypes of mouse, rat, guinea pig, rabbit, and human with a few exceptions, such as mIgG1 and rat IgG1/IgG2a, for which threonine replaces methionine (Kabat et al., 1991). Similarly, position 254 is occupied by serine for all isotypes and species except the above-mentioned mouse and rat isotypes that have threonine at this point. These changes in positions 252 and 254 may correlate with longer half-life and more efficient transcytosis of mIgG1 compared with the other isotypes.

For all mutants except H433A and H436A, binding to FcRn and SpA is impaired to a similar degree. H433A has reduced SpA binding relative to WT Fc hinge, but is unaffected when interacting with FcRn. Conversely, the H436A mutation has the opposite effect. Thus, although the SpA and FcRn interaction sites overlap, the overlap is not complete and the "footprints" of SpA and FcRn on mIgG1 are distinct. This is also consistent with the differences in pH dependence that are observed for the FcRn-mIgG1 and SpA-mIgG1 interactions (Wallace and Rees, 1980; Rodewald and Krachenbuhl, 1984; Ey et al., 1978).

The pH dependence of the interaction between IgG and FcRn (binding at pH 6–6.5 and release at pH 7–7.5) (Wallace and Rees, 1980; Rodewald and Kraehenbuhl, 1984) falls in the range of the pK value of the imidazole side chains of histidine. Taken together with the data from this study, this information suggests that the marked pH dependence of the IgG-FcRn interaction is determined by the surface accessible histidine residues at positions 310, 435, and 436 located at the interface of the CH2 and CH3 domains and this conclusion is in accord with data of Bjorkman and colleagues, indicating that for mIgG2a there are three titratable residues in the pH range of 6.4 to 6.9 (Raghavan et al., 1995). Consistent with these studies (Raghavan et al., 1995), analysis of the H310A mutant demonstrates that H310A plays a role in mediating the Fc-FcRn interaction both in vitro and in vivo. In contrast, however, analysis of H433A and H435A shows that for mIgG1, mutation of H435 to alanine results in a loss of affinity for FcRn, whereas H433 does not play a role in FcRn binding. Furthermore, mutation of H436 to alanine results in an Fc hinge fragment that has reduced affinity for FcRn. Thus, the histidines that play a role in mediating the high affinity of the mIgG1-FcRn interaction are H310, H435, and, to a lesser extent, H436. The reasons for the apparent differences in H433 and H435 between these data and those of others (Raghavan et al., 1995) are not clear, but in the latter study different isotypes (mIgG2a, mIgG2b, and human IgG4) with consequent sequence differences in the residues both at and in proximity to the FcRn interaction site were used. Thus, it is conceivable that in the context of differences in the sequences of surrounding residues, the relative roles of H433 and H435 are distinct in different isotypes.

The close correlation between the effect of mutations of the Fc hinge fragments on pharmacokinetics, transcytosis across neonatal brush border/yolk sac, and affinity for FcRn (Table XX) supports the concept that FcRn is involved in all these processes (Ghetie et al., 1996; Junghans and Anderson, 1996). This is also consistent with studies showing that in mice lacking FcRn due to loss of $\beta_2$m expression, IgGs have decreased intestinal transmission (Israel et al., 1995; Zijlstra et al., 1990) and abnormally short serum half-lives (Ghetie et al., 1996; Junghans and Anderson, 1996). For both the control of catabolism and transcytosis, it has been hypothesized that only the IgG molecules bound to FcRn are protected from degradation and reenter the circulation (catabolism) or traverse the yolk sac/neonatal intestine (transcytosis) (Brambell et al., 1964). FcRn was first identified as a functional protein in tissues of different species (placenta, yolk sac, and brush border of neonatal intestine) involved in the transmission of antibody from mother to fetus or neonate (Wallace and Rees, 1980; Rodewald and Krachenbuhl, 1984; Roberts et al., 1990; Simister et al., 1996; Kristoffersen and Matre, 1996; Leach et al., 1996). More recently, mouse FcRn α-chain mRNA has been isolated from organs not involved in maternal transmission of IgGs, such as liver, lung, heart, and spleen (Ghetie et al., 1996). Rat and human homologues of FcRn have also been found to be ubiquitously expressed at the mRNA level (Story et al., 1994; Simister and Mostov, 1989b; Blumberg et al., 1995). This strongly suggests that FcRn might be synthesized by the endothelial cells within these organs. Consistent with this, FcRn α-chain mRNA (Ghetie et al., 1996) and the corresponding protein have been isolated from cultivated mouse endothelial cells (SVEC), suggesting that endothelial cells might be the site of IgG catabolism. The isolation of a human homologue of FcRn from human placenta (Simister et al., 1996; Kristoffersen and Matre, 1996; Leach et al., 1996) that is ubiquitously expressed in adult tissues (Story et al., 1994) together with the high degree of conservation of I253, H310, and H435 in human IgGs (Kabat et al., 1991) indicate that the same mechanisms of maternofetal transfer and homeostasis of serum IgGs are operative in humans. Understanding these processes in molecular detail has implications both for the modulation of the pharmacokinetics of therapeutic IgGs and for the enhancement of maternofetal transfer of IgGs that might be of value in passive immunization of fetuses.

TABLE XX

Pearson's Correlation Coefficient Test

| | Catabolism | Intestinal Transfer | Affinity for FcRn | Protein A Binding |
|---|---|---|---|---|
| Maternofetal Transmission | r = 0.8703<br>p = 0.0049 | r = 0.8928<br>p = 0.0028 | r = 0.8358[a]<br>p = 0.0097 | r = 0.8838<br>p = 0.0036 |
| Catabolism | | r = 0.9450<br>p = 0.0004 | r = 0.9776<br>p = 0.00003 | r = 0.7107<br>p = 0.0482 |
| Intestinal Transfer | | | r = 0.9531<br>p = 0.00025 | p = 0.8361<br>p = 0.0097 |
| Affinity for FcRn | | | | r = 0.7709<br>p = 0.0251 |

[a]Correlation coefficient excluding values obtained for H436A; r = 0.9917; p = 0.00001.

The pH dependence of the FcRn-IgG interaction (Wallace and Rees, 1980; Rodewald and Krachenbuhl, 1984) suggests that the subcellular site (cell surface or intracellular compartment) at which binding occurs differs for neonatal transcytosis and maternofetal transfer/control of catabolism, as discussed previously (Ghetie et al., 1996). Other unknown factors, such as the rate of recycling in these different cellular compartments, may also play a role in determining the effective concentration of FcRn. These differences between the processes and the cell types involved, despite the involvement of a common receptor, may explain the behavior of the H436A mutant, for which the half-life, intestinal transfer, and affinity for FcRn do not correlate with the maternofetal transmission as closely as for the other mutants. A further explanation for the anomalous effects of the H436A mutation might be as follows: mutation of H436 to alanine does not have as marked an effect on catabolism, inhibition of intestinal transfer, and binding to FcRn as those observed for I253A, H310A, and H435A, and in contrast to the other three assays, the maternofetal transfer assay is conducted in the absence of competition by endogenous IgGs using SCID mice. Thus, in this situation the effect of this mutation on maternofetal transfer only manifests itself if an analysis of the time course of transmission is conducted or if transfer is analyzed in the presence of endogenous competing IgGs in, for example, BALB/c mice. In contrast, for mutants such as I253A, H310A, and H435A that have lower affinity than H436A for binding to FcRn in competition assays, the low activities in all three in vivo assays (catabolism, maternofetal transfer, and inhibition of neonatal transcytosis) correlate closely.

In summary, this study has resulted in the unequivocal identification of a role for three highly conserved histidines of mIgG1 (H310, H435, and, to a lesser degree, H436) in the control of catabolism and maternofetal/neonatal transcytosis. Thus, taken together with earlier data implicating I253 in these processes, these residues are critical for the FcRn-mIgG1 interaction. This study further extends the evidence in support of the involvement of FcRn in both transcytosis and catabolism, and has relevance to understanding the molecular mechanisms that regulate these essential functions of IgGs.

EXAMPLE 10

The power of bacteriophage display for the affinity improvement of antibodies for binding to cognate antigen has already been demonstrated. In this study, the system will be used to express mutated Fc fragments and to select for higher affinity variants for binding to FcRn. For this work, milligrams quantities of soluble FcRn (sFcRn) are used and the WT Fc fragment is expressed in functionally active form on the surface of phage.

Strategy for Mutagenesis

Previous work has indicated that Ile 253, His310, His433, Asn434, His435 and His436 play a role, either directly or indirectly, in binding to FcRn (Kim et al., 1994a; 1994b; Medesan et al., 1997 and Example 9). Residues flanking these key residues, and have side chains that, from the X-ray structure of human IgG1 (Deisenhorfer, 1981), are most likely exposed in the vicinity of the CH2–CH3 domain interface were selected for random mutagenesis. Furthermore, these residues should not be conserved within and across species (e.g. in mice compared with humans), suggesting that they are not (directly) involved in catabolism control and transcytosis (or some other important functions of IgGs). Examples of such residues for the murine IgG1 isotype are, in EU numbering (Edelman et al., 1969), Thr252, Thr254, Thr256 (see Example 4 for analysis), Met309, Gln311, Asn315 in the CH2 domain and His433 and Asn434 in the CH3 domain.

Prior to random mutagenesis, the effect of mutating each of these residues to alanine on binding of the Fc fragment to sFcRn is analyzed. If any of these residue changes lower the affinity by more than 10-fold, they are not mutated randomly. However, most of these residues listed above are not highly conserved (Kabat et al., 1991) and it is therefore believed that they are likely to play a key role in the Fc:FcRn interaction and by extension, in control of catabolism and IgG transcytosis. As His433 and Asn434 are highly exposed on a loop protruding from the CH3 domain (Deisenhofer, 1981), there are few flanking residues that would be preferred candidates for mutagenesis. A greater number of mutations are made in the CH2 domain than in the CH3 domain.

These residues are randomly mutated in groups of 2–6 (for example, Gln309/Arg315 random mutants are combined with Thr252, Thr254 and Thr256 random mutants) using oligonucleotides that match the flanking codons precisely but insert random bases in the codon positions corresponding to the residues mutated. For insertion of mutated codons that are distal to each other, within the same Fc gene, two rounds of PCR™ are used with two or more different oligonucleotides. The random bases in the oligonucleotides are designed so that the wobble position of the codon end in A and to avoid biases towards particular amino acids, C may also be removed from the wobble position (as described by Hoogenboom and Winter, 1992). Mutated genes are either assembled by splicing by overlap extension (Horton et al., 1989) or by using unique restriction sites (if located in the proximity of the mutation site). Following mutagenesis, approximately 20 clones made using each mutagenic oligonucleotide are sequenced using the dideoxynucleotide method (Sanger et al., 1977). Expression levels of approximately 20 clones are analyzed using the anti-myc antibody 9E10 and immunoblotting as described previously (Ward et al., 1989).

Selection of Mutants with Higher Affinity for Binding to FcRn

Two strategies for selection of higher variants from libraries of mutated Fc genes are used. In the first, mutated genes are assembled in pHEN1 (Hoogenboom et al., 1991) and used to transfect *E. coli* TG1. As indicated above, the leakiness of suppression results in both soluble Fc and phage bound Fc fragments being exported from the recombinant cells, and these should assemble as homodimers on the surface of phage. Phage bearing Fe fragments ('Fc-phage') are propagated, concentrated by polyethylene glycol precipitation and panned on sFcRn coated Dynabeads/Ni$^{2+}$-NTA-agarose as described previously (Marks et al., 1991; Ward, 1977; Popov et al., 1995). sFcRn are purified from baculovirus infected insect cells as described previously (Popov et al., 1996). Rounds of panning followed by phage propagation should result in enrichment for higher affinity binders. In addition, to select for higher affinity variants, procedures analogous to that described by Winter and colleagues (Hawkins et al., 1992) are used; first, phage are mixed with small amounts of soluble biotinylated sFcRn (<1 µg) such that the antigen is in excess over the phage but at a concentration lower than that of the dissociation constant that is required (7.8 nM; Raghavan et al., 1994). sFcRn bound Fc-phage particles are then used, and Ni$^{2+}$-NTA-agarose added to separate sFcRn bound phage. Second, to select for Fc fragments with lower off rates, Fc-phage particles are preloaded with biotinylated sFcRn and then diluted in to excess unlabeled antigen for variable times prior to addition of streptavidin coated beads as described previously (Hawkins et al., 1992). Alternatively, the selection method used in Example 4 is utilized.

All binding steps are carried out at pH 6 and bound phage eluted at pH 7.4 prior to infection of exponentially growing *E. coli* TG1 cells. Following several rounds of panning, the host strain are switched to the non-suppressor strain *E. coli* HB2151 (Marks et al., 1991). The Fc variants are analyzed as soluble secreted Fc fragments in ELISAs with sFcRn coated plates, using biotinylated Fab fragments derived from the anti-myc tag antibody, 9E10, for detection (note, the complete 9E10 antibody is not used as this is a murine IgG1 antibody and competes with Fc fragments for binding to FcRn). For this, Fc fragments are purified from recombinant *E. coli* cells using the c-myc tag as an affinity purification tag (Marks et al., 1991; Popov et al., 1995); alternatively, the genes are recloned as NcoI-NotI fragments into a vector derivative of VβpelBHis (Ward, 1992) with an in-frame polyhistidine tag for purification using Ni$^{2+}$-NTA-agarose. For detection of His$_6$ tagged proteins, the Fc fragments are biotinylated prior to use (Amersham biotinylation kits). All binding steps in ELISAs are carried out at pH 6.

As the murine Fc fragment is expected to have a high affinity for binding to FcRn (by analogy with the rat FcRn:Fc interaction), it may be difficult to select variants with increased affinity for the FcRn:Fc interaction, particularly if there are two functional binding sites per Fc (increasing the avidity). Thus, an approach based on earlier Fc-hybrid work (Kim et al., 1 994c) is taken. The Fc-hybrid comprises a heterodimer of one WT Fc polypeptide associated with one mutant (HQ-310/HN-433) and has a reduced binding affinity due to loss of avidity, as the HQ-310/HN-433 mutant binds FcRn poorly (Kim et al., 1994b; Popov et al., 1996b). Thus, co-expression of randomly mutated WT Fc fragments with HQ-310/HN-433 may facilitate the selection of higher affinity variants which bind strongly to FcRn as monomers. Such mutants can subsequently be expressed as homodimers and their affinities as bivalent fragments determined.

Randomly mutated Fc fragments (derived from WT Fc) are ligated into a modified version of pHEN1 that has the stop codon removed by site-directed mutagenesis (Zoller and Smith, 1982). Thus, following transformation into *E. coli* all random mutants are expressed as cpIII linked fusions. *E. coli* is also co-transformed with a plasmid made previously by ligating the HQ-310/HN-433 Fc gene into pBGS 19 (a derivative of pUC 119 that confers kanamycin resistance; Spratt et al., 1986). Double transfectants are selected on ampicillin plus kanamycin plates (as described by Kim et al., 1994c; Riechmann et al., 1988) and phage propagated, concentrated by polyethylene glycol precipitation, and panned on sFcRn coated Dynal beads/Ni$^{2+}$-NTA-agarose using the approaches for the selection for higher affinity variants described above.

To express higher affinity variants as soluble secreted proteins, the genes are recloned into pHEN1 and expressed using E. coli HB2151 as host. Alternatively, the genes are cloned into the VβpelBHis (Ward, 1992) derivative to allow purification using Ni$^2$+-NTA-agarose as above. ELISAs are also carried out as above.

Affinity Measurements of Higher Affinity Variants

Fc mutants with higher affinity for FcRn are purified from recombinant E. coli cells using the c-myc epitope or poly-histidine peptide as an affinity purification tag as described previously (Ward, 1992; Marks et al., 1991; Popov et al., 1995). The affinities of these Fc fragments for binding to sFcRn are determined using surface plasmon resonance (SPR) and the BIAcore (Karlsson et al., 1991). This approach has been used to analyze antibody-antigen interactions (Ward, 1995; Borrebaeck et al., 1992), and Bjorkman and colleagues have characterized the interaction of IgG with rat FcRn using SPR (Raghavan et al., 1994; Popov et al., 1996b).

Studies are carried out to determine both the equilibrium binding constant and the kinetic dissociation constant ($Kd = k_{off}/k_{on}$, where $k_{off}$ and $k_{on}$ are off and on rates, respectively). Purified sFcRn are directly coupled to a CM5 chip (Pharmacia) using the standard amine coupling procedure. For chemical coupling, sFcRn are coupled in 10 mM acetate buffer (pH 5.5) at 20 µg/ml. Initially, both types of sensor chip are used and the relative amount of correctly folded sFcRn bound are determined using either murine IgG1 or WT Fc. Fc fragments are transferred to BIAcore running buffer (10 mM HEPES, 3.4 mM EDTA, 150 mM EDTA, 150 mM NaCl and 0.05% P20, pH 7.4) using either a desalting column or dialysis and initially used in a concentration range of 0.05–0.5 mg/ml. These fragments are also purified by size exclusion (HPLC) immediately prior to use to remove aggregates, as this is essential to avoid artifacts. Flow rates of 5–30 µl/min are used.

As an alternative assay format, Fc fragments are coupled to CM5 chips as above, and sFcRn in BIAcore running buffer is initially used in the concentration range of 0.05–0.5 mg/ml. Initial studies are carried out to analyze the interaction between sFcRn and complete IgG1/WT Fc and are then extended to analysis of the mutant Fc fragments that putatively have higher affinities.

Pharmacokinetics of Maternal-fetal and Intestinal Transfer of Fc Mutants

The methodology as described above in the preceding Examples is used.

Incorporation of Higher Affinity Mutation into IgG2a

Of the murine isotypes, IgG2a is the most efficient at ADCC and also carries out complement mediated lysis effectively (Herlyn and Koprowski, 1982; Bindon et al., 1988). The catabolic site residues Ile253, His310, His435 and His436 are also present in IgG2a (Table I) and consistent with this, the half lives of IgG1 and IgG2a are similar (Pollock et al., 1990). Thus, to improve the transcytosis and serum persistence of this isotype, the same mutations that are found to result in improved transcytosis and serum persistence of IgG1 are incorporated into a recombinant Fc fragment derived from the Y-3P hybridoma (IgG2a; Janeway et al., 1984). Recombinant Fc fragments are purified and analyzed using the same methods as those described in previous Examples.

Analyses of the Effect of the Mutations on Complete Glycosylated IgGs

The IgG1 Isotype

A construct for the expression of the murine IgG1 antibody (anti-arsonate) is tailored using the PCR™ with suitable restriction sites for ligation into pRL1 (Riechmann et al., 1988) and used to transfect myeloma NSO cells. In addition, mutations of Fc fragments that result in higher affinity binding to FcRn, increased transcytosis and, possibly, improved serum persistence are incorporated into the Fc gene of this construct using site-directed mutagenesis (Zoller and Smith, 1982). All mutants are sequenced (Sanger et al., 1977) prior to expression analysis to ensure that there are no second site mutations.

Stable transfectants are generated by electroporation of NSO cells followed by selection using mycophenolic acid as described previously (Riechmann et al., 1988) or more preferably by using the baculovirus system to transfect insect cells as described in Example 8. This latter system is preferred as it is faster. For NSO cell trasnfections, clones are isolated by limiting dilution and the expression levels of individual clones is determined by pulsing the cells with $^{35}$S-methionine followed by SDS-PAGE of culture supernatants. PAGE gels are dried down and autoradiographed. IgG1 mutants are purified using arsonate (Ars)-Sepharose or protein A-Sepharose (however, it is conceivable that the mutations that result in higher affinity binding to FcRn have a detrimental effect on protein A binding, and therefore the use of Ars-Sepharose may be preferable). The WT and mutant IgG1 antibodies are radiolabeled and used in pharmacokinetic, maternal-fetal transfer and intestinal transfer studies as described (Kim et al., 1994a; Kim et al., 1994c).

Other Isotypes

The genes encoding murine isotypes (or mutant derivatives) other than IgG1 are used to replace the IgG1 constant regions in the expression construct described above. These constructs are used to transfect NSO cells and Ars specific antibody purified using Ars-Sepharose or SpA-Sepharose. Alternatively, complete glycosylated IgGs are expressed in the baculovirus system as described in Example 8 for murine IgG2b. These antibodies are used in pharmacokinetic, maternal-fetal transfer and intestinal transfer studies as described above.

Mutations at the CH2–CH3 Domain Interface and Effects on Complement Fixation and ADCC If the mutant antibodies are to be used in therapy with their own functions (complement fixation and ADCC), it is important to ensure that if they bind to FcRn with higher affinity and, as a consequence, are transcytosed more efficiently, and have longer serum persistence, they also retain their original properties with respect to ADCC and complement fixation. Murine IgG2a and 2b are most effective at complement fixation and ADCC (Herlyn and Koprowski, 1982; Bindon et al., 1988) and therefore it is particularly important to check that these have not lost activity. In contrast, murine IgG1 is relatively inactive in these two effector functions (Herlyn and Koprowski, 1982; Bindon et al., 1988). The following assays are therefore carried out;

Complement Mediated Lysis

Methodology similar to that described by Duncan and Winter (1988) is used. Sheep red blood cells (RBCs) are washed in PBS and resuspended at $10^9$ cells/ml. Arsonate is coupled to the cells by adding-p-azobenzenearsonate-L-tyrosine-t-Boc-N-succinimide using previously described methodology (Harlow and Lane, 1988). Cells are washed three times in complement fixation diluent (CFD) and resuspended at $10^8$ cells/ml. Cells are labeled by incubation with $Na^{51}CrO_4$ (0.2 mls per ml of cells, specific activity, 1–10 mCi/ml) for 4 hours at 37° C. Serial dilutions of antibody (wild type and mutants) are made in CFD in flat bottom wells of 96 well plates. Fifty microliters of a 1:10 dilution of guinea pig serum and 100 μl derivatized labeled cells are added to each well. Results are expressed using the following formula:

Specific $^{51}$Cr release=(observed release-spontaneous release)/total incorporated activity×100

ADCC

Essentially the methodology of Sarmay and colleagues (1992) is used. Murine or chicken RBCs are derivatized with arsonate and pulsed with $Na^{51}CrO_4$ as described above. Serial dilutions of WT and mutant antibodies are added to wells of 96 well plates (containing $10^5$ cells/well) and effector cells added to the target cells in ratios ranging from 0.5–5 (effector:target). As effector cells, mouse peritoneal macrophages or P388D1 cells activated with IFN-γ (Nathan et al., 1983) are used. Cells are incubated for 12 hours at 37° C. and specific $^{51}$Cr release determined as above.

EXAMPLE 11

This example describes Fab fragments which have much longer serum persistence than $F(ab')_2$ fragments that do not bind to FcRn. These fragments represent non-Fc ligands that bind to FcRn, with a range of affinities, and have longer serum persistence.

Isolation of $F(ab')_2$ Fragments that have Long Serum Persistence

New Zealand white rabbits were immunized subcutaneously with soluable, recombinant FcRn (Popov et al., 1996b) using 100 μg FcRn emulsified in incomplete Freund's adjuvant for subsequent injections at two weekly intervals until a suitable anti-FcRn titer had been reached. Polyclonal sera was then isolated and IgGs purified using protein A-Sepharose (Pharmacia, Piscataway, N.J.). The IgGs were digested with pepsin to generate $F(ab')_2$ and Fc fragments, and purified $F(ab')_2$ fragments separated from Fc and any undigested IgG using protein A-Sepharose. Anti-FcRn $F(ab')_2$ fragments were purified using FcRn-Sepharose and then absorbed using MHC class I expressing RMA cells to remove cross-reactive anti-MHC class I $F(ab')_2$ fragments. $F(ab')_2$ fragments that do not bind to FcRn ("control" $F(ab')_2$) were obtained from preimmune sera of rabbits using the same methods for purification of IgGs followed by digestion with pepsin. Both $F(ab')_2$ preparaions were radioloabeled with Iodogen, as described previously, and used in clearance studies in SWISS mice (34 mice per group). The β phase half lives were 24.6±3.6 hours for the control $F(ab')_2$ and 78.2±4.8 for the anti-FcRn $F(ab')_2$. Clearly the anti-FcRn $F(ab')_2$ fragments (or, most likely, a subset of the $F(ab')_2$ within the polyclonal population) had long serum persistence that approaches the β phase half life of murine IgG1 or Fc-hinge in the same strains (about 120 hours).

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. All claimed matter can be made without undue experimentation.

References

The references listed below are incorporated herein by reference to the extent that they supplement, explain, provide a background for or teach methodology, techniques, and/or compositions employed herein.

U.S. Pat. No. 3,791,932.
U.S. Pat. No. 3,949,064.
U.S. Pat. No. 4,174,384.
U.S. Pat. No. 4,554,101.
U.S. Pat. No. 4,578,770,
U.S. Pat. No. 4,596,792
U.S. Pat. No. 4,599,230
U.S. Pat. No. 4,599,231
U.S. Pat. No. 4,601,903
U.S. Pat. No. 4,603,102.
U.S. Pat. No. 4,608,251

Adelman, Hayflick, Vasser, Seebury, *DNA,* 2/3:183–193, 1983.

Ahouse, Hagerman, Mittal, Gilbert, Copeland, Jenkins, Simister, "Mouse MHC Class I-like Fc receptor encoded outside the MHC," *J. Immunol.,* 151:6076–6088, 1993.

Ames, Prody, Kustu, "Simple, rapid and quantitative release of periplasmic proteins by chloroform," *J. Bacteriol.,* 160:1181–1183, 1984.

Amit, Mariuzza, Phillips, Poljak, *Science,* 233:747–752, 1986.

Arend and Webster, "Catabolism and biologic properties of two species of rat IgG2a fragments," *J. Immunol.,* 118:395–400, 1977.

Batra, Kasturi, Gallo, Voorman, Maio, Chaudhury, Pastan, "Insertion of constant region domains of human IgG1 into CD4-PE40 increases its plasma half life," *Mol. Immunol.,* 30:379–386, 1993.

Better, Chang, Robinson, Horwitz, *Science,* 240:1041–1043, 1988.

Bhat, Bentley, Fischmann, Boulot, Poljak, *Nature,* 347:483–485, 1990.

Bindon, Hale, Waldmann, "Importance of antigen specificity for complement-mediated lysis by monoclonal antibodies," *Eur. J. Immunol.,* 18:1507–1514, 1988.

Blumberg, Koss, Story, Barisani, Polischuk, Lipin, Pablo, Green, Simister, "A major histocompatibility complex class I-related Fc receptor for IgG on rat hepatocytes," *J. Clin. Invest.,* 95:2379, 1995.

Borrebaeck, Malmborg, Furebring, Michaelsson, Ward, Danielsson, Ohlin, "Kinetic analysis of recombinant antibody-antigen interaction: relation between structural domains and antigen binding," *Bio/technol.,* 10:697–698, 1992.

Borst et al., *Nature* 325:683–688, 1987.

Brambell, "The transmission of immunity from mother to young and the catabolism of immunoglobulins," *Lancet,* ii:1087–1093, 1966.

Brambell, Hemmings, Morris, "A theoretical model of gammaglobulin catabolism", *Nature,* 203:1352–1355:1964.

Brenner et al., *Nature* 322, 145–149, 1986.

Brooks, Yuan, Uhr, Krammer, Vitetta, *Nature,* 302:825, 1983.

Burmeister, Gastinel, Simister, Blum, Bjorkman, "Crystal structure at 2.2 A resolution of the MHC-related neonatal Fc receptor," *Nature,* 372:336–341, 1994a.

Burmeister, Huber, Bjorkman, "Crystal structure of the complex of rat neonatal Fc receptor with Fc," *Nature*, 372:379–383, 1994b.

Canfield and Morrison, *J. Exp. Med.*, 173:1483, 1991.

Carter, Bedouelle, Winter, *Nucleic Acids Res.*, 13:4431–4443, 1985.

Chien, Gascoigne, Kavaler, Lee, Davis, "Somatic recombination in a murine T-cell receptor gene," *Nature*, 309:322–326, 1984.

Chothia, Boswell, Lesk, *EMBO J.*, 7:3745–3755:1986.

Covell, Barbet, Holton, Black, Parker, Weinstein, "Pharmacokinetics of monoclonal immunoglobulin G1, F(ab')$_2$ and Fab' in mice," *Cancer Res.*, 46:3969–3978, 1986.

Deisenhofer, "Crystallographic refinement and atomic models of human Fc fragment and its complex from fragment B of protein A from *Staphylococcus aureus* at 2.9 and 2.8 A resolution," *Biochemistry*, 20:2361–2370, 1981.

Deisenhofer, Colman, Epp, Huber, "Crystallographic studies of a human Fc fragment. II. A complete model based on a Fourier map at 3.5 A resolution, *Hoppe-Seyler's Z. Physiol. Chem.*, 357:1421–1434, 1976.

Devaux, Bjorkman, Stevenson, Greif, Elliot, Sagerström, Clayberger, Krensky, Davis, *Eur. J. Immunol.*, 21:2111–2119, 1991.

Dima, Medesan, Mota, Moraru, Sjöquist, Ghetie, "Effect of protein A and its fragment B on the catabolic and Fc receptor sites of IgG," *Eur. J. Immunol.*, 13:605–614, 1983.

Dobre and Ghetie, "Binding of cytophilic rabbit IgG to homologous hepatocytes," *Experientia*, 35:763–764, 1979.

Dorrington and Painter, "Functional domains of immunoglobulin G," *Prog. Immunol.*, 2:76, 1974.

Duncan and Winter, "The binding site for C1q on IgG," *Nature*, 332:738–740, 1988.

Duncan, Woof, Partridge, Burton, Winter, "Localization of the binding site for the human high affinity Fc receptor on IgG", *Nature*, 332:563–564, 1988.

Edelman, Cunningham, Gall, Gottlieb, Rutishauser, Waxdal, "The covalent structure of an entire γG immunoglobulin molecule," *Proc. Natl. Acad. Sci. USA*, 63:78–85;1969.

Ellerson, Yasmeen, Painter, Dorrington, "Structure and function of immunoglobulin domains. III. Isolation and characterization of a fragment corresponding to the Cγ2 homology regions of human immunoglobulin G1," *J. Immunol.*, 116:510–517, 1976.

Evan, Lewis, Ramsay, Bishop, *Mol. Cell. Biol.*, 5:3610–3616, 1985.

Ey, Prowse, Jenkin, "Isolation of pure IgG1, IgG2a and IgG2b immunoglobulins from mouse serum using protein A-Sepharose," *Immunochemistry*, 15:429, 1978.

Filpula and Whitlow, "Single chain Fvs and their fusion proteins", *Methods: A Companion to Methods in Enzymology* 2:97–105, 1991.

Fleury, Lamarre, Meloche, Ryu, Cantin, Hendrickson, Sekaly, *Cell*, 66:1037–1049, 1991.

Fraker and Speck, "Protein and cell membrane iodinations with a sparingly soluble chloramine, 1,3,4,6,-tetrachloro-3a,6a-diphenylglycoluril," *Biochem. Biophys. Res. Commun.*, 80:847–849, 1978.

Fukumoto and Brandon, In: *Protein Transmission through living membranes*, Hemmings, W. A. (Ed.), Elsevier/North-Holland Biomedical Press, p. 399, 1979.

Fung-Leung, Schilham, Rahemtulla, Kundig, Vollenweider, Potter, van Ewijk, Mak, *Cell*, 65:43, 1991.

Gascoigne, *J. Biol. Chem.*, 265:9296–9301, 1990.

Gastinel, Simister, Bjorkman, *Proc. Natl. Acad. Sci. USA*, 89:638, 1992.

Ghetie, Hubbard, Kim, Tsen, Lee, Ward, "Abnormally short serum half-lives of IgG in β2-microglobulin deficient mice", *Eur. J. Immunol.*, 26:690–696, 1996.

Ghetie, Onica, Lenkei, Margineau, "An immunological hypothesis for plasma protein catabolism," *Mech. Aging and Dev.*, 17:27–39, 1981.

Gibson, "Studies on the Epstein-Barr virus genome," Ph.D. Thesis, University of Cambridge, U.K., 1984.

Gittin and Koch, "On the mechanism of maternofetal transfer of human albumin and γ-globulin in the mouse," *J. Clin. Invest.*, 47:1204–1209, 1968.

Goding, In: *Monoclonal Antibodies: Principles and Practice*, Academic Press, London, 1983.

Gram, Marconi, Barbas, Collet, Lerner, Kang, "In vitro selection and affinity maturation of antibodies from a naive combinatorial immunoglobulin library," *Proc. Natl. Acad. Sci. USA*, 89:3576–3580, 1992.

Gregoire, Rebai, Schweisguth, Necker, Mazza, Auphan, Millward, Schmitt-Verhulst, Malissen, *Proc. Natl. Acad. Sci. USA*, 88:8077–8081, 1991.

Guyer, Koshland, Knopf, "Immunoglobulin binding by mouse intestinal epithelial cell receptors," *J. Immunol.*, 117:587–593, 1976.

Harding and Unanue, *Nature*, 346:574–576, 1990.

Harlow and Lane, In: *Antibodies: A Laboratory Manual*, Cold Spring Harbor, N.Y.: Cold Spring Harbor Laboratory, 1988.

Hawkins, Russell, Winter, "Selection of phage antibodies by binding affinity; mimicking affinity maturation," *J. Mol. Biol.*, 226:889–896, 1992.

Herlyn and Koprowski, "IgG2a monoclonal antibody inhibits tumor growth through interaction with effector cells," *Proc. Natl. Acad. Sci. USA*, 79:4761–4765, 1982.

Higuchi, "Using PCR™ to engineer DNA, in 'PCR™ Technology'," (ed. H. A. Erlich, Stockton Press), 61–70, 1989.

Hobbs, Jackson, Hoadley, "Interaction of aglycosyl immunoglobulins with the IgG Fc transport receptor from neonatal rat gut: comparison of deglycosylation by tunicamycin treatment and genetic engineering," *Mol. Immunol.*, 29:949–956, 1992.

Hobbs, Jackson, Peppard, "Binding of subclasses of rat immunoglobulin G to detergent-isolated Fc receptor from neonatal rat intestine," *J. Biol. Chem.*, 262:8041–8046, 1987.

Hogg, Nancy, *Immunology Today*, 9(7 & 8):185–193, 1988.

Honjo, Tasuku, Obata, Masanori, Yamawaki-Kataoka, Yuriko, Kataoka, Tohru, Kawakami, Toshiaki, Takahashi, Naoki, and Mano, Yoshitake, *Cell*, 18:559–568, 1979.

Hoogenboom and Winter, "By-passing immunisation: human antibodies from synthetic repertoires of germline VH gene segments rearranged in vitro," *J. Mol. Biol.*, 227:381–388, 1992.

Hoogenboom, Griffiths, Johnson, Chiswell, Hudson, Winter, "Multisubunit proteins on the surface of filamentous phage: methodologies for displaying antibody (Fab) heavy and light chains", *Nucl. Acids Res.*, 19:4133–4137, 1991.

Hopf, Meyer, zum Büschenfelde, Dierich, "Demonstration of binding sites for IgG, Fc and the third complement component (C3) on isolated hepatocytes," *J. Immunol.*, 117:639, 1976.

Horton, Hunt, Ho, Pullen, Pease, "Engineering hybrid genes without the use of restriction enzymes: gene splicing by overlap extension," *Gene*, 77:61–68, 1989.

Howell, Winters, Olee, Powell, Carlo, Brostoff, *Science*, 246:668–670, 1989.

Huber, Kelley, Gastinel, Bjorkman, "Crystallization and stoichiometry of a complex between a rat intestinal Fc receptor and Fc," *J. Mol. Biol.,* 230:1077–1083, 1993.

Huse et al., *Science,* 246:1275–1281, 1989

Huston, Levinson, Mudgett-Hunter, Tai, Novotny, Margolies, Ridge, Bruccoleri, Haber, Crea, Opperman, *Proc. Natl. Acad. Sci. USA,* 85:5879–5883, 1988.

Ishioka et al., *J. Immunol.,* 152:4310–4319, 1994

Israel, Patel, Taylor, Marshak-Rothstein, Simister, "Requirement for a $\beta_2$-microglobulin associated Fc receptor for acquisition of maternal IgG by fetal and neonatal mice," *J. Immunol.,* 154:6246, 1995.

Israel, Wilsker, Hayes, Schoenfeld, Simister, "Increased clearance of IgG in mice that Pack β2-microglobulin: possible protective role for FcRn", *Immunol.,* 89:573–578, 1996.

Janeway, Conrad, Lerner, Babich, Wettstein, Murphy, "Monoclonal antibodies specific for Ia glycoproteins raised by immunization with activated T cells; possible role of T cell bound antigens as targets of immunoregulatory T cells," *J. Imunol.,* 132:662–667, 1984.

Jefferis, Lund, Pound, "Molecular definition of interaction sites on human IgG for Fc receptors (huFcγR)," *Mol. Immunol.,* 27:1237–1240, 1990.

Johnson, *Proteins,* 7:205–214, 1990.

Jones and Waldmann, "The mechanism of intestinal uptake and transcellular transport in the neonatal rat," *J. Clin. Invest.,* 51:2916–2927, 1972.

Jönsson et al., *BioTechniques,* 11:620–627, 1991.

Junghans and Anderson, "The protection receptor for IgG catabolism is the β2-microglobulin-containing neonatal intestinal transport receptor", *Proc. Natl. Acad. Sci. USA,* 93:5512–5516, 1996.

Kabat, Wu, Perry, Gottesman, Foeller, In: *Sequences of proteins of Immunological Interest,* US Department of Health and Human Services, 1991.

Kandil, Noguchi, Ishibashi, Kasahara, *J. Immunol.,* 154:5907, 1995.

Kappler, Staerz, White, Marrack, *Nature,* 332:35–40, 1988.

Karlsson, Michaelsson, Mattsson, "Kinetic analysis of monoclonal antibody-antigen interactions with a new biosensor based analytical system," *J. Immunol. Methods,* 145:229–240, 1991.

Kim, Tsen, Ghetie, Ward, "Catabolism of the murine IgG molecule: evidence that both CH2–CH3 domain interfaces are required for persistence of IgG1 in the circulation of mice," *Scand. J. Immunol.,* 40:457, 465, 1994c.

Kim, Tsen, Ghetie, Ward, "Identifying amino acid residues that influence plasma clearance of murine IgG1 fragments by site-directed mutagenesis," *Eur. J. Immunol.,* 24:542–548, 1994a.

Kim, Tsen, Ghetie, Ward, "Localization of the site of the murine IgG1 molecule that is involved in binding to the murine intestinal Fc receptor," *Eur. J. Immunol.,* 24:2429–2434, 1994b.

Kim, Tsen, Ghetie, Ward, "Evidence that the hinge region plays a role in maintaining serum levels of the murine IgG1 molecule", *Mol. Immunol.* 32:467–475, 1995.

Koller, Marrack, Kappler, Smithies, *Science,* 248:1227, 1990.

Kristoffersen and Matre, "Co-localisation of the neonatal Fcγ receptor and IgG in human placental term syncytiotrophoblast," *Eur. J. Immunol.,* 26:1668, 1996.

Kunkel, "Rapid and efficient site-specific mutagenesis without phenotypic selection," *Proc. Natl. Acad. Sci. USA,* 82:488, 1985.

Kyte and Doolittle, *J. Mol. Biol.,* 157:105–132, 1982.

Laemmli, "Cleavage of structural proteins during the assembly of the head of bacteriophage T4," *Nature,* 227:680–685, 1970.

Laemmli, *Nature,* 227:680–685, 1970.

Leach, Eaton, Firth, Contractor, *Cell Tissue Res.,* 261:383, 1990.

Leach, Sedmark, Osborne, Rahill, Lairmore, Anderson, "Isolation from human placenta of the IgG transporter, FcRn, and localization to the syncytiotrophoblast," *J. Immunol.,* 157:3317, 1996.

Leatherbarrow, Rademacher, Dwek, *Molecular Immunology,* 22(4):407–415, 1985.

Lin, Devaux, Green, Sagerstrom, Elliott, Davis, *Science,* 249:677–679, 1990.

Lund, Pound, Jones, Duncan, Bentley, Goodall, Levine, Jefferis, Winter, "Multiple binding sites on the CH2 domain of IgG for mouse FcγRII," *Mol. Immunol.,* 29:53–59, 1992.

Lund, Winter, Jones, Pound, Tanaka, Walker, Artymiuk, Arata, Burton, Jefferis, Woof, *J. Immunol.,* 147:2657–2662, 1991.

Mariani and Strober, "Immunoglobulin metabolism," In: *Fc Receptors and the Action of Antibodies,* H. Metzger, Ed. American Society for Microbiology, Washington, D.C., p.94, 1991.

Mariani and Strober, In: *Fc receptors and the action of antibodies,* Metzger, H. (Ed.), ASM, Washington D.C., p. 94, 1990.

Mariuzza and Winter, *J. Biol. Chem.,* 264:7310–7316, 1989.

Marks, Griffiths, Malmqvist, Clackson, Bye, Winter, "By-passing immunization: building high affinity human antibodies by chain shuffling," *Bio/technol.,* 10:779–783, 1992.

Marks, Hoogenboom, Bonnert, McCafferty, Griffiths, Winter, "By-passing immunization: human antibodies from V-gene libraries displayed on phage," *J. Mol. Biol.,* 222:581–597, 1991.

Marquart, Deisenhofer, Huber, *J. Mol. Biol.,* 141:369–391, 1980.

McCafferty et al., *Nature* 348:552, 1990.

McNabb, Koh, Dorrington, Painter, "Structure and function of immunoglobulin domains. V. Binding of immunoglobulin G and fragments to placental membrane preparations," *J. Immunol.,* 117:882, 1976.

Medesan, Matesoi, Radu, Ghetie, Ward, "Delineation of the amino acid residues involved in transcytosis and catabolism of mouse IgG1", *J. Immunol.,* 158:2211–2217, 1997.

Medesan, Radu, Kim, Ghetie, Ward, "Localization of the site of the IgG molecule that regulates maternofetal transmission in mice," *Eur. J. Immunol.,* 26:2533, 1996.

Mellbye and Natvig, "Presence and origin of human IgG subclass proteins in newborns," *Vox Sang.,* 24:206, 1973.

Messing et al., *Nucl. Acids Res.,* 9:309, 1981.

Morris, "The receptor hypothesis of protein ingestion," In: *Antigen Absorption by the Gut,* University Park Press, Baltimore, USA (ed. W. A. Hemmings), pp. 3–22, 1978.

Mostov and Dietcher, *Cell,* 46:613–621, 1986.

Mozes, Kohn, Hakim, Singer, *Science,* 261:91, 1993.

Mueller, Reisfeld, Gillies, "Serum half life and tumor localization of a chimeric antibody deleted of the CH2 domain and directed against the disialoganglioside GD2," *Proc. Natl. Acad. Sci. USA,* 87:5702–5705, 1990.

Narang, Brousseau, Hsuing, Michniewicz, *Methods in Enzymology,* 65:610, 1980.

Nathan, Murray, Wiebe, Rubin, "Identification of interferon-γ as the lymphokine that activates human macrophage oxidative metabolism and antimicrobial activity," *J. Exp. Med.,* 158:670–689, 1983.

Nose and Wigzell, "Biological significance of carbohydrate chains on monoclonal antibodies," *Proc. Natl. Acad. Sci. USA,* 80:6632–6636, 1983.

Nose, Takano, Tyo, Nakamura, Satoshi, Arata, Yoji, Kyogoku, Masahisa, *International Immunology,* 2(11):1109–1112, 1990.

Novotny, Gahjn, Smiley, Hussey, Luther, Recry, Siciliaro, Reinher, *Proc. Natl. Acad. Sci, USA,* 88:8646–8650, 1991.

Novotny, Tonegawa, Saito, Kranz, Eisen, *Proc. Natl. Acad. Sci. USA,* 83:742–746, 1986.

O'Connell and Edidin, "A mouse lymphoid cell line immortalized by simian virus 40 binds lymphocytes and retains functional characteristics of normal endothelial cells," *J. Immunol.,* 144:521–525, 1990.

O'Reilly, Miller, Luckow, "Baculovirus Expression Vectors: A Laboratory Manual," W. H. Freeman and Co., New York, 1992.

Offner, Hashim, Vandenbark, *Science,* 251:430–432, 1991.

Perrier and Mayerson, "Noncompartmental determination of the steady state volume of distribution for any mode of administration," *J. Pharm. Sci.,* 71:372–373, 1986.

Pollock, French, Metlay, Birshtein, Scharff, "Intravascular metabolism of normal and mutant mouse immunoglobulin molecules," *Eur. J. Immunol.,* 20:2021–2027, 1990.

Popov, Hubbard, Kim, Ober, Ghetie, Ward, "The stoichiometry and affinity of interaction of murine Fc fragments with the MHC class I-related receptor, FcRn", *Mol. Immunol.,* 33:521–530, 1996b.

Popov, Hubbard, Ward, "A novel and efficient method for the isolation of antibodies that recognise T cell receptor Vαs, *Mol. Immunol.* 33:493–502, 1996a.

Quistorff, Dich, Grunnert, *In: Animal Cell Culture*, Pollard, J. W. and Walker, J. M. (Eds.), Humana Press, Clifton, N.J., pp. 151–160, 1993.

Raghavan, Bonagura, Morrison, Bjorkman, "Analysis of the pH dependence of the neonatal receptor/immunoglobulin G interaction using antibody and receptor variants", *Biochemistry,* 34:14649–14657, 1995.

Raghavan, Chen, Gastinel, Bjorkman, "Investigation of the interaction between the class I MHC-related Fc receptor and its immunoglobulin G ligand," *Immunity,* 1:303–315, 1994.

Raghavan, Gastinel, Bjorkman, "The class I major histocompatibility complex related Fc receptor shows pH-dependent stability differences correlating with immunoglobulin binding and release," *Biochem.,* 32:8654–8660, 1993.

Riechmann, Foote, Winter, "Expression of an antibody Fv fragment in myeloma cells," *J. Mol. Biol.,* 203:825–828, 1988.

Rink, *Tet. Lett.* 28:3787–3790. 1987.

Roberts, Guenthert, Rodewald, "Isolation and characterization of the Fe receptor from the fetal yolk sac of the rat," *J. Cell Biol.,* 111:1867–1876, 1990.

Rodewald and Kraehenbuhl, "Receptor-mediated transport of IgG," *J. Cell Biol.,* 99:154s-164s, 1984.

Rodewald, "pH dependent binding of immunoglobulins to intestinal cells of the neonatal rat," *J. Cell. Biol.,* 71:666–670, 1976.

Rodewald, *J. Cell. Biol.,* 58:189, 1973.

Rodewald, Lewis, Kraehenbuhl, "Immunoglobulin G receptors of intestinal brush borders of neonatal rats," *Ciba Foundation Symp.,* 95:287–296, 1983.

Rüther, Koenen, Otto, Müller-Hill, *Nucl. Acids Res.,* 9:4087–4098, 1981.

Saiki, Gelfand, Stoffel, Scharf, Higuchi, Horn, Mullis, Erlich, "Primer-directed enzymatic amplification of DNA with thermostable DNA polymerase," *Science,* 239:487–491, 1988.

Sambrook, Fritsch, Maniatis, "Molecular Cloning; a Laboratory Manual," Cold Spring Harbor Press, 1989.

Sanger, Nicklen, Coulson, "DNA sequencing with chain terminating inhibitors," *Proc. Natl. Acad. Sci. USA,* 74:5463–5467, 1977.

Sarmay, Lund, Rozsnyay, Gergely, Jefferis, "Mapping and comparison of the interaction sites on the Fc region of IgG responsible for triggering antibody dependent cellular cytotoxicity (ADC) through different types of human Fc receptor", *Mol. Immunol.,* 29:633–639, 1992.

Scheuermann and Bauer, *Meths. Enzymol.,* 218:446, 1993.

Schumaker, "PKCALC: a basic interactive complex program for statistical and pharmacokinetic analysis of data," *Drug. Metab. Rev.,* 17:331–348, 1986.

Simister and Mostov, "An Fc receptor structurally related to MHC class I antigens," *Eur. J. Immunol.,* 15:733–738, 1985.

Simister and Mostov, "Cloning and expression of the neonatal rat intestinal Fc receptor, a major histocompatibility complex class I antigen homolog," Cold Spring Harbor Symp. Quant. Biol., LIV, 571–580, 1989b.

Simister and Mostov, *Nature,* 337:184, 1989a.

Simister and Rees, "Isolation and characterization of an Fc receptor from neonatal rat small intestine," *Eur. J. Immunol.,* 15:733–738, 1985.

Simister, Story, Chen, Hunt, "An IgG-transporting Fc receptor expressed in the syncytiotrophoblast of human placenta," *Eur. J. Immunol.,* 26:1527, 1996.

Skerra and Plückthun, *Science,* 240, 1038–1041, 1988.

Sleckman, Peterson, Jones, Foran, Greenstein, Seed, Burakoff, *Nature,* 328:351–353, 1987.

Solomon, *In: Foetal and Neonatal Immunity*, North Holland Publishing Company, Amsterdam/London, and American Elsevier Publishing Company, Inc., New York, pp.96–114, 1971.

Spiegelberg and Weigel, "Studies on the catabolism of γG subunits and chains," *J. Immunol.,* 95:1034–1040, 1966.

Spiegelberg and Weigle, *J. Exp. Med.,* 121:323–328, 1965.

Spratt, Hedge, te Heesen, Edelman, Broome-Smith, "Kanamycin resistant vectors that are analogous to plasmids pUC8, pUC9, pEMBL8 and pEMBL9," *Gene,* 41:337–342, 1986.

Spriggs, Koller, Sato, Morrissey, Fanslow, Smithies, Voice, Widmer, Maliszewski, *Proc. Natl. Acad. Sci. USA,* 89:6070, 1992.

Story, Mikulska, Simister, "A major histocompatibility complex class I-like Fc receptor cloned from human placenta: possible role in transfer of immunoglobulin G from mother to fetus," *J. Exp. Med.,* 180:2377–2381, 1994.

Strober, Wochner, Barlow, McFarlin, Waldmann, *J. Clin. Invest.,* 47:1905, 1968.

Takagi, Morinaga, Tsuchiya, Ikemura, Inouye, *Biotechnol.,* 6:948–950, 1988.

Tao and Morrison, "Studies of aglycosylated chimeric mouse-human IgG. Role of carbohydrate in the structure and effector functions mediated by the human IgG constant region," *J. Immunol.,* 143:2595–2601, 1989.

Towbin, Stachelin, Gordon, *Proc. Natl. Acad. Sci.,* 76:4350–4354, 1979.

Vandenbark, Hashim, Offner, *Nature,* 331:541–544, 1989.

Vieira and Rajewsky, *Eur. J. Immunol.,* 18:313, 1988.

Viera and Messing, *In: Methods in Enzymology*, (Eds. R. Wu and L. Grossman, Academic Press, New York), 153:3–11, 1987.

Waldmann and Strober, "Metabolism of Immunoglobulins," *Progr. Allergy,* 13:1–110, 1969.

Wallace and Rees, "Studies on the immunoglobulin-G Fc-fragment receptor from neonatal rat small intestine," *Biochem. J.,* 188:9–16, 1980.

Ward and Ghetie, "The effector functions of immunoglobulins: implications for therapy," *Ther. Immunol.,* 2:77, 1995.

Ward, "Secretion of soluble T cell receptor fragments from recombinant *Escherichia coli* cells," *J. Mol. Biol.,* 224:885–890, 1992.

Ward, "VH shuffling can be used to convert an Fv fragment of anti-hen egg lysozyme specificity to one that recognises a T cell receptor Vα," *Mol. Immunol.,* 32:147–156, 1995.

Ward, Güssow, Griffiths, Jones, Winter, "Binding activities of a repertoire of single immunoglobulin variable domains secreted from *Escherichia coli,*" *Nature,* 341:544–546, 1989.

Ward, *Mol. Immunol.,* 32:147–156, 1995.

Wawrzynczak, Cumber, Parnell, Cumber, Jones, Winter, "Recombinant mouse monoclonal antibodies with single amino acid substitutions affinity Clq and high affinity Fc receptor binding have identical serum half lives in the BALB/c mouse," *Mol. Immunol.,* 29:213–220, 1992.

Weitzman, Palmer, Grennon, "Serum decay and placental transport of mutant mouse myeloma immunoglobulin with defective polypeptide and oligosaccharide," *J. Immunol.,* 122:12–18, 1979.

Whitlow and Filpula, *In: Methods: A Companion to Methods in Enzymology,* 2(2):97–105, 1991.

Wild, "Transport of immunoglobulin and other proteins from mother to young," *In: Lysosomes in Biology and Pathology,* Part 3, J. T. Dingle, Ed., North Holland, Amsterdam, p. 179, 1973.

Wraith, Smilek, Mitchell, Steinman, McDevitt, *Cell,* 59:247–255, 1989.

Yasmeen, Ellerson, Dorrington, Painter, "The structure and function of immunoglobulin domains. IV. The distribution of some effector functions among the Cγ2 and Cγ3 homology regions of human immunoglobulin G1," *J. Immunol.,* 116:518–526, 1976.

Zijlstra, Bix, Simister, Loring, Raulet, Jaenisch, "$\beta_2$-Microglobulin deficient mice lack CD4$^-$8$^+$ cytolytic T cells," *Nature,* 344:742, 1990.

Zoller and Smith, "Oligonucleotide-directed mutagenesis using M13-derived vectors: an efficient and general procedure for the production of point mutations in any fragment of DNA," *Nucl. Acids Res.,* 10:6487–6500, 1982.

Zuckier, Rodriguez, Scharff, "Immunologic and pharmacologic concepts of monoclonal antibodies," *Semin. Nucl. Med.,* 29:166–186, 1990.

Zuckier, Rodriguez, Scharff, *Sem. Nucl. Med.,* 19:166, 1989.

---

What is claimed is:

1. A method of making an antibody with an increased serum half life comprising:

identifying a first amino acid in an IgG Fc-hinge region that is suspected of being directly involved in FcRn binding;

identifying one or more second amino acids wherein each of said second amino acids is in the spatial region of said first amino acid, and wherein the side chain of said second amino acid is exposed to solvent in the native antibody;

making an antibody with a random amino acid substitution of one or more of said second amino acids to make a mutant antibody; and identifying a mutant antibody having an increased serum half life.

2. The method of claim 1, further comprising the step of isolating the identified mutant antibody.

3. The method of claim 2, wherein said first amino acid is amino acid number 253, 310, 435 or 436 of the Fc fragment.

4. The method of claim 1, wherein said second amino acid is amino acid number 252, 254, 256, 309, 311 or 315 in the CH2 domain or 433 or 434 in the CH3 domain.

5. The method of claim 1, wherein two or more of said second amino acids are mutated in a single mutant antibody.

* * * * *